(12) United States Patent
Geisler et al.

(10) Patent No.: US 10,548,900 B2
(45) Date of Patent: Feb. 4, 2020

(54) DNP AND DNP PRODRUG TREATMENT OF NEUROMUSCULAR, NEURODEGENERATIVE, AUTOIMMUNE, DEVELOPMENTAL, TRAUMATIC BRAIN INJURY, CONCUSSION, DRY EYE DISEASE, HEARING LOSS AND/OR METABOLIC DISEASES

(71) Applicants: Mitochon Pharmaceuticals, INC., Radnor, PA (US); Bioventures, LLC, Little Rock, AR (US)

(72) Inventors: John Gerard Geisler, Blue Bell, PA (US); Robert Alonso, North Hampton, NH (US); Peter Anthony Crooks, Little Rock, AR (US); Narsimha Reddy Penthala, Little Rock, AR (US); Zaineb Albayati, Little Rock, AR (US)

(73) Assignees: MITOCHON PHARMACEUTICALS, INC., Radnor, PA (US); BIOVENTURES, LLC, Little Rock, AR (US)

( * ) Notice: Subject to any disclaimer, the term of this patent is extended or adjusted under 35 U.S.C. 154(b) by 10 days.

(21) Appl. No.: 15/451,938

(22) Filed: Mar. 7, 2017

(65) Prior Publication Data
US 2017/0252347 A1    Sep. 7, 2017

Related U.S. Application Data

(60) Provisional application No. 62/304,584, filed on Mar. 7, 2016, provisional application No. 62/460,318, filed on Feb. 17, 2017.

(51) Int. Cl.
*A61K 31/535*      (2006.01)
*A61K 31/5375*     (2006.01)
(Continued)

(52) U.S. Cl.
CPC .......... *A61K 31/5375* (2013.01); *A61K 31/06* (2013.01); *A61K 31/221* (2013.01);
(Continued)

(58) Field of Classification Search
CPC .. A61K 31/5375; A61K 31/06; A61K 31/495; A61K 31/24; A61K 31/4553; A61K 9/0053
(Continued)

(56) References Cited

U.S. PATENT DOCUMENTS 6,664,297 B1   12/2003   Ferreira et al.
2010/0234295 A1   9/2010   Chen

FOREIGN PATENT DOCUMENTS

WO    WO2014/176258    * 10/2014
WO    2015031598 A2    3/2015
(Continued)

OTHER PUBLICATIONS

Sumner, Association constants of anti-hapten monoclonal IgG1 with mouse FCyRII in the presence and absence of hapten, Federation of European Biochemical societies, Oct. 1993, vol. 333, No. 1,2,p. 35-38. (Year: 1993).*

(Continued)

*Primary Examiner* — Taylor V Oh
(74) *Attorney, Agent, or Firm* — Morgan, Lewis & Bockius LLP

(57) ABSTRACT

A composition and method of treatment of neuromuscular, neuromuscular degenerative, neurodegenerative, autoimmune, developmental, traumatic, hearing loss related, and/or metabolic diseases, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-
(Continued)

LASIK surgery, anti-depressants use, Wolfram Syndrome, and Wolcott-Rallison syndrome. The composition is selected from the group consisting of 2,3-DNP, 2,4-DNP, 2,5-DNP, 2,6-DNP, 3,4-DNP, or 3,5-DNP, bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs; Gemini prodrugs, bioprecursor molecules, and combinations thereof. A dose of the composition for treatment of neurodegenerative diseases may be from about 0.01 mg/kg of body weight to about 50 mg/kg of body weight of the patient in need of treatment. A dose of the composition for treatment of metabolic diseases may be from about 1 mg/70 kg of body weight to about 100 mg/70 kg of body weight of the patient in need of treatment, and a maximum dose per day is about 200 mg/70 kg of body weight of the patient in need of treatment.

21 Claims, 23 Drawing Sheets

(51) Int. Cl.
  *A61K 31/4453* (2006.01)
  *A61K 31/495* (2006.01)
  *A61K 31/06* (2006.01)
  *A61K 31/221* (2006.01)
  *A61K 31/223* (2006.01)
  *A61K 31/265* (2006.01)
  *A61K 31/27* (2006.01)
  *A61K 31/40* (2006.01)
  *A61K 31/44* (2006.01)
  *A61K 31/4402* (2006.01)
  *A61K 31/4406* (2006.01)
  *A61K 31/4409* (2006.01)
  *A61K 31/661* (2006.01)

(52) U.S. Cl.
  CPC .......... *A61K 31/223* (2013.01); *A61K 31/265* (2013.01); *A61K 31/27* (2013.01); *A61K 31/40* (2013.01); *A61K 31/44* (2013.01); *A61K 31/4402* (2013.01); *A61K 31/4406* (2013.01); *A61K 31/4409* (2013.01); *A61K 31/4453* (2013.01); *A61K 31/495* (2013.01); *A61K 31/661* (2013.01)

(58) Field of Classification Search
  USPC ...................................................... 514/237.5
  See application file for complete search history.

(56) References Cited

FOREIGN PATENT DOCUMENTS

WO       2015031756 A1    3/2015
WO    WO2015/154732 A1 *  10/2015

OTHER PUBLICATIONS

Dhareshwar SS et al, "Prodrugs of Alcohols and Phenols", Prodrugs: Challenges and Rewards, Part 1, Springer New York, 2007, vol. V, pp. 31-99, retrieved on Apr. 25, 2017 from (https://link.springer.com/chapter/10.1007/978-0-387-49785-3_21); p. 46.

Isaacs NS et al, "The E1cb Route for Ester Hydrolysis: Volumes of Activation as an Additional Criterion of Mechanism", J Chem Soc Perkin Trans II 1988, pp. 557-562 (Apr. 23, 1987).

McQuaker SJ et al, "A Prototypical Small-Molecule Modulator Uncouples Mitochondria in Response to Endogenous Hydrogen Peroxide Production", Chem Bio Chem, 14, pp. 993-1000 (2013).

Perry RJ et al, "Reversal of Hypertriglyceridemia, Fatty Liver Disease, and Insulin Resistance by a Liver-Targeted Mitochondrial Uncoupler", Cell Metabolism, 18, pp. 740-748 (Nov. 5, 2013).

International Search Report, PCT/US2017/021080, dated Jun. 29, 2017.

Josiel B. Domingos et al: "Mechanisms of Nucleophilic Substitution Reactions of Methylated Hydroxylamines with Bis(2,4-dinitrophenyl) phosphate. Mass Spectrometric Identification of Key Intermediates", Journal of Chemistry, vol. 69, No. 18, Sep. 1, 2004, pp. 6024-6033, US, ISSN: 0022-3263, DOI: 10.1021/jo0494735 (abstract only).

Examination Report for EP Patent Application No. 17763866.5 dated Sep. 13, 2019.

* cited by examiner

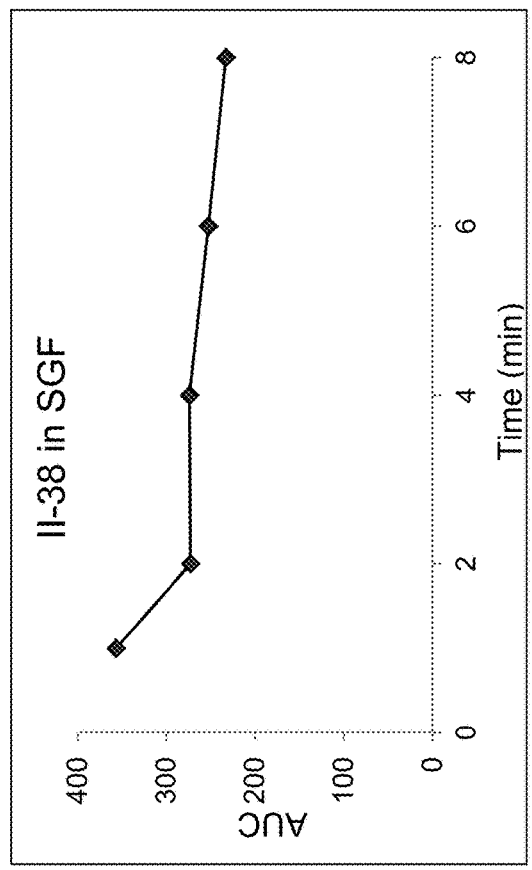
Figure 10A
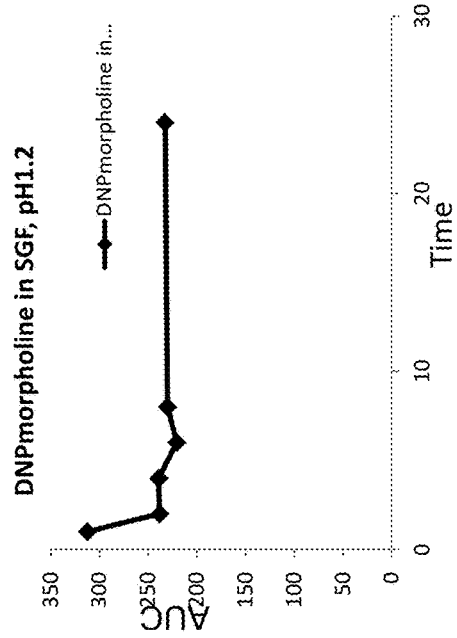
Figure 10B
Figure 10

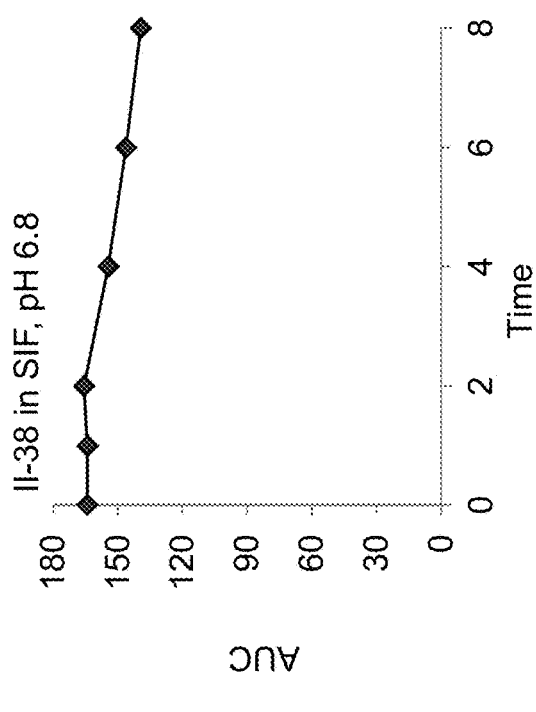
Figure 12A
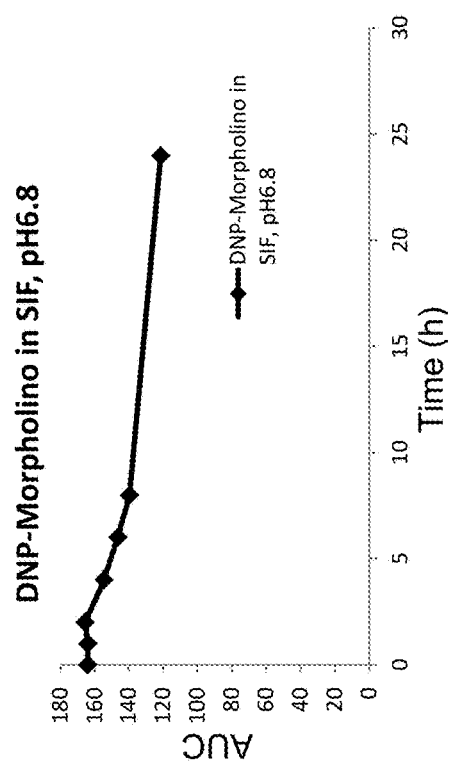
Figure 12B
Figure 12

DNP AND DNP PRODRUG TREATMENT OF NEUROMUSCULAR, NEURODEGENERATIVE, AUTOIMMUNE, DEVELOPMENTAL, TRAUMATIC BRAIN INJURY, CONCUSSION, DRY EYE DISEASE, HEARING LOSS AND/OR METABOLIC DISEASES

CROSS-REFERENCE TO RELATED APPLICATIONS

This application claims the benefit of U.S. Provisional Application No. 62/304,584, filed Mar. 7, 2016, and U.S. Provisional Application No. 62/460,318, filed Feb. 17, 2017, all of which are incorporated herein by reference in their entirety.

FIELD OF THE INVENTION

The present invention relates to development of disease modifying treatments for reversing, slowing or preventing neuromuscular, spinal muscular atrophy (SMA) syndrome (Type I, II, III and IV), neuromuscular degenerative, neurodegenerative, autoimmune, developmental, traumatic brain injury (TBI), concussion, keratoconjunctivitis sicca (Dry Eye Disease), glaucoma, Sjogren's syndrome, hearing loss related, and/or metabolic diseases, including Wolfram Syndrome, Wolcott-Rallison syndrome, and disorders in children, adults and the elderly population. In one aspect, the treatments for neuromuscular, neuromuscular degenerative, neurodegenerative, autoimmune, developmental, traumatic diseases of the CNS, hearing loss related, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, and/or metabolic diseases and disorders, including Wolfram Syndrome, and Wolcott-Rallison syndrome, relate to the use of one or more isomers of dinitrophenol (DNP). The invention also relates to synthesis of bipartite dinitrophenol (2,3-DNP, 2,4-DNP, 2,5-DNP, 2,6-DNP, 3,4-DNP, or 3,5-DNP) prodrugs, and use of the prodrugs and/or 2,3-dinitrophenol, 2,4-dinitrophenol, 2,5-dinitrophenol, 2,6-dinitrophenol, 3,4-dinitrophenol, or 3,5-dinitrophenol for treatment of neuromuscular, neuromuscular degenerative, neurodegenerative, autoimmune, developmental, traumatic diseases of the CNS, hearing loss related, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, and/or metabolic diseases and disorders, including Wolfram Syndrome, and Wolcott-Rallison syndrome.

BACKGROUND

Currently drug therapy to profoundly alter the time course of insidious neuromuscular, neuromuscular degenerative, neurodegenerative, autoimmune, developmental, traumatic, hearing loss related, and/or metabolic diseases towards early death is completely absent, therefore there is a unmet medical need. For instance, current recommendations from the NCL-Foundation due to the severity of the consequences of Batten Disease, is a palliative therapy started as early as possible. Epilepsy is treated with valproate and lamotrigine, spasms with baclofen and tetrazepam, and myoclonus epilepsy with piracetam and zonisamide (leaflet given out by NCL-Stiftung).

Amyotrophic Lateral Sclerosis (ALS, also known as Lou Gehrig's Disease) is a neurodegenerative disorder characterized by loss of neurons in the brain stem, cerebral cortex, and motor neurons of the spinal cord, that leads to progressive weakness and death within 3-5 years upon onset. For ALS, there have been a variety of treatments, and none have been proven effective to curb progression towards death, except riluzole. Riluzole extends life to a modest extent (several months) and extends the time before the patient needs ventilation support, but signs of liver toxicities (~10%) must be monitored.

Alzheimer's Disease (AD), is a disorder characterized by loss of neurons in the brain corresponding to a decline in cognition and premature death. Despite that attempts of a host drug therapies, the drugs have failed to significantly alter lifespan of the patients. Parkinson's Disease, well known for its impact on Michael J. Fox, Mohamed Ali and others, is a slow killer of dopamine producing neurons called the dopaminergic neurons. Current therapies are focused on replacing dopamine and no new advancements have been made in quite a while.

Duchene Muscular Dystrophies (DMD), a pediatric neuromuscular disease in young boys (X-Chromosome), is an aggressive disorder such that the children are in leg braces at 8 years of age and in a wheel chair at 10. The loss of the dystrophin gene affects both the brain and muscle, the only two tissues in which it is expressed. The loss of dystrophin causes osmotic swelling of the mitochondria, bursting, and muscle wasting. Other forms of ataxia, and a host of other neurodegenerative/neuromuscular-degenerative diseases, have no treatments to profoundly alter the course of disease progression towards early death. Multiple sclerosis, is an autoimmune disorder of the CNS with no known etiology. Once disease onset occurs, the myelin sheaths (insulation surrounding nerve fibers or axons) are attacked by the immune cells, causing neuronal dysfunction between the brain and bodily organs. The results is a wide range of neurological symptoms such as involuntary movements of limbs that impair walking, visual/speech impairment, dysfunction of bladder and bowel, etc. Although lifespan is only moderately shortened, MS typically begins to manifest at the age of 20-30, with symptoms progressively getting worse over time. Currently, there are a host of drugs for immune suppression, however none are "disease-modifying" for treating MS, nor do any of the drugs protect against the disease progression.

In addition to neurodegenerative and autoimmune diseases, there is an unmet medical need for treatments of developmental diseases like Angelman Syndrome (AS), a pediatric neurodevelopmental disorder associated with developmental delay, motor dysfunction, lack of speech, and epilepsy caused by mutation in an imprinting gene called ubiquitin ligase E3A (UBE3A). Similarly, Rett Syndrome, is a pediatric degenerative disease that affects young girls (X-Chromosome, boys die in-utero) and leads to death. Currently there are no therapies to treat the effects of the disease that include respiratory issues, movement issues, seizures, etc.

In addition to the useful treatment of neurodegenerative, neuromuscular, autoimmune, and developmental diseases, the pandemic of metabolic diseases has very few drug therapy options that work to the root of the problem to resolve the effects of over-nutrition and subsequently obesity. Obesity is pandemic and intractable. There are approximately 1-billion over-weight adults worldwide, with over 300 million clinically obese. The US alone shows 35% of Americans with a BMI over 30 and 1 out of 400 with a BMI of 50 (~800,000 individuals). Obesity can lead to ectopic lipid accumulation (e.g. nonalcoholic fatty liver disease, NAFLD) and oxidative damage from reactive oxygen species. As a result, obese individuals are at increased risk for numerous other diseases, including insulin resistance, sleep apnea, hypertension, kidney disease, inflammation, knee-joint complications, depression, high blood pressure, cardiovascular disease, Type-2 diabetes (T2D), and even some cancers. While even small amount (~5%) of weight loss can yield metabolic benefits, it is difficult for most patients to achieve and sustain such weight loss. Thus, bariatric surgery is now touted as the best method to reverse obesity. Though increasingly popular, bariatric surgery often requires a permanent anatomical change to the gastrointestinal tract that essentially enforce reduced calorie intake. These procedures are associated with mortality (1/200) and short and long term morbidity such as wound complications and venous thrombosis as well as reactive hypoglycemia, micronutrient deficiency, dumping syndrome, etc. These procedures pose additional challenges in patients with extreme obesity (BMI>50 kg/m$^2$). Pharmaceutical approaches to remedy obesity have focused on inducing malabsorption (e.g., orlistat) or satiety (e.g., rimonobant, sibutramine) but are minimally effective (~5% body weight) and associated with significant adverse effects (e.g. steatorrhea, depression, and MI, respectively). New pharmacological therapies are needed.

Consequently, there is a profound need for improved treatments for neurodegenerative, neuromuscular, developmental, autoimmune and/or metabolic diseases.

SUMMARY OF THE INVENTION

A first aspect of the present invention provides a composition for treating neurodegenerative diseases, neuromuscular diseases, neuromuscular degenerative diseases, developmental diseases, autoimmune diseases, traumatic diseases of the CNS, metabolic diseases, and/or diseases related to hearing loss due to aging, noise, concussion, traumatic brain injury (TBI), drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising one or more isomers of dinitrophenol (DNP), i.e., 2,3-DNP, 2,4-DNP, 2,5-DNP, 2,6-DNP, 3,4-DNP, or 3,5-DNP.

A second aspect of the present invention provides a composition for treating neurodegenerative diseases, neuromuscular diseases, neuromuscular degenerative diseases, developmental diseases, autoimmune diseases, traumatic diseases of the CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising a prodrug, the prodrug being selected from the group consisting of:

an amino acid (AA) ester of 2,3-DNP, 2,4-DNP, 2,5-DNP, 2,6-DNP, 3,4-DNP, or 3,5-DNP (Scheme 1, Formulas I-1 to I-10; Scheme 2, Formulas II-1 to II-10; Scheme 3, Formulas III-1 to III-10; Scheme 4, Formulas IV-1 to IV-10; Scheme 5, Formulas V-1 to V-10; and Scheme 6, Formulas VI-1 to VI-10);

AA esters incorporating a methylene dioxide (a formaldehyde equivalent) spacer (Scheme 1, Formulas I-11 to I-13; Scheme 2, Formulas II-11 to II-13; Scheme 3, Formulas III-11 to III-13; Scheme 4, Formulas IV-11 to IV-13; Scheme 5, Formulas V-11 to V-13; and Scheme 6, Formulas VI-11 to VI-13);

amino carbamate 2,3-DNP, 2,4-DNP, 2,5-DNP, 2,6-DNP, 3,4-DNP, or 3,5-DNP prodrugs (Scheme 1, Formulas I-14 to I-17; Scheme 2, Formulas II-14 to II-17; Scheme 3, Formulas III-14 to III-17; Scheme 4, Formulas IV-14 to IV-17; Scheme 5, Formulas V-14 to V-17; and Scheme 6, Formulas VI-14 to VI-17);

amino carbonate 2,3-DNP, 2,4-DNP, 2,5-DNP, 2,6-DNP, 3,4-DNP, or 3,5-DNP prodrugs (Scheme 1, Formulas I-18 and I-19; Scheme 2, Formulas II-18 and II-19; Scheme 3, Formulas III-18 and III-19; Scheme 4, Formulas IV-18 and IV-19; Scheme 5, Formulas V-18 and V-19; and Scheme 6, Formulas VI-18 and VI-19);

phosphate analogs I-20, I-21, II-20, II-21, III-20, III-21, IV-20, IV-21, V-20, V-21, VI-20, and VI-21 (Schemes 1-6);

1,3 diketo analogs I-22 to I-32; II-22 to II-32; III-22 to III-32; IV-22 to IV-32; V-22 to V-32; and VI-22 to VI-32 (Schemes 1-6);

carbonate and carbamate analogs I-33 to I-39; II-33 to II-39; III-33 to III-39; IV-33 to IV-39; V-33 to V-39; and VI-33 to VI-39 (Schemes 1-6);

benzoate analogs I-40, II-40, III-40, IV-40, V-40, and VI-40 (Schemes 1-6);

and combinations thereof.

A third aspect of the present invention provides a composition for treating neurodegenerative diseases, neuromuscular diseases, neuromuscular degenerative diseases, developmental diseases, autoimmune diseases, traumatic diseases of the CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: a phosphate prodrug altered by introducing a water-soluble prodrug moiety into the molecule through conjugation with the free phenolic functionality.

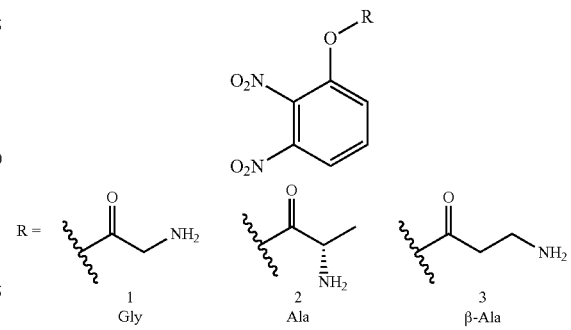

Scheme 1

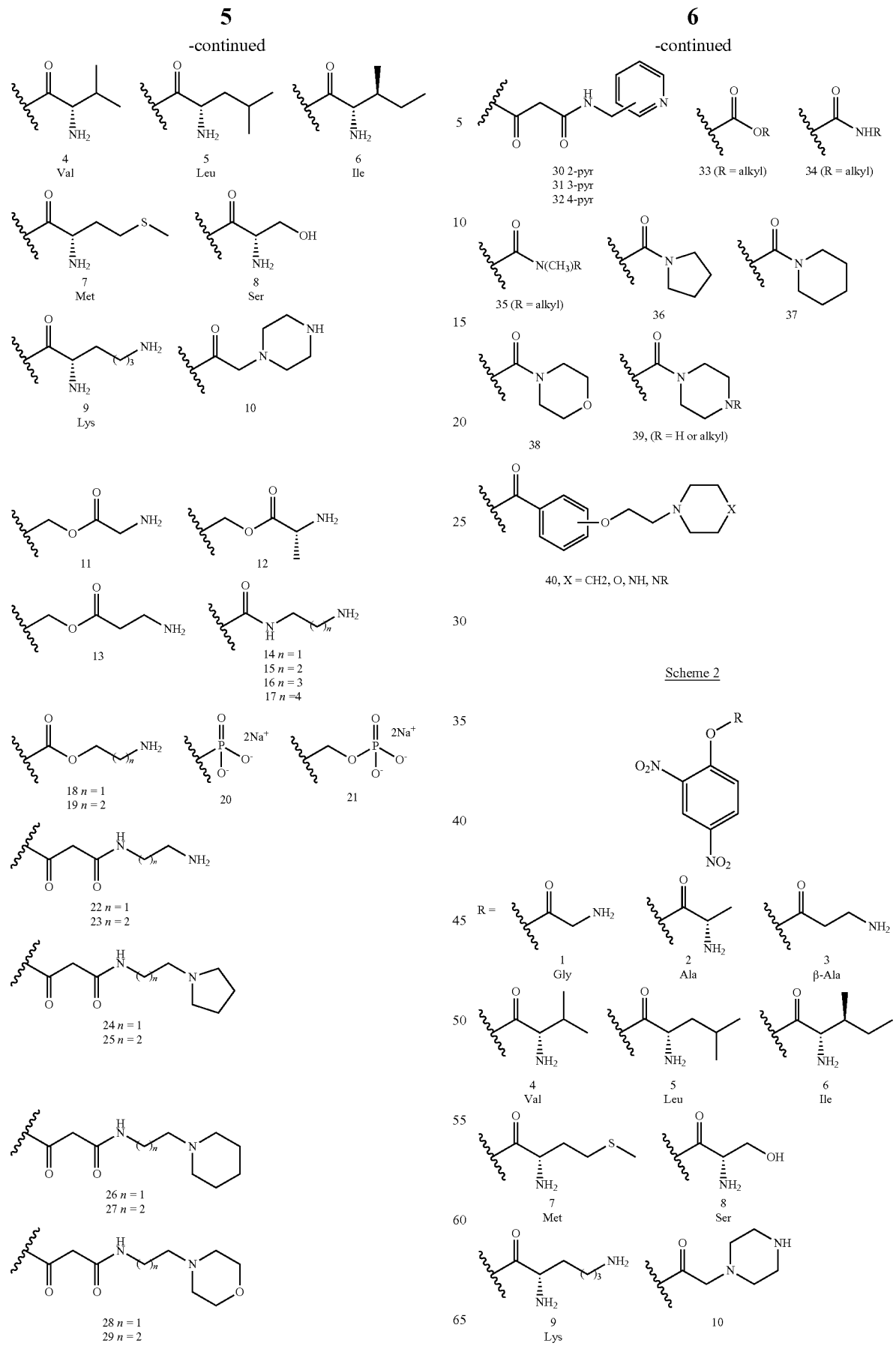

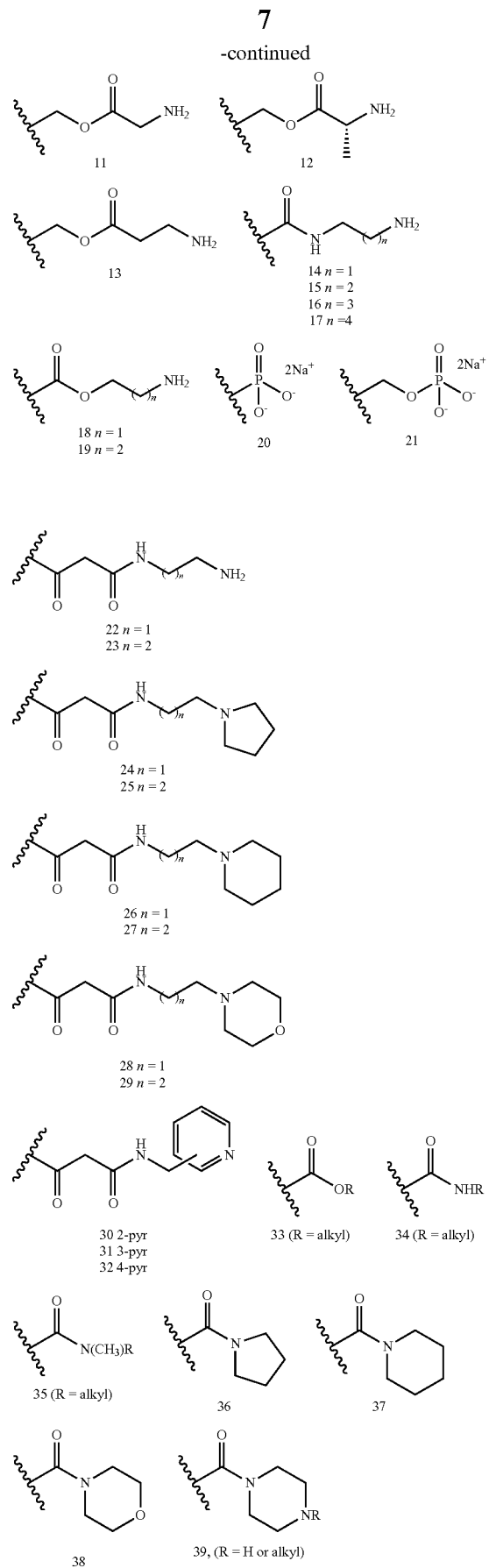
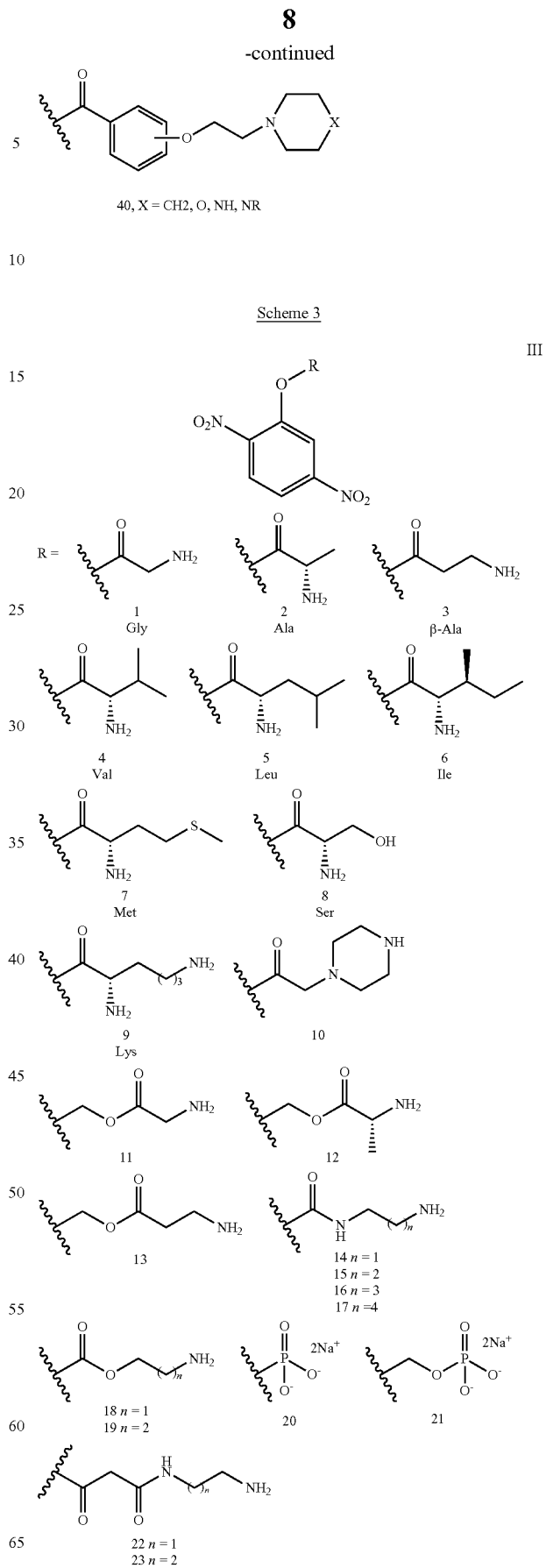

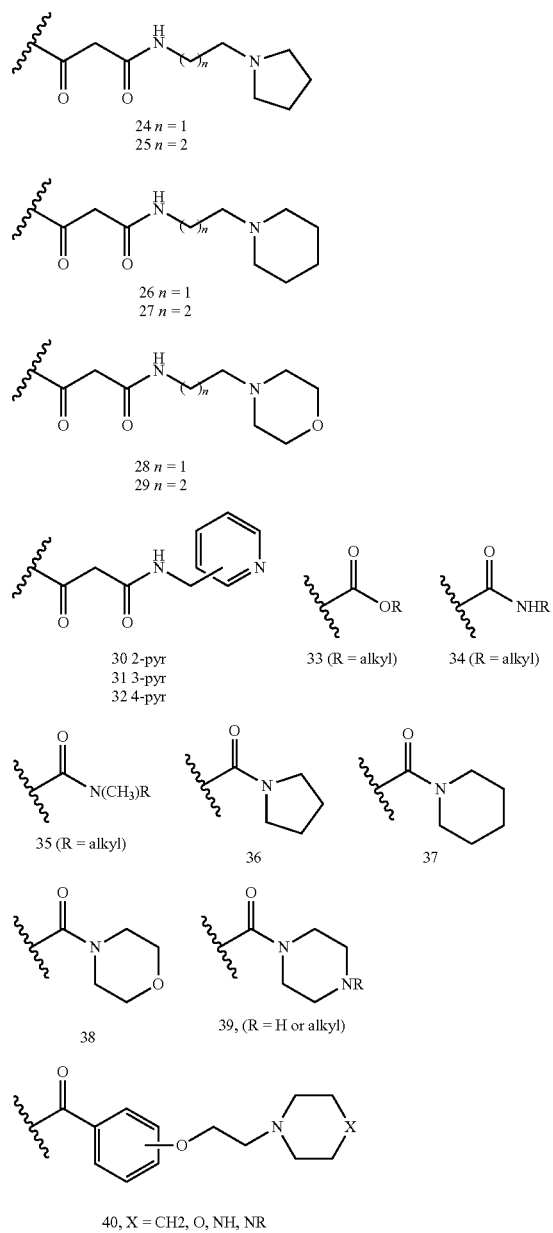
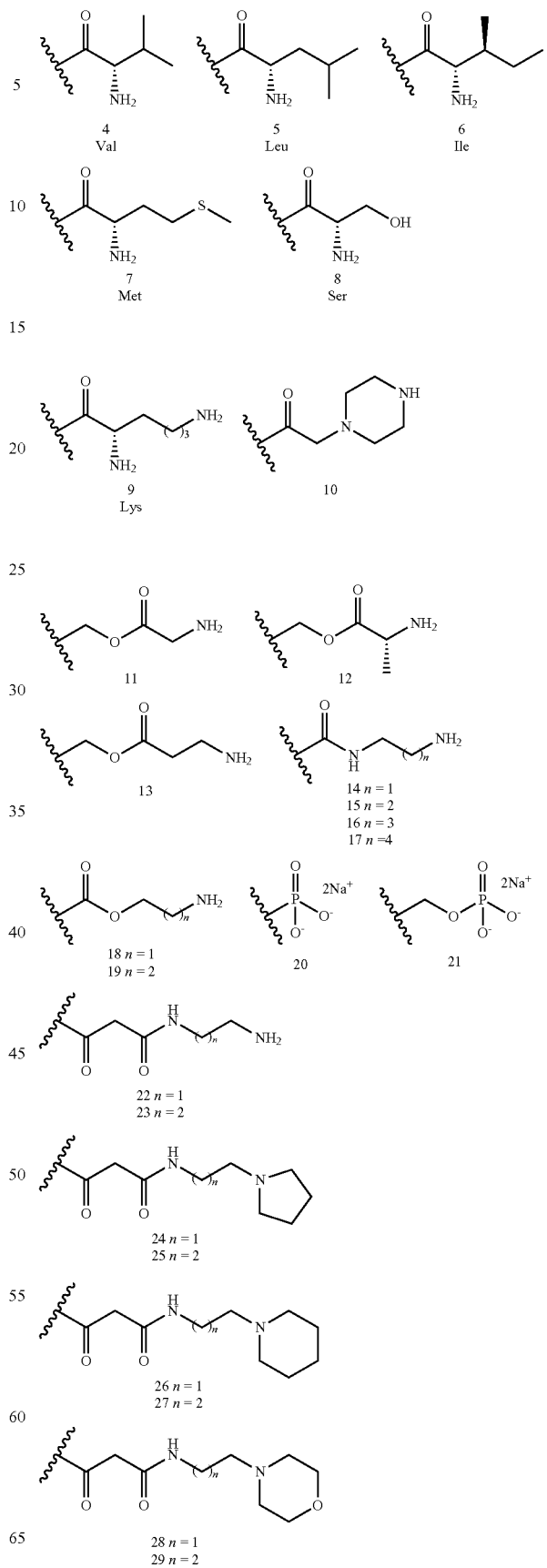
Scheme 4
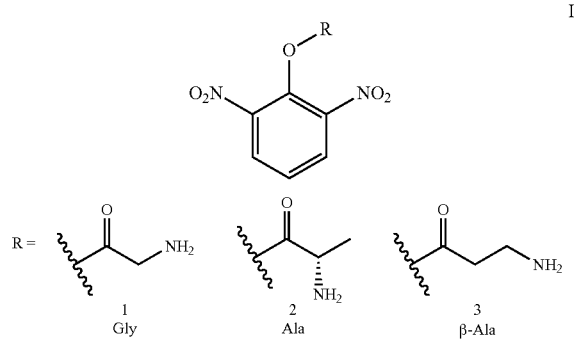

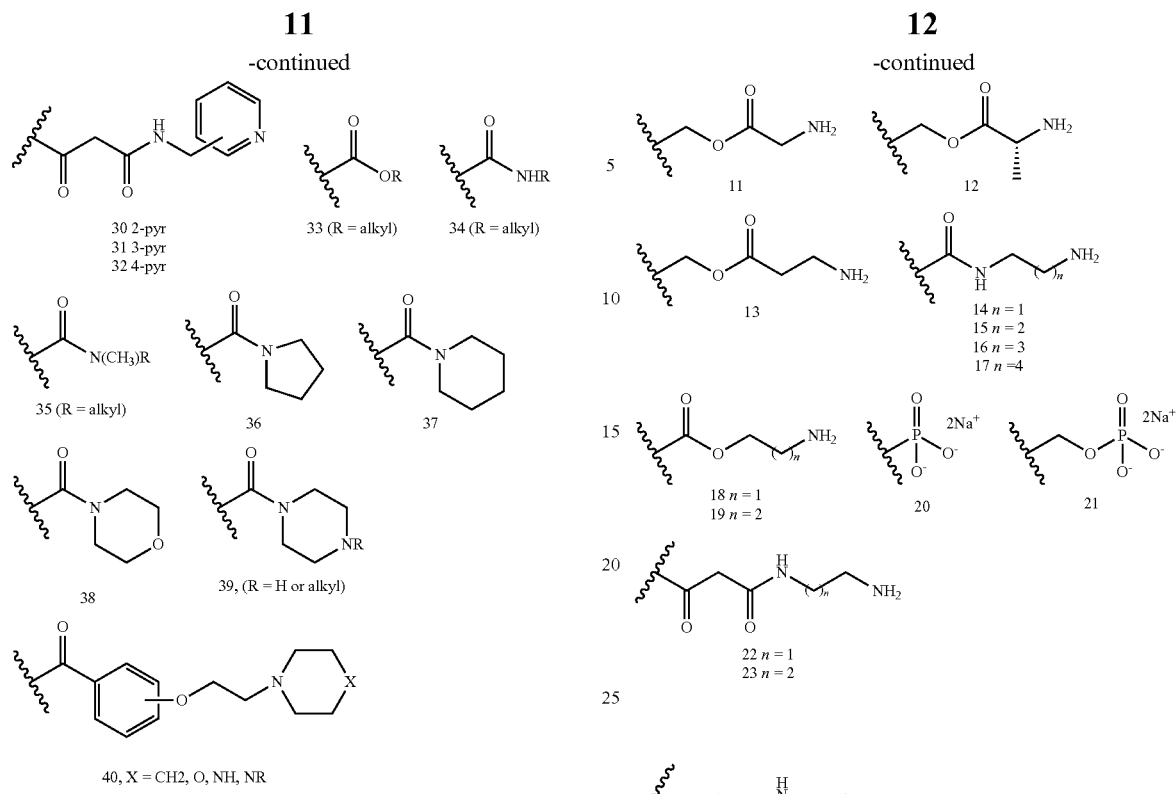
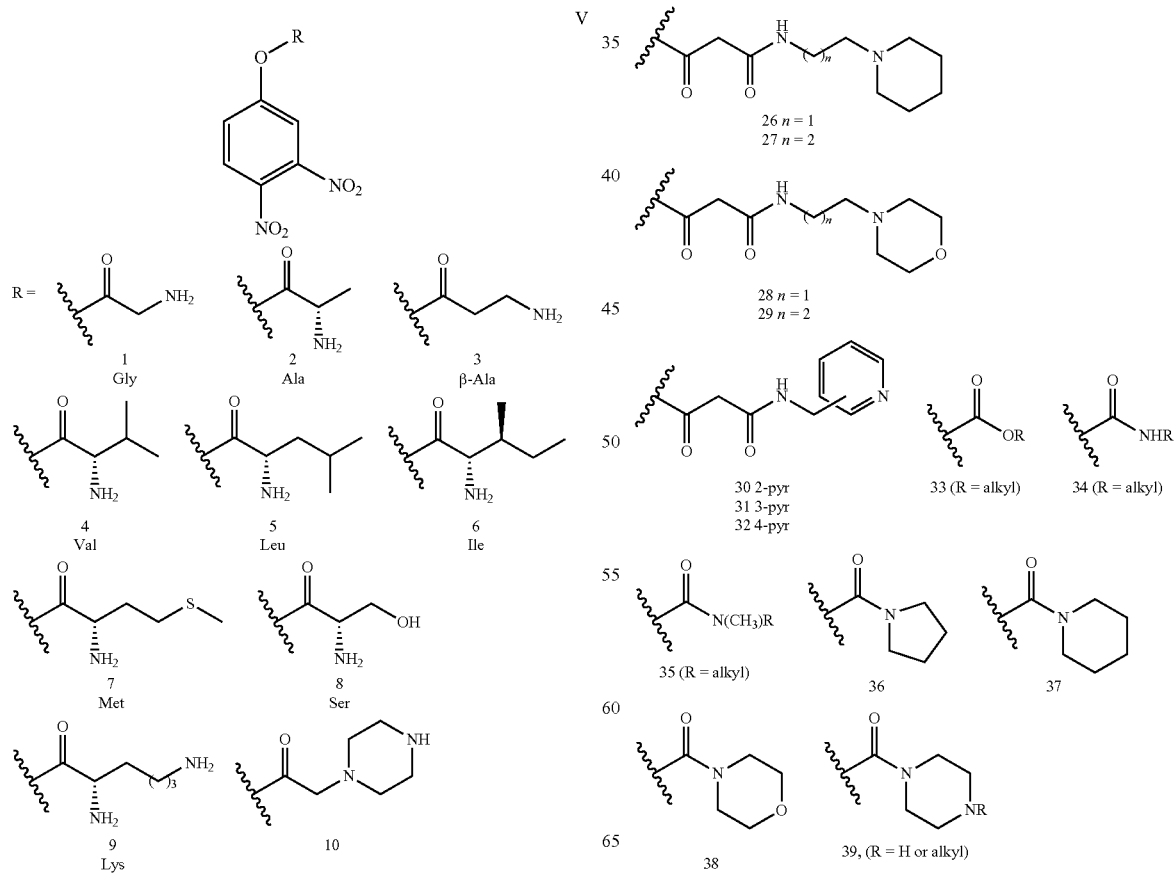

Scheme 6

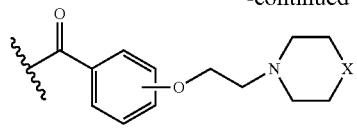

40, X = CH2, O, NH, NR

A fourth aspect of the present invention provides a composition for treating neurodegenerative diseases, neuromuscular diseases, neuromuscular degenerative diseases, developmental diseases, autoimmune diseases, traumatic diseases of the CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: a prodrug, the prodrug being selected from the group consisting of, 2,3-DNP, 2,4-DNP, 2,5-DNP, 2,6-DNP, 3,4-DNP, or 3,5-DNP "Gemini" prodrugs, wherein the prodrug is represented by Formula VII:

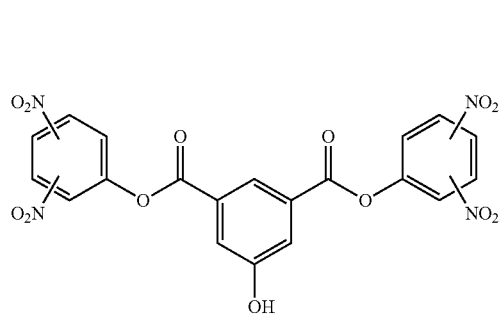

A fifth aspect of the present invention provides a method for synthesizing the composition of a prodrug for treating neurodegenerative neuromuscular diseases, developmental diseases, autoimmune diseases, traumatic diseases of CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome. In one embodiment, the method comprises: reacting 2,3-dinitrophenol, 2,4-dinitrophenol, 2,5-dinitrophenol, 2,6-dinitrophenol, 3,4-dinitrophenol, and/or 3,5-dinitrophenol with 5-(tert-butyldimethylsiloxy)isophthaloyl dichloride (2) in the presence of pyridine/dichloromethane to afford precursor (3); and removing the TBDMS protecting group in acetone/HCl to afford the prodrug (Scheme 7).

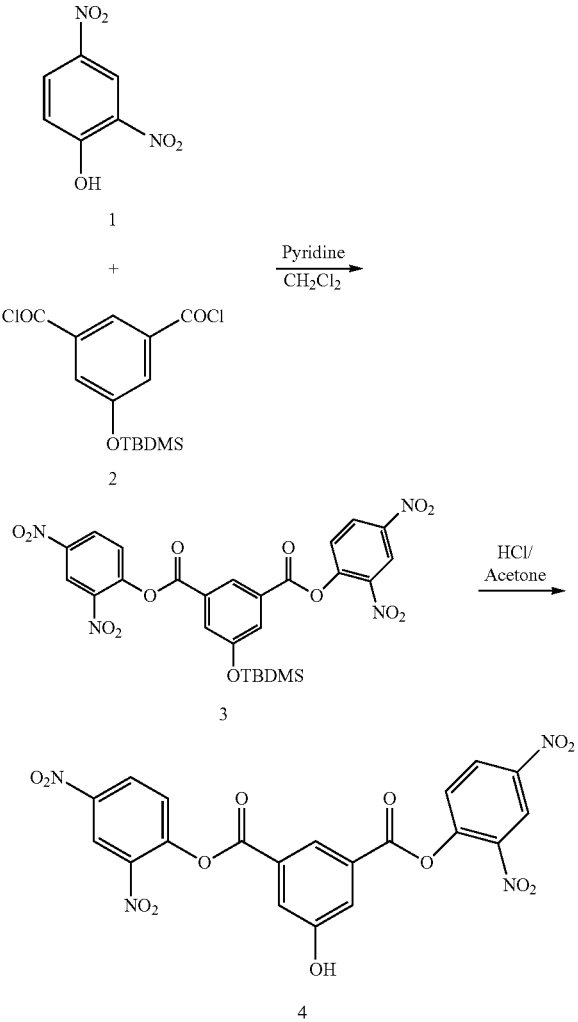

A sixth aspect of the present invention provides a composition for treating neurodegenerative diseases, neuromuscular diseases, neuromuscular degenerative diseases, developmental diseases, autoimmune diseases, traumatic diseases of CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: bioprecursors of 2,3-DNP, 2,4-DNP, 2,5-DNP, 2,6-DNP, 3,4-DNP, or 3,5-DNP that release 2,3-dinitrophenol, 2,4-dinitrophenol, 2,5-dinitrophenol, 2,6-dinitrophenol, 3,4-dinitrophenol, or 3,5-dinitrophenol after oxidative metabolism by cytochrome P-450, wherein the bioprecursors are represented by Formulas VIII and IX (Scheme 8; including synthesis route and oxidative metabolism):

Scheme 8

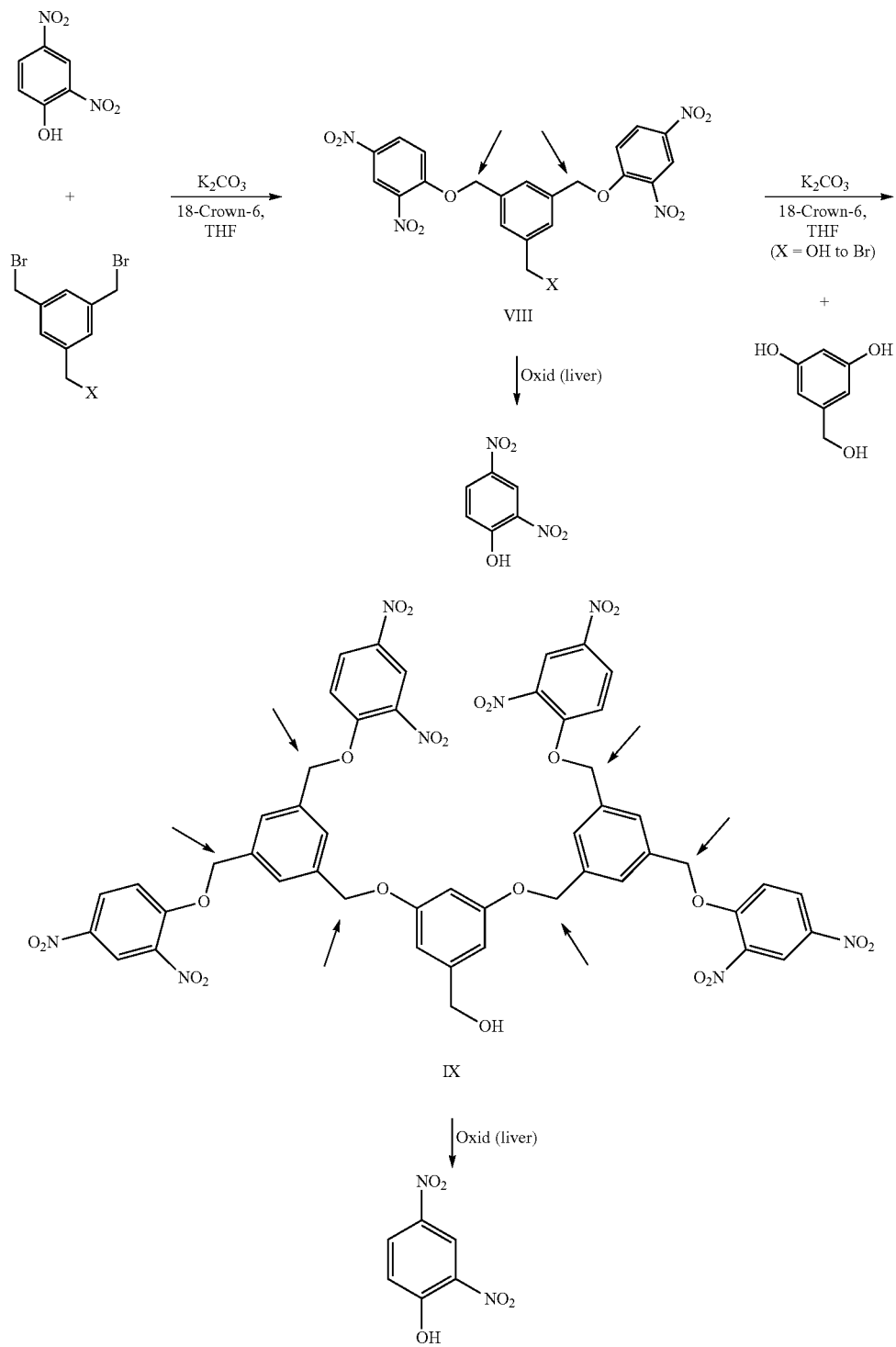

A seventh aspect of the present invention provides a composition for treating neurodegenerative diseases, neuromuscular diseases, neuromuscular degenerative diseases, developmental diseases, autoimmune diseases, traumatic diseases of CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: DNP prodrugs and bioprecursors with linkers containing open functional groups delivered as depot nanoparticle formulations that release DNP in a slow, sustained fashion at low doses compared to dose and release of DNP alone.

An eighth aspect of the present invention provides a method of treatment of neurodegenerative diseases, neuromuscular diseases, neuromuscular degenerative diseases, developmental diseases, autoimmune diseases, traumatic diseases of CNS, metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: administering to a patient in need of treatment a dose of a composition, wherein the composition is selected from the group consisting of 2,3-DNP, 2,4-DNP, 2,5-DNP, 2,6-DNP, 3,4-DNP, or 3,5-DNP, bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs; Gemini prodrugs, bioprecursor molecules, and combinations thereof, and wherein the dose of active drug is from about 0.01 mg/kg of body weight to about 50 mg/kg of body weight of the patient in need of treatment or from about 0.01 mg/kg of body weight to about 25 mg/kg of body weight of the patient in need of treatment.

A ninth aspect of the present invention provides a method of treatment of Traumatic Brain Injury (TBI), Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity Onset Diabetes of the Young (MODY: MODY1, MODY2, MODY3, MODY4, MODY5, MODY6, MODY7, MODY8, MODY9, MODY10, MODY11)), Nonalcoholic Steatohepatitis (NASH), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD), Becker, Myotonic, Congenital, Emery-Dreifuss, Facioscapulohumeral, Limb-girdle, Distal, and Oculopharyngeal), severe burns, aging, Amyotrophic Lateral Sclerosis (ALS), Ataxia (Friedreich's Ataxia, Spinocerebellar ataxias 1 (SCA1), Spinocerebellar ataxias 2 (SCA2), Spinocerebellar ataxias 3 (SCA3), Spinocerebellar ataxias 6 (SCA6), Spinocerebellar ataxias 7 (SCAT), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), Wolfram syndrome (and any associated conditions such as diabetes issues, hearing, vision, ataxia, neurodegeneration, etc.), spinal muscular atrophy (SMA; type I, II, III and IV), hearing loss due to noise (blast and high noise), aging related hearing loss, drug induced hearing loss, and/or genetic hearing loss, concussion, keratoconjunctivitis sicca (Dry Eye Disease), glaucoma, Sjogren's syndrome, rheumatoid arthritis, post-LASIK surgery, anti-depressants use, Wolcott-Rallison syndrome, mitochondrial diseases, developmental disorders, metabolic syndrome (increased blood pressure, high blood sugar level, excess body fat around the waist and abnormal cholesterol levels) and/or autoimmune disorders by increasing energy expenditure and/or inducing BDNF mRNA expression and protein levels with DNP treatment to reverse, slow or prevent neuromuscular and/or neurodegeneration and/or muscle wasting, comprising: administering to a patient in need of treatment a dose of 0.01 mg/kg to 50 mg/kg, wherein the composition is selected from the group consisting of 2,3-DNP, 2,4-DNP, 2,5-DNP, 2,6-DNP, 3,4-DNP, or 3,5-DNP; bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs; Gemini prodrugs, bioprecursor molecules for treating neurodegenerative neuromuscular, developmental, autoimmune and/or metabolic diseases, and combinations thereof, wherein the dose of the composition is from about 0.01 mg/kg to 50 mg/kg of body weight of the patient in need of treatment.

A tenth aspect of the present invention relates to a method of treating neurodegenerative diseases, neuromuscular diseases, neuromuscular degenerative diseases, developmental diseases, autoimmune diseases, traumatic diseases of CNS, and/or metabolic diseases, and/or diseases related to hearing loss due to aging, noise, drug induced, and/or genetic hearing loss, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, comprising: providing instructions to administer an effective dose of DNP, or a pharmaceutically acceptable salt thereof, or any prodrug described herein, over a period sufficiently long to achieve remission of the symptoms of the disease, wherein the effective dose of the DNP and/or prodrug thereof, is instructed to be received in the dose range of 0.001 mg/kg of body weight to 50 mg/kg of body weight.

BRIEF DESCRIPTION OF THE DRAWINGS

The foregoing summary, as well as the following detailed description of embodiments of the invention, will be better understood when read in conjunction with the appended drawings and figures.

FIG. 10A illustrates the stability of II-38 in SGF at pH=1.2.

FIG. 10B illustrates the stability of DNPmorpholine in SGF at pH=1.2.

FIG. 12A illustrates the stability of II-38 in SIF at pH=6.8.

FIG. 12 B illustrates the stability of DNPmorpholino in SIF at pH=6.8.

DETAILED DESCRIPTION OF THE EMBODIMENTS OF THE INVENTION

Definitions

Figure 1:
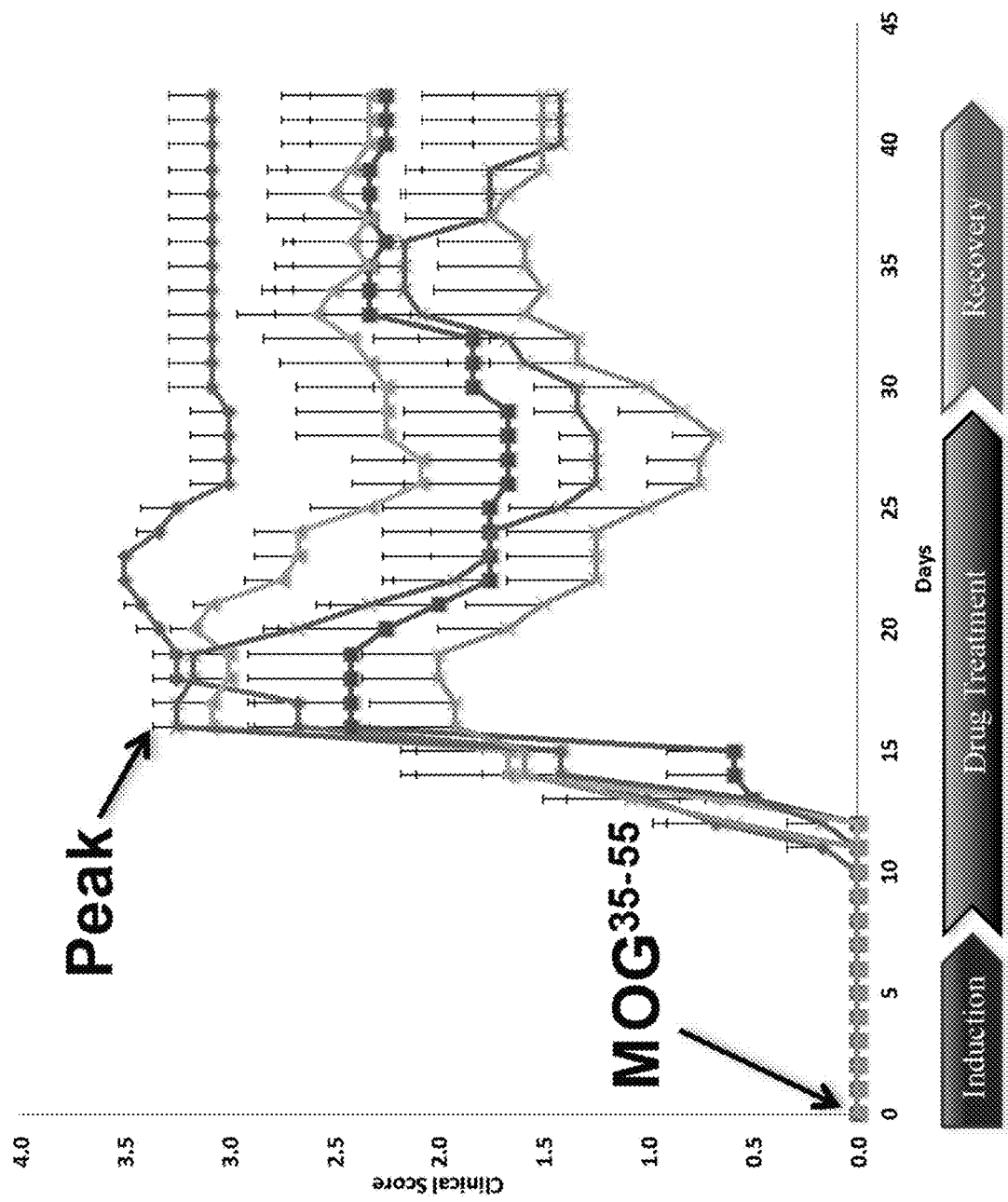
FIG. 1 is a chart illustrating the comparative effect of two compounds of the invention at lowering or blocking progression of paralysis as monitored as a Clinical Score (EAE MS model comparing parent (2,4-DNP) to prodrug (II-38) at equivalent exposures of 5 mpk parent to 80 mpk prodrug for efficacy). Legend: diamond—placebo; square—2,4-DNP 5 mpk; triangle—II-38 8 mpk; x—II-38 16 mpk; asterisk—II-38 80 mpk. P values by Ordinal Regression: 2,4-DNP 5 mpk=0.0192; II-38 8 mpk=0.000954; II-38 16 mpk=0.000124; II-38 80 mpk=0.00014 (results from logistic regression model using ordinal package from cran project, www.cran.r-project.org).

Hereinafter, unless defined otherwise, the term "prodrug" refers to an inactive or partially active drug that is metabolically changed in the body to an active drug.

Hereinafter, the term "depot nanoparticle formulation" unless defined otherwise refers to a biodeliverable nanoparticle, comprising a broad range of 1) bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs, 2) Gemini prodrugs and 3) bioprecursor molecules for treating neurodegenerative or metabolic diseases.

Hereinafter, unless otherwise defined, the term "about" means plus or minus 10% of the value referenced. For example, "about 1 mg/kg" means 0.9 mg/kg to 1.1 mg/kg.

Hereinafter, unless defined otherwise, bipartite 2,3-dinitrophenol, 2,4-dinitrophenol, 2,5-dinitrophenol, 2,6-dinitrophenol, 3,4-dinitrophenol, or 3,5-dinitrophenol are represented by 2,3-DNP, 2,4-DNP, 2,5-DNP, 2,6-DNP, 3,4-DNP, or 3,5-DNP; the prodrug of each isomer is represented in formulas I-VI; being selected from the group consisting of:
an amino acid (AA) ester of 2,3-DNP, 2,4-DNP, 2,5-DNP, 2,6-DNP, 3,4-DNP, or 3,5-DNP (Scheme 1, Formulas I-1 to I-10; Scheme 2, Formulas II-1 to II-10; Scheme 3, Formulas III-1 to III-10; Scheme 4, Formulas IV-1 to IV-10; Scheme 5, Formulas V-1 to V-10; and Scheme 6, Formulas VI-1 to VI-10);

AA esters incorporating a methylene dioxide (a formaldehyde equivalent) spacer (Scheme 1, Formulas I-11 to I-13; Scheme 2, Formulas II-11 to II-13; Scheme 3, Formulas III-11 to III-13; Scheme 4, Formulas IV-11 to IV-13; Scheme 5, Formulas V-11 to V-13; and Scheme 6, Formulas VI-11 to VI-13);

amino carbamate 2,3-DNP, 2,4-DNP, 2,5-DNP, 2,6-DNP, 3,4-DNP, or 3,5-DNP prodrugs (Scheme 1, Formulas I-14 to I-17; Scheme 2, Formulas II-14 to II-17; Scheme 3, Formulas III-14 to III-17; Scheme 4, Formulas IV-14 to IV-17; Scheme 5, Formulas V-14 to V-17; and Scheme 6, Formulas VI-14 to VI-17);

amino carbonate 2,3-DNP, 2,4-DNP, 2,5-DNP, 2,6-DNP, 3,4-DNP, or 3,5-DNP prodrugs (Scheme 1, Formulas I-18 and I-19; Scheme 2, Formulas II-18 and II-19; Scheme 3, Formulas III-18 and III-19; Scheme 4, Formulas IV-18 and IV-19; Scheme 5, Formulas V-18 and V-19; and Scheme 6, Formulas VI-18 and VI-19);

phosphate analogs I-20, I-21, II-20, II-21, III-20, III-21, IV-20, IV-21, V-20, V-21, VI-20, and VI-21 (Schemes 1-6);

1,3 diketo analogs I-22 to I-32; II-22 to II-32; III-22 to III-32; IV-22 to IV-32; V-22 to V-32; and VI-22 to VI-32 (Schemes 1-6);

carbonate and carbamate analogs I-33 to I-39; II-33 to II-39; III-33 to III-39; IV-33 to IV-39; V-33 to V-39; and VI-33 to VI-39 (Schemes 1-6);

benzoate analogs I-40, II-40, III-40, IV-40, V-40, and VI-40 (Schemes 1-6);

and combinations thereof.

In one embodiment, the invention provides compositions and methods for treating neurodegenerative diseases such as Alzheimer's disease, Parkinson, and Huntington's disease. It is believed that the complete lack of historic success is due to most pharmaceutical industries focusing on a downstream event, such as plaques/tangles, whereas the issue is likely upstream at the mitochondria causing high cellular stress. In studies where a mouse model of Alzheimer's disease was treated with DNP under chronic treatment, short term memory was strikingly improved in the Morris Water Maze, having a profound impact on disease progression. Data from a recent study in a Parkinson model using 6-OHDA to destroy the dopaminergic neurons showed that treatment with DNP, had a positive protective effect with chronic treatment.

In one embodiment, the invention provides compositions and methods for treating Huntington's disease. In a model of Huntington's disease, treatment with DNP for over 17-weeks show protection on the spiny neurons, which receive dopamine, therefore the compounds and drugs of the invention should be ideal for the treatment of this disease. DNP should prevent muscle loss since it reduces mitochondrial osmotic swelling by reducing intra-mitochondrial calcium concentration and inducing BDNF, which is a myokine (muscle protectant) outside of the brain.

In one embodiment, the invention provides compositions and methods for treating cognitive disorders associated with DMD in the CNS. 2,4-DNP should for example help the cognitive disorders associated with DMD in the CNS.

In one embodiment, the invention provides compositions and methods for treating Angelman and Rett syndromes. It is believed that oxidative stress is playing a role impairing neurodevelopment, however the fact that DNP prevents overt ROS formation, induces BDNF, reduces seizure duration activity, can have a therapeutic effect in subjects afflicted by these disorders, including children.

In one embodiment, the invention provides compositions and methods for treating obesity. The key to effective weight loss or mechanisms to reduce ectopic fat to improve insulin resistance, fatty liver diseases, Type-2 diabetes, cardiovascular disease, etc., without necessarily marked changes in body weight, is to take the body out of balance regarding energy-in to energy-out, and maintain a mechanism that wastes energy. Thus, new pharmacological therapies focused on enhancing energy expenditure, that address metabolic disease and over-nutritional phenotypes, could potentially have a dramatic effect on the lives of individuals afflicted by these diseases.

Preliminary studies demonstrate (1) ROS reducing capacity and lifespan increase by mitochondrial chemical uncoupler treatment in wildtype mice, and (2) the improved metabolic profile, suggesting that chronic mitochondrial chemical uncoupling treatment is safe and improves health outcomes at low doses (~1-50 mg/day). These preliminary studies demonstrate the rationale for evaluating a mitochondrial chemical uncoupler like DNP and a prodrug formulation for extended release in representative animal models of neurodegenerative, neuromuscular, developmental, autoimmune and/or metabolic diseases, and other cases of overt ROS production, such as during stroke or ischemic events in humans.

Figure 2:
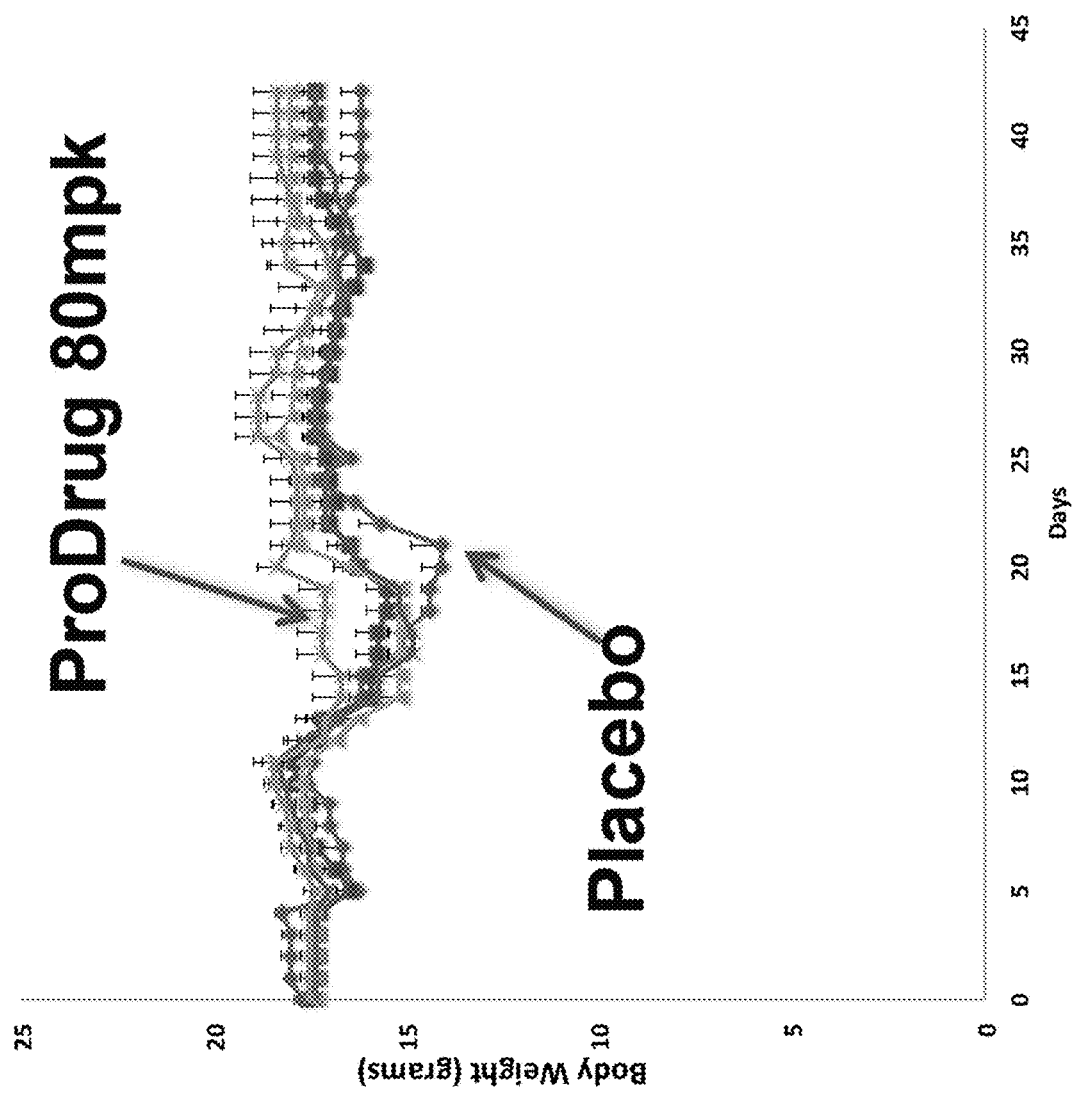
FIG. 2 is a chart illustrating the comparative effect of two compounds of the invention at preventing weight loss seen in the Placebo mice (EAE MS model comparing parent (2,4-DNP) to prodrug (II-38) at equivalent exposures of 5 mpk parent to 80 mpk prodrug for body weight changes). Legend: diamond—placebo; square—2,4-DNP 5 mpk; triangle—II-38 8 mpk; x—II-38 16 mpk; asterisk—II-38 80 mpk. All doses significant to preserving body weight. P values by Ordinal Regression: 2,4-DNP 5 mpk=0.0188; II-38 8 mpk<0.0001; II-38 16 mpk=0.044; II-38 80 mpk<0.0001.

In one embodiment, the compositions and methods of the invention relate to a pharmacological intervention that abolishes overt ROS production and improves the quality of the mitochondrial population by mitophagy, induces Brain Derived Neurotrophin Factor (BDNF), increases cAMP, and/or remodels cellular expression. In one embodiment, a drug of the invention thus becomes "disease modifying." In one embodiment, a prodrug of DNP (II-38) was administered to a mouse model of Multiple Sclerosis, called the EAE, 7-days after induction of the $MOG_{35-55}$ myelin peptide. The ProDrug of DNP, II-38, was administered at multiples of exposure to 2,4-DNP or DNP. Both compounds provided a striking effect at lowering or blocking progression of paralysis as monitored as a Clinical Score (FIG. 1), as well as preventing weight loss seen in the Placebo mice (FIG. 2). Even though DNP historically was used in the 1930's for weight loss at high doses, here it is shown that it can paradoxically be repositioned to prevent wasting associated with neurodegenerative/autoimmune diseases at low doses.

In one embodiment, the compositions described herein may be used to treat hearing loss. In one such embodiment, 2, 4-dinitrophenol (DNP) may be used at a dose range independently selected from: 1 mg/day to 50 mg/day; 1 mg/day to 45 mg/day; 1 mg/day to 40 mg/day; 1 mg/day to 35 mg/day; 1 mg/day to 30 mg/day; 1 mg/day to 25 mg/day; 1 mg/day to 20 mg/day; 1 mg/day to 15 mg/day; 1 mg/day to 10 mg/day; 1 mg/day to 5 mg/day; 1 mg/day to 4 mg/day; 1 mg/day to 3 mg/day; 1 mg/day to 2 mg/day; 2 mg/day to 50 mg/day; 2 mg/day to 45 mg/day; 2 mg/day to 40 mg/day; 2 mg/day to 35 mg/day; 2 mg/day to 30 mg/day; 2 mg/day to 25 mg/day; 2 mg/day to 20 mg/day; 2 mg/day to 15 mg/day; 2 mg/day to 10 mg/day; 2 mg/day to 5 mg/day; 2 mg/day to 4 mg/day; 2 mg/day to 3 mg/day; 0.5 mg/day to 10 mg/day; 0.5 mg/day to 9 mg/day; 0.5 mg/day to 8 mg/day; 0.5 mg/day to 7 mg/day; 0.5 mg/day to 6 mg/day; 0.5 mg/day to 5 mg/day; 0.5 mg/day to 4 mg/day; 0.5 mg/day to 3 mg/day; 0.1 mg/day to 10 mg/day; 0.1 mg/day to 9 mg/day; 0.1 mg/day to 8 mg/day; 0.1 mg/day to 7 mg/day; 0.1 mg/day to 6 mg/day; 0.1 mg/day to 5 mg/day;

0.1 mg/day to 4 mg/day; 0.1 mg/day to 3 mg/day. In one such embodiment, 2, 4-dinitrophenol (DNP) may be used at a dose range independently selected from: about 1 mg/day to about 50 mg/day; about 1 mg/day to about 45 mg/day; about 1 mg/day to about 40 mg/day; about 1 mg/day to about 35 mg/day; about 1 mg/day to about 30 mg/day; about 1 mg/day to about 25 mg/day; about 1 mg/day to about 20 mg/day; about 1 mg/day to about 15 mg/day; about 1 mg/day to about 10 mg/day; about 1 mg/day to about 5 mg/day; about 1 mg/day to about 4 mg/day; about 1 mg/day to about 3 mg/day; about 1 mg/day to about 2 mg/day; about 2 mg/day to about 50 mg/day; about 2 mg/day to about 45 mg/day; about 2 mg/day to about 40 mg/day; about 2 mg/day to about 35 mg/day; about 2 mg/day to about 30 mg/day; about 2 mg/day to about 25 mg/day; about 2 mg/day to about 20 mg/day; about 2 mg/day to about 15 mg/day; about 2 mg/day to about 10 mg/day; about 2 mg/day to about 5 mg/day; about 2 mg/day to about 4 mg/day; about 2 mg/day to about 3 mg/day; about 0.5 mg/day to about 10 mg/day; about 0.5 mg/day to about 9 mg/day; about 0.5 mg/day to about 8 mg/day; about 0.5 mg/day to about 7 mg/day; about 0.5 mg/day to about 6 mg/day; about 0.5 mg/day to about 5 mg/day; about 0.5 mg/day to about 4 mg/day; about 0.5 mg/day to about 3 mg/day; about 0.1 mg/day to about 10 mg/day; about 0.1 mg/day to about 9 mg/day; about 0.1 mg/day to about 8 mg/day; about 0.1 mg/day to about 7 mg/day; about 0.1 mg/day to about 6 mg/day; about 0.1 mg/day to about 5 mg/day; about 0.1 mg/day to about 4 mg/day; about 0.1 mg/day to about 3 mg/day.

In another such embodiment to treat hearing loss, a prodrug of 2,3-DNP, 2,4-DNP, 2,5-DNP, 2,6-DNP, 3,4-DNP, or 3,5-DNP, as described herein, may be used at a dose range to achieve equivalent exposure (AUC) to DNP. In one such embodiment, a prodrug of 2,3-DNP, 2,4-DNP, 2,5-DNP, 2,6-DNP, 3,4-DNP, or 3,5-DNP, as described herein, may be used at a dose range independently selected from: 20 mg/day to 800 mg/day; 20 mg/day to 750 mg/day; 20 mg/day to 700 mg/day; 20 mg/day to 600 mg/day; 20 mg/day to 700 mg/day; 20 mg/day to 600 mg/day; 20 mg/day to 500 mg/day; 30 mg/day to 800 mg/day; 30 mg/day to 700 mg/day; 30 mg/day to 600 mg/day; 30 mg/day to 500 mg/day; 30 mg/day to 400 mg/day; 30 mg/day to 360 mg/day; 30 mg/day to 300 mg/day; 30 mg/day to 250 mg/day; 30 mg/day to 200 mg/day; 30 mg/day to 150 mg/day; 30 mg/day to 100 mg/day; 35 mg/day to 360 mg/day; 40 mg/day to 300 mg/day; 50 mg/day to 250 mg/day; or 60 mg/day to 200 mg/day; 5 mg/day to 500 mg/day; 5 mg/day to 400 mg/day; 5 mg/day to 300 mg/day; 5 mg/day to 200 mg/day; 5 mg/day to 100 mg/day; 5 mg/day to 50 mg/day; 5 mg/day to 40 mg/day; or 5 mg/day to 30 mg/day. In another such embodiment, a prodrug of 2,3-DNP, 2,4-DNP, 2,5-DNP, 2,6-DNP, 3,4-DNP, or 3,5-DNP, as described herein, may be used at a dose range independently selected from: about 20 mg/day to about 800 mg/day; about 20 mg/day to about 750 mg/day; about 20 mg/day to about 700 mg/day; about 20 mg/day to about 600 mg/day; about 20 mg/day to about 700 mg/day; about 20 mg/day to about 600 mg/day; about 20 mg/day to about 500 mg/day; about 30 mg/day to about 800 mg/day; about 30 mg/day to about 700 mg/day; about 30 mg/day to about 600 mg/day; about 30 mg/day to about 500 mg/day; about 30 mg/day to about 400 mg/day; about 30 mg/day to about 360 mg/day; about 30 mg/day to about 300 mg/day; about 30 mg/day to about 250 mg/day; about 30 mg/day to about 200 mg/day; about 30 mg/day to about 150 mg/day; about 30 mg/day to about 100 mg/day; about 35 mg/day to about 360 mg/day; about 40 mg/day to about 300 mg/day; about 50 mg/day to about 250 mg/day; or about 60 mg/day to about 200 mg/day; about 5 mg/day to about 500 mg/day; about 5 mg/day to about 400 mg/day; about 5 mg/day to about 300 mg/day; about 5 mg/day to about 200 mg/day; about 5 mg/day to about 100 mg/day; about 5 mg/day to about 50 mg/day; about 5 mg/day to about 40 mg/day; or about 5 mg/day to about 30 mg/day.

Overt reactive oxygen species (ROSs) can be produced due to noise and certain ototoxic drugs that can damage the hair cells of the ear, resulting in either temporary or permanent hearing loss. Exposure to blast waves and continuous noise not only damaged the inner ear, but caused cell death in the hippocampus, suppressed neurogenesis and impaired memory function. Aging as well can manifest in mitochondrial dysfunction leading to hearing loss. It is emerging that attempts to treat hearing loss by targeting downstream issues is not very effective. In one embodiment, the compositions and methods of the invention relate to targeting oxidative stress upstream at the mitochondria that may be causative for many disorders. There have been a variety of attempts to lower cellular stress, such as administering anti-oxidants, however these drugs have limited tissue penetration into the brain and lower ROSs after they have been formed. We have observed that wildtype mice chronically treated with an extraordinarily low dose of 2, 4-dinitrophenol resulted in treated mice living longer than untreated mice. While not being bound to theory, it is postulated that DNP modulates the mitochondrial membrane potential having a significant impact at preventing ROS formation in isolated mitochondria and in the treated wildtype mice. DNP treatment 3-hours post-ischemia reduced cerebral infarct volume 40% by protecting the penumbra or "threaten tissue" and could provide similar benefits after a blast to protect inner hair cells from eminent cell death. DNP comes with the benefits of known risks as it was used 80-years ago for weight loss at high doses (~300 mg) in over 100,000 people, however shown recently in models of neurodegeneration at very low hormetic doses to improve cognition and learning. The pharmacology, which is pleiotropic, appears to provide broad neuroprotection by lowering ROS/mTOR and increasing protective factors such as cAMP, CREB, and BDNF, could be useful for treating hearing loss. Despite DNP tainted past and common incorrect dogma of being toxic, a 28-day toxicity studies was ran and demonstrated that low doses of DNP are not toxic, have at least a 10× Safety Index with no inhibition to ion channels, CYP, Caco-2, etc., and provide therapeutically striking benefits in host CNS models representing diverse indications, thereby suggesting possible merit for inner ear and central brain hearing mitochondrial dysfunction.

Chemical Synthesis:

In one embodiment, prodrugs which contain a self-cleavable spacer and a water-solubilizing moiety are synthesized, to maintain the prodrug in a soluble form in the GI tract fluids, and which will then gradually revert to the parent drug without precipitation. In some embodiments, these compounds are 1,3 diketo analogs I-22 to I-32; II-22 to II-32; III-22 to III-32; IV-22 to IV-32; V-22 to V-32; and VI-22 to VI-32 (Schemes 1-6). The increased solubility of the prodrug and the high membrane permeability of the well-dispersed parent drug will provide a higher driving force for it to be readily absorbed via the intestinal lumen. Conversion of prodrug-to-parent drug involves a chemical cleavage at the self-cleavable spacer through a unique intramolecular cyclization-elimination reaction via imide formation under physiological conditions. The conversion time is tunable by modifying the structure of the solubilizing moiety, the bond length of the spacer, the pKa of the amine group, and the pH of the medium. Although the in silico predicted bioavailability may be low, it is likely to be much higher when one takes into account the unique pH-dependent and tunable hydrolysis mechanism. Also, the generation of parent drug does not rely on enzyme action, which may be an advantage in dealing with genetic variability associated with enzymatic prodrug hydrolysis in plasma.

In other embodiments, one or more isomers of dinitrophenol, i.e., 2,3-DNP, 2,4-DNP, 2,5-DNP, 2,6-DNP, 3,4-DNP, or 3,5-DNP, and/or a broad range of 1) bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs, 2) Gemini prodrugs and 3) bioprecursor molecules, are used for treating neurodegenerative or metabolic diseases.

Synthesis of bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs may be performed; the prodrug being selected from the group consisting of:

an amino acid (AA) ester of 2,3-DNP, 2,4-DNP, 2,5-DNP, 2,6-DNP, 3,4-DNP, or 3,5-DNP (Scheme 1, Formulas I-1 to I-10; Scheme 2, Formulas II-1 to II-10; Scheme 3, Formulas III-1 to III-10; Scheme 4, Formulas IV-1 to IV-10; Scheme 5, Formulas V-1 to V-10; and Scheme 6, Formulas VI-1 to VI-10);

AA esters incorporating a methylene dioxide (a formaldehyde equivalent) spacer (Scheme 1, Formulas I-11 to I-13; Scheme 2, Formulas II-11 to II-13; Scheme 3, Formulas III-11 to III-13; Scheme 4, Formulas IV-11 to IV-13; Scheme 5, Formulas V-11 to V-13; and Scheme 6, Formulas VI-11 to VI-13);

amino carbamate 2,3-DNP, 2,4-DNP, 2,5-DNP, 2,6-DNP, 3,4-DNP, or 3,5-DNP prodrugs (Scheme 1, Formulas I-14 to I-17; Scheme 2, Formulas II-14 to II-17; Scheme 3, Formulas III-14 to III-17; Scheme 4, Formulas IV-14 to IV-17; Scheme 5, Formulas V-14 to V-17; and Scheme 6, Formulas VI-14 to VI-17);

amino carbonate 2,3-DNP, 2,4-DNP, 2,5-DNP, 2,6-DNP, 3,4-DNP, or 3,5-DNP prodrugs (Scheme 1, Formulas I-18 and I-19; Scheme 2, Formulas II-18 and II-19; Scheme 3, Formulas III-18 and III-19; Scheme 4, Formulas IV-18 and IV-19; Scheme 5, Formulas V-18 and V-19; and Scheme 6, Formulas VI-18 and VI-19);

phosphate analogs I-20, I-21, II-20, II-21, III-20, III-21, IV-20, IV-21, V-20, V-21, VI-20, and VI-21 (Schemes 1-6);

1,3 diketo analogs I-22 to I-32; II-22 to II-32; III-22 to III-32; IV-22 to IV-32; V-22 to V-32; and VI-22 to VI-32 (Schemes 1-6);

carbonate and carbamate analogs I-33 to I-39; II-33 to II-39; III-33 to III-39; IV-33 to IV-39; V-33 to V-39; and VI-33 to VI-39 (Schemes 1-6);

benzoate analogs I-40, II-40, III-40, IV-40, V-40, and VI-40 (Schemes 1-6); and combinations thereof, wherein the prodrug is represented by formulas I-VI:

Scheme 1

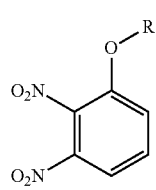

I

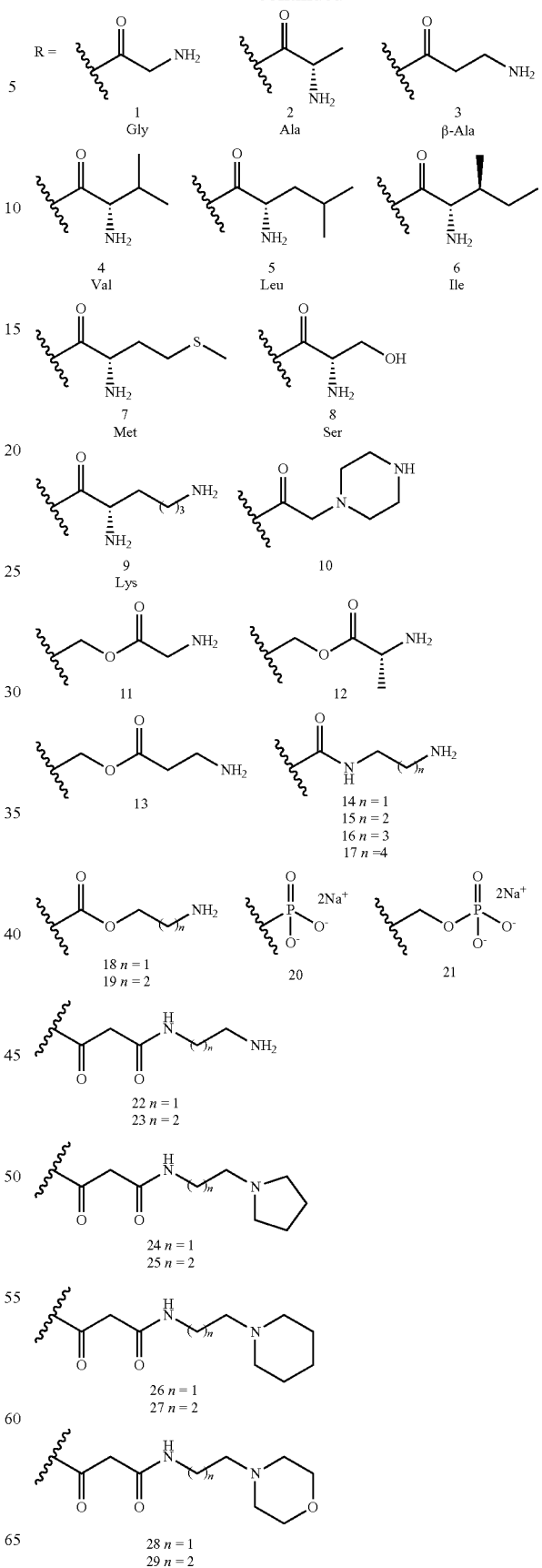

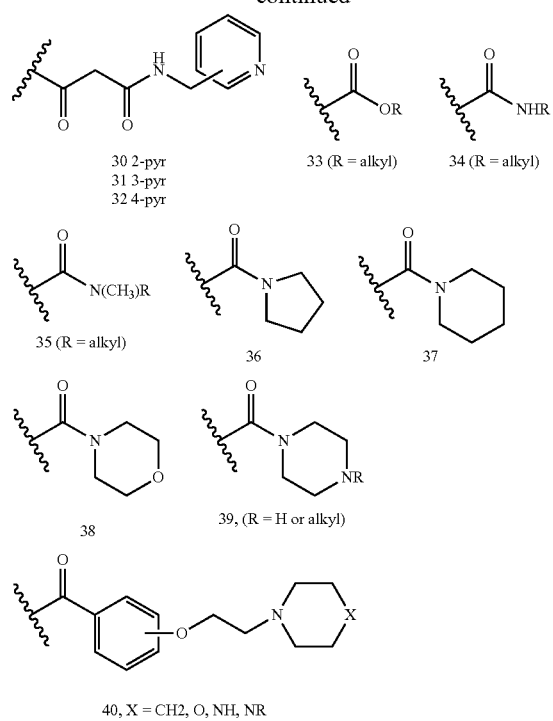
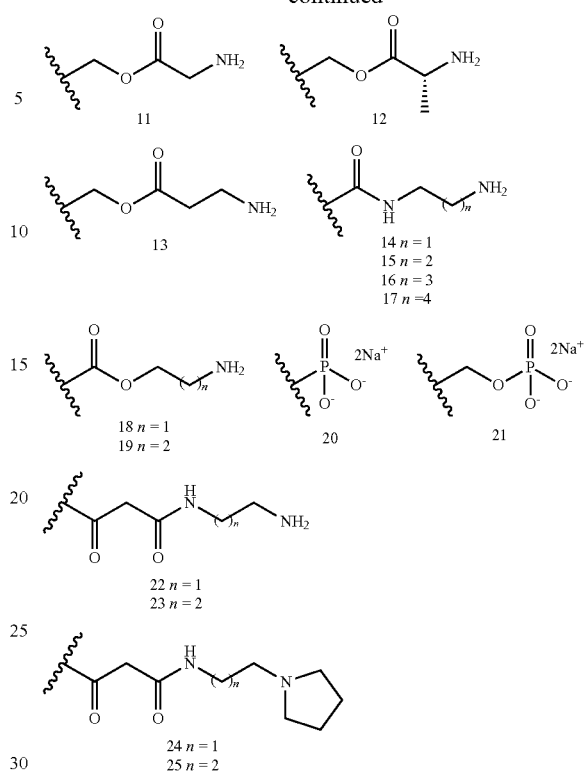
Scheme 2
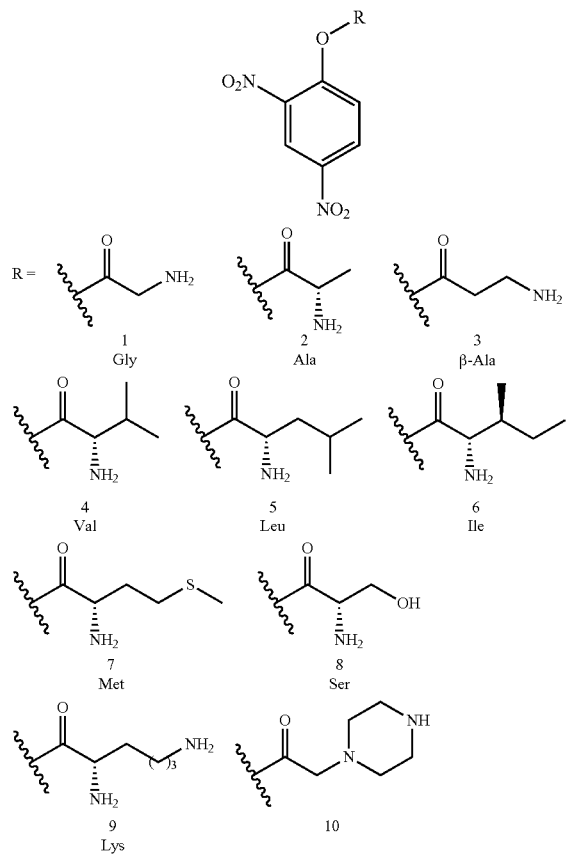
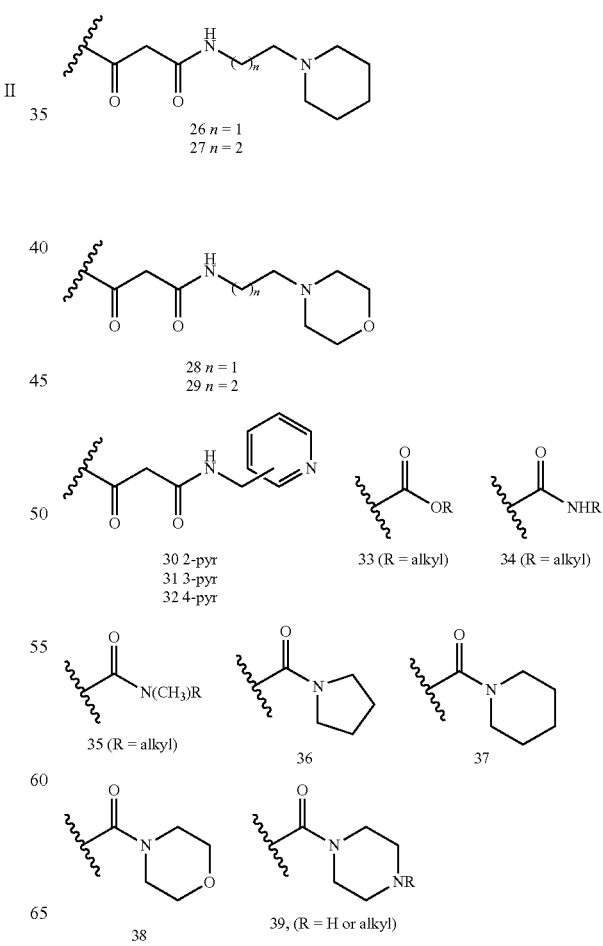

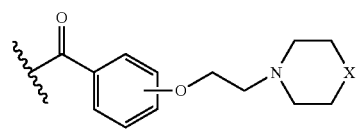
40, X = CH2, O, NH, NR
Scheme 3
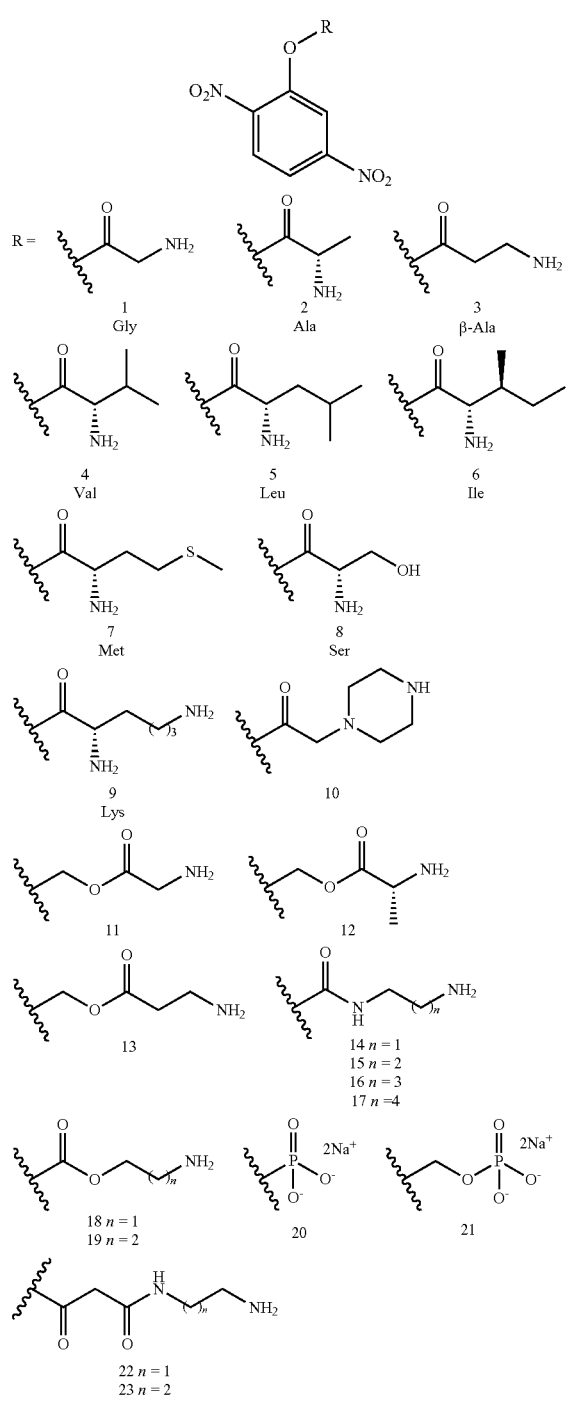
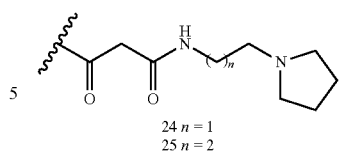
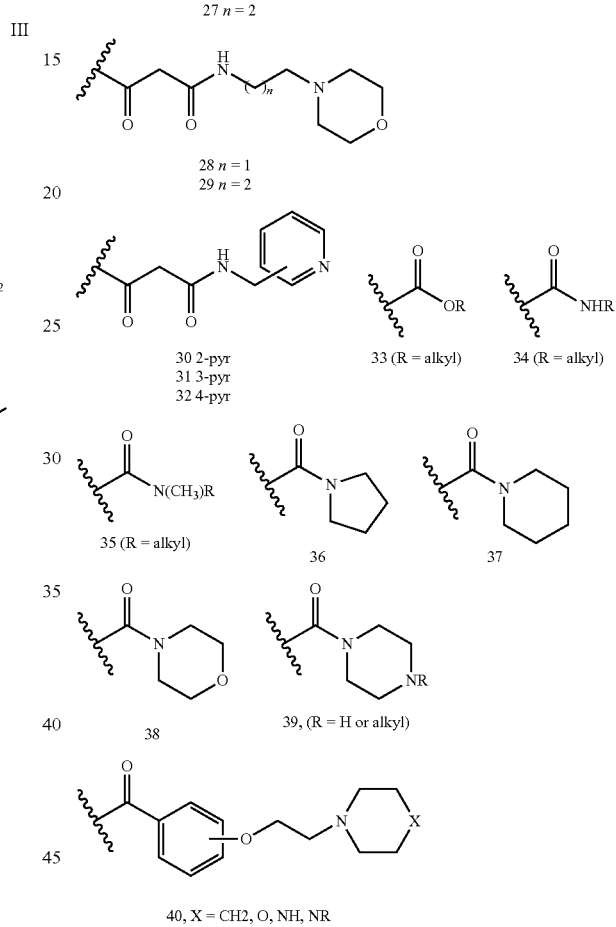
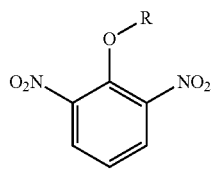
40, X = CH2, O, NH, NR
Scheme 4
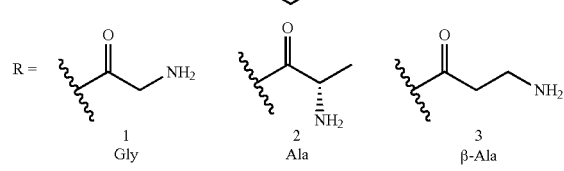

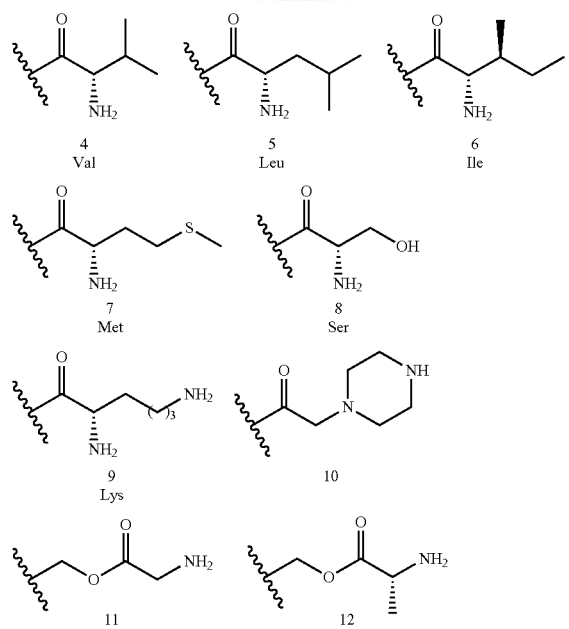
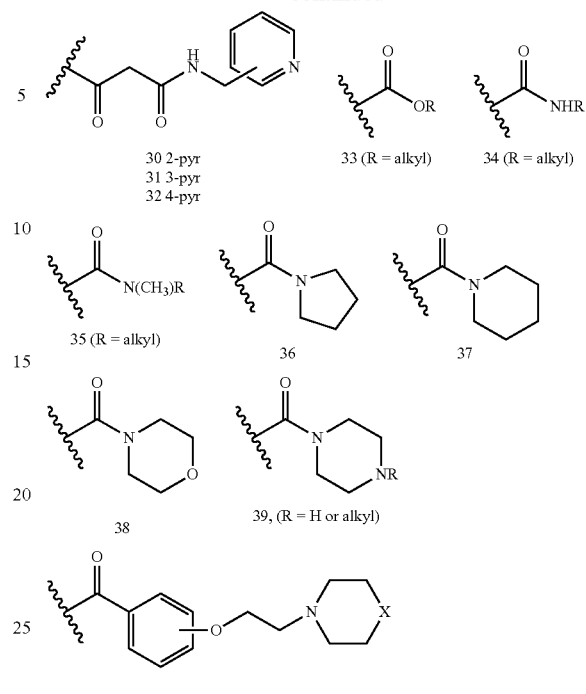
Scheme 5
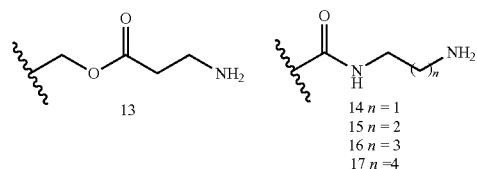
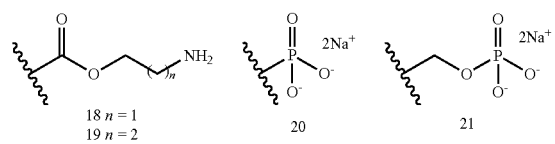
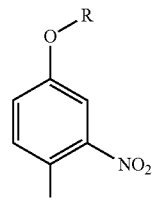
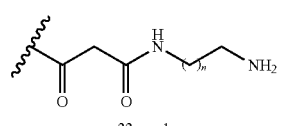
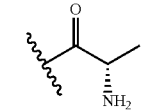
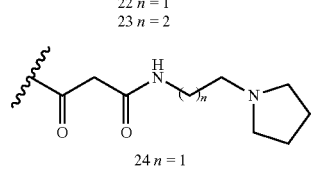
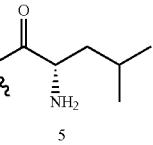
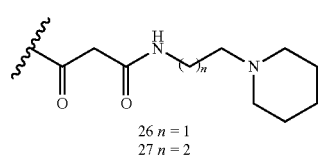
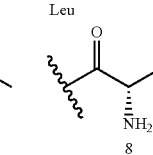
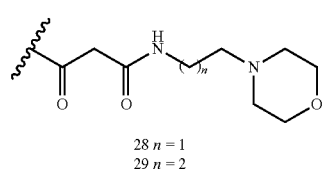
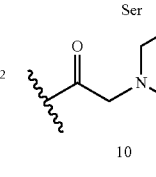

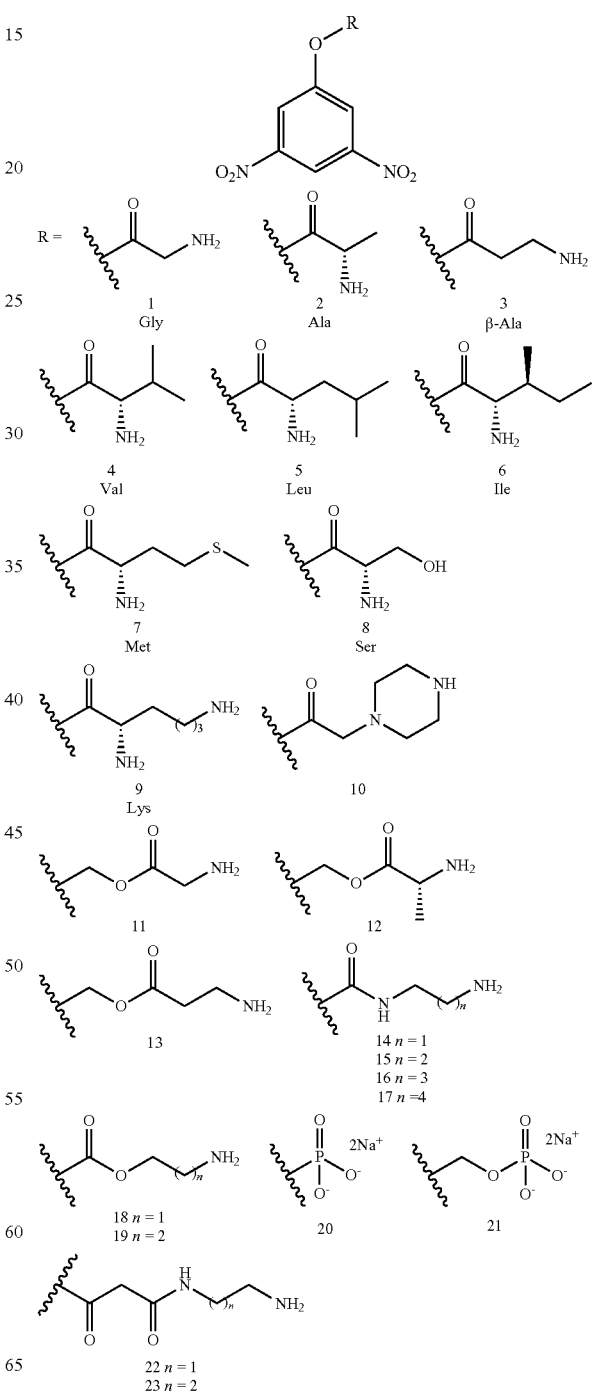

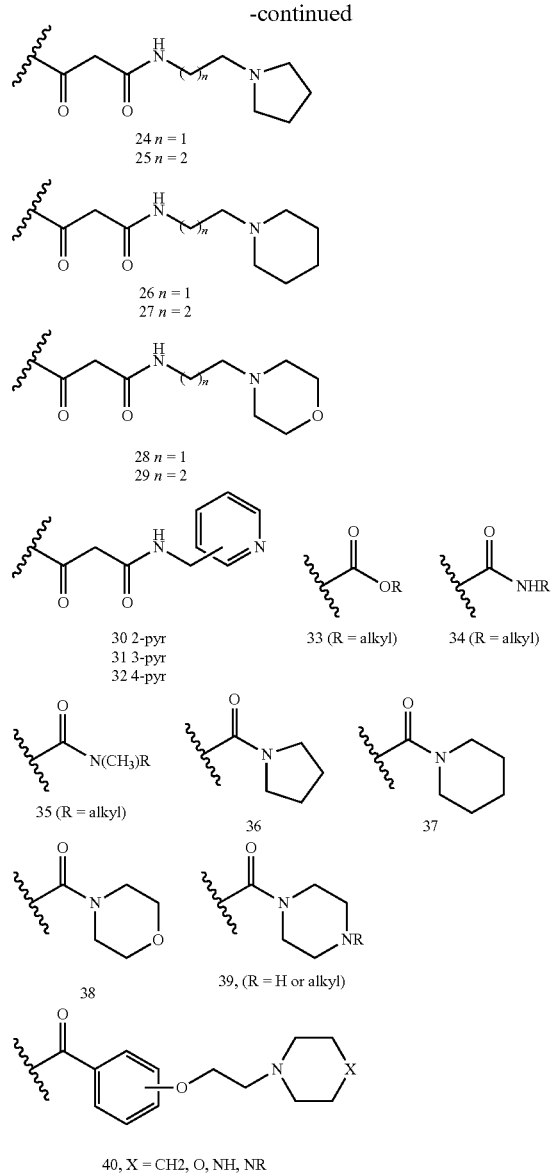

In some embodiments, a broad range of 2,3-DNP, 2,4-DNP, 2,5-DNP, 2,6-DNP, 3,4-DNP, or 3,5-DNP prodrugs can be considered. In some embodiments, the prodrugs are represented by formulas I-1 to I-40; II-1 to II-40; III-1 to III-40; IV-1 to IV-40; V-1 to V-40; and VI-1 to VI-40 are considered. A computational screen utilizing Pharma Algorithms' ADME-Tox calculator is conducted in order to identify virtual 'hits' (i.e. prodrugs with acceptable "predicted" oral bioavailabilities and water solubilities from the 32 prodrugs listed). The virtual screen allows ranking the 10 best prodrug molecules for synthesis and testing.

Amino acid (AA) esters of 2,3-DNP, 2,4-DNP, 2,5-DNP, 2,6-DNP, 3,4-DNP, or 3,5-DNP (Scheme 1, Formulas I-1 to I-10; Scheme 2, Formulas II-1 to II-10; Scheme 3, Formulas III-1 to III-10; Scheme 4, Formulas IV-1 to IV-10; Scheme 5, Formulas V-1 to V-10; and Scheme 6, Formulas VI-1 to VI-10); AA esters incorporating a methylene dioxide (a formaldehyde equivalent) spacer (Scheme 1, Formulas I-11 to I-13; Scheme 2, Formulas II-11 to II-13; Scheme 3, Formulas III-11 to III-13; Scheme 4, Formulas IV-11 to IV-13; Scheme 5, Formulas V-11 to V-13; and Scheme 6, Formulas VI-11 to VI-13); amino carbamates 2,3-DNP, 2,4-DNP, 2,5-DNP, 2,6-DNP, 3,4-DNP, or 3,5-DNP prodrugs (Scheme 1, Formulas I-14 to I-17; Scheme 2, Formulas II-14 to II-17; Scheme 3, Formulas III-14 to III-17; Scheme 4, Formulas IV-14 to IV-17; Scheme 5, Formulas V-14 to V-17; and Scheme 6, Formulas VI-14 to VI-17); amino carbonates 2,3-DNP, 2,4-DNP, 2,5-DNP, 2,6-DNP, 3,4-DNP, or 3,5-DNP prodrugs (Scheme 1, Formulas I-18 and I-19; Scheme 2, Formulas II-18 and II-19; Scheme 3, Formulas III-18 and III-19; Scheme 4, Formulas IV-18 and IV-19; Scheme 5, Formulas V-18 and V-19; and Scheme 6, Formulas VI-18 and VI-19); phosphate analogs I-20, I-21, II-20, II-21, III-20, III-21, IV-20, IV-21, V-20, V-21, VI-20, and VI-21 (Schemes 1-6); 1,3 diketo analogs I-22 to I-32; II-22 to II-32; III-22 to III-32; IV-22 to IV-32; V-22 to V-32; and VI-22 to VI-32 (Schemes 1-6); carbonate and carbamate analogs I-33 to I-39; II-33 to II-39; III-33 to III-39; IV-33 to IV-39; V-33 to V-39; and VI-33 to VI-39 (Schemes 1-6); benzoate analogs I-40, II-40, III-40, IV-40, V-40, and VI-40 (Schemes 1-6); and combinations thereof, may be considered.

Examples of ionizable amine-containing prodrugs have increased water-solubility compared to the parent compound. In addition, AA ester prodrugs have the potential to further increase oral bioavailability due to active absorption by transporters (e.g., small peptide transporter PEPT1). For example, the valine-containing prodrugs valacyclovir and valganciclovir are substrates for the enzyme PEPT1. These AA containing prodrugs are hydrolyzed to the parent drug by aminopeptidase enzymes in the brush border membrane of the GI tract. Prodrugs which can penetrate into the peripheral circulation by passive permeation and/or by active transport are hydrolyzed by various peptidase enzymes in plasma.

Two types of phosphate prodrugs of 2,3-DNP, 2,4-DNP, 2,5-DNP, 2,6-DNP, 3,4-DNP, or 3,5-DNP of formulas I-20, I-21, II-20, II-21, III-20, III-21, IV-20, IV-21, V-20, V-21, VI-20, and VI-21 (Schemes 1-6) are synthesized. According to ADME-Tox computational data, the oral bioavailability of these prodrugs can be poor, given the fact that the prediction by ADME-Tox calculator is mainly based on the physicochemical proprieties of the molecule. Since phosphoric acid is a highly polar and extensively ionized pro-moiety, phosphate prodrugs can have significantly decreased membrane permeability compared to the parent drug.

The reasons for the success of phosphate prodrugs of 2,3-DNP, 2,4-DNP, 2,5-DNP, 2,6-DNP, 3,4-DNP, or 3,5-DNP shown in formulas I-20, I-21, II-20, II-21, III-20, III-21, IV-20, IV-21, V-20, V-21, VI-20, and VI-21 (Schemes 1-6), e.g., phosphate esters as oral prodrugs, are: 1) oral absorption is not limited by dissolution-rate, since phosphate prodrugs are highly soluble in GI tract fluids; 2) phosphate esters are chemically stable enough to prevent the precipitation of the parent drug in the GI tract; 3) phosphates are rapidly hydrolyzed by membrane-bound alkaline phosphatases, which are in abundance on the brush border surface of the cells lining the small intestine, i.e., the enterocytes. Thus, the more permeable parent drug will be released, and readily cross the enterocyte membranes and enter the systemic circulation.

Scheme 8

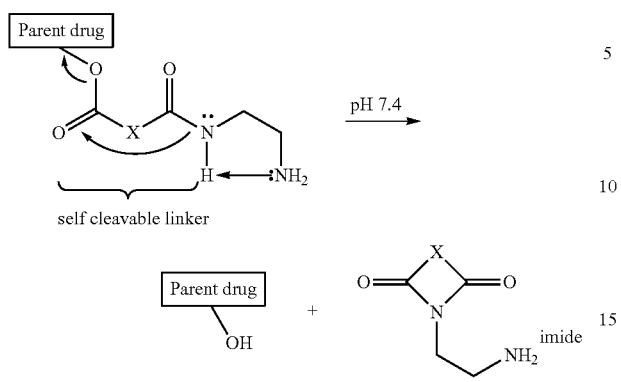

The prodrugs that are synthesized are modified to ensure water solubility. In some embodiments, acceptable solubility is tested prior to dosing in animals. If solubility is an issue, the structure of the prodrug is altered by introducing a water-soluble prodrug moiety into the molecule through conjugation with the free phenolic functionality. In other embodiments, a prodrug linker moiety that confers water-solubility properties on the prodrug molecule is utilized. In some embodiments, a solution to any water solubility issues is utilizing soft alkyl ether prodrugs that incorporate ethyleneoxy groups into promoieties such as alkyloxycarbonylmethyl (AOCOM) and N-alkyl-N-alkyloxycarbonylamino methyl (NANAOCAM) prodrugs. These prodrugs have been found to be useful for the delivery of phenolic drug molecules and have generally acceptable water solubility and membrane permeation characteristics, since they associate strongly with water molecules have good lipid solubility.

Synthesis of "Gemini" Prodrugs of 2,3-DNP, 2, 4-DNP, 2, 5-DNP, 2,6-DNP, 3, 4-DNP, or 3,5-DNP In an embodiment, 2,3-DNP, 2,4-DNP, 2,5-DNP, 2,6-DNP, 3,4-DNP, or 3,5-DNP "Gemini" prodrugs may be prepared by reacting 2,3-DNP, 2,4-DNP, 2,5-DNP, 2,6-DNP, 3,4-DNP, or 3,5-DNP with triphosgene, in the presence of $K_2CO_3$ in dichloromethane to get 2,4-dinitrophenyl carbonochloridate, which on further reaction with bases like morpholine, piperidine, piperazine, N-alkyl piperazine yields the DNP prodrugs as illustrated in Scheme 9.

Scheme 9

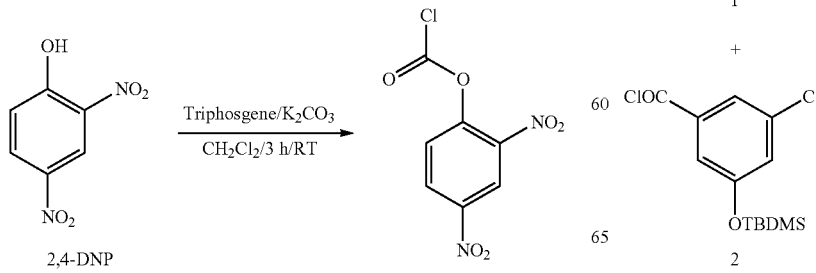

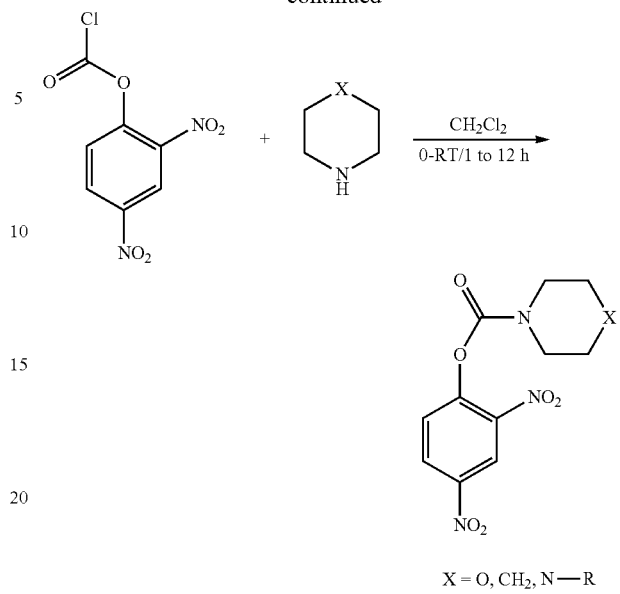

In one embodiment, 2,3-DNP, 2,4-DNP, 2,5-DNP, 2,6-DNP, 3,4-DNP, or 3,5-DNP "Gemini" prodrugs are prepared by reacting 2,3-DNP, 2,4-DNP, 2,5-DNP, 2,6-DNP, 3,4-DNP, or 3,5-DNP with 5-(tert-butyldimethylsiloxy) isophthaloyl dichloride (2) in the presence of pyridine/dichloromethane to afford precursor (3); the TBDMS protecting group will then be removed in acetone/HCl to afford prodrug (4), which will afford two equivalents of 2, 4-DNP upon hydrolysis in plasma. While the prodrug linker moiety in (4) is an ester group, other alternative linkers, such as sterically hindered ester linkers, carbonate linkers, carbamate linkers, phosphate linkers, and AOCOM and NANAOCAM based linkers may also be incorporated into the prodrug structure in order to achieve appropriate sustained release kinetics. The presence of the free phenolic group in (4) can also be utilized to improve water-solubility, if this is deemed necessary, through conjugation with appropriate hydrophilic moieties (Scheme 10).

Scheme 10

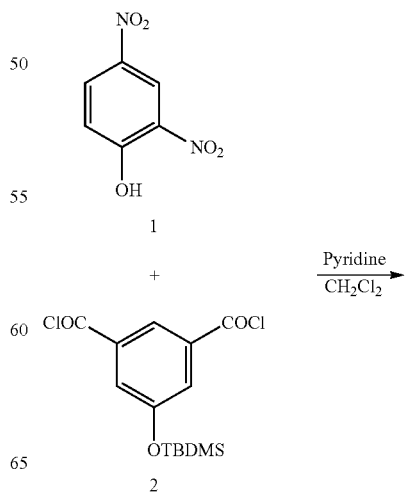

-continued

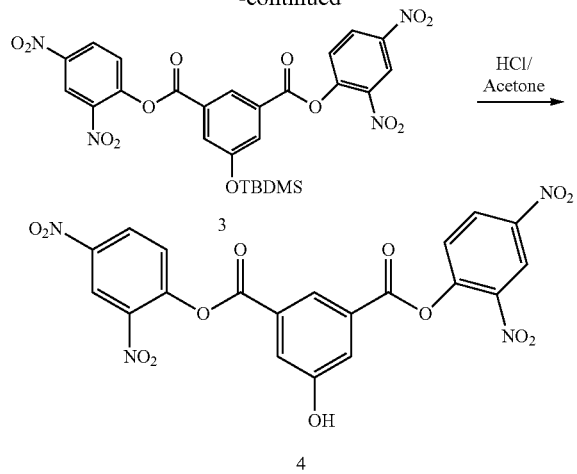

2,3-DNP, 2,4-DNP, 2,5-DNP, 2, 6-DNP, 3, 4-DNP, or 3, 5-DNP Bioprecursors

Bioprecursors of 2,3-DNP, 2,4-DNP, 2,5-DNP, 2,6-DNP, 3,4-DNP, or 3,5-DNP that may release 2,3-DNP, 2,4-DNP, 2,5-DNP, 2,6-DNP, 3,4-DNP, or 3,5-DNP after oxidative metabolism by cytochrome P-450 may be utilized. Scheme 8 shows the design of two bioprecursors that can release 2- and 4-equivalents of 2,3-DNP, 2,4-DNP, 2,5-DNP, 2,6-DNP, 3,4-DNP, or 3,5-DNP after oxidation at the benzylic carbon by Cyt P-450 (oxidation site shown by arrows). This oxidation converts the benzylic $CH_2$ group into a CO group to afford an ester moiety, which can then be cleaved by esterolysis to afford 2,3-DNP, 2,4-DNP, 2,5-DNP, 2,6-DNP, 3,4-DNP, or 3,5-DNP. The use of bioprecursors is often a good alternative to the prodrug approach and may provide metabolically activated slow release of 2, 4-DNP.

Scheme 11

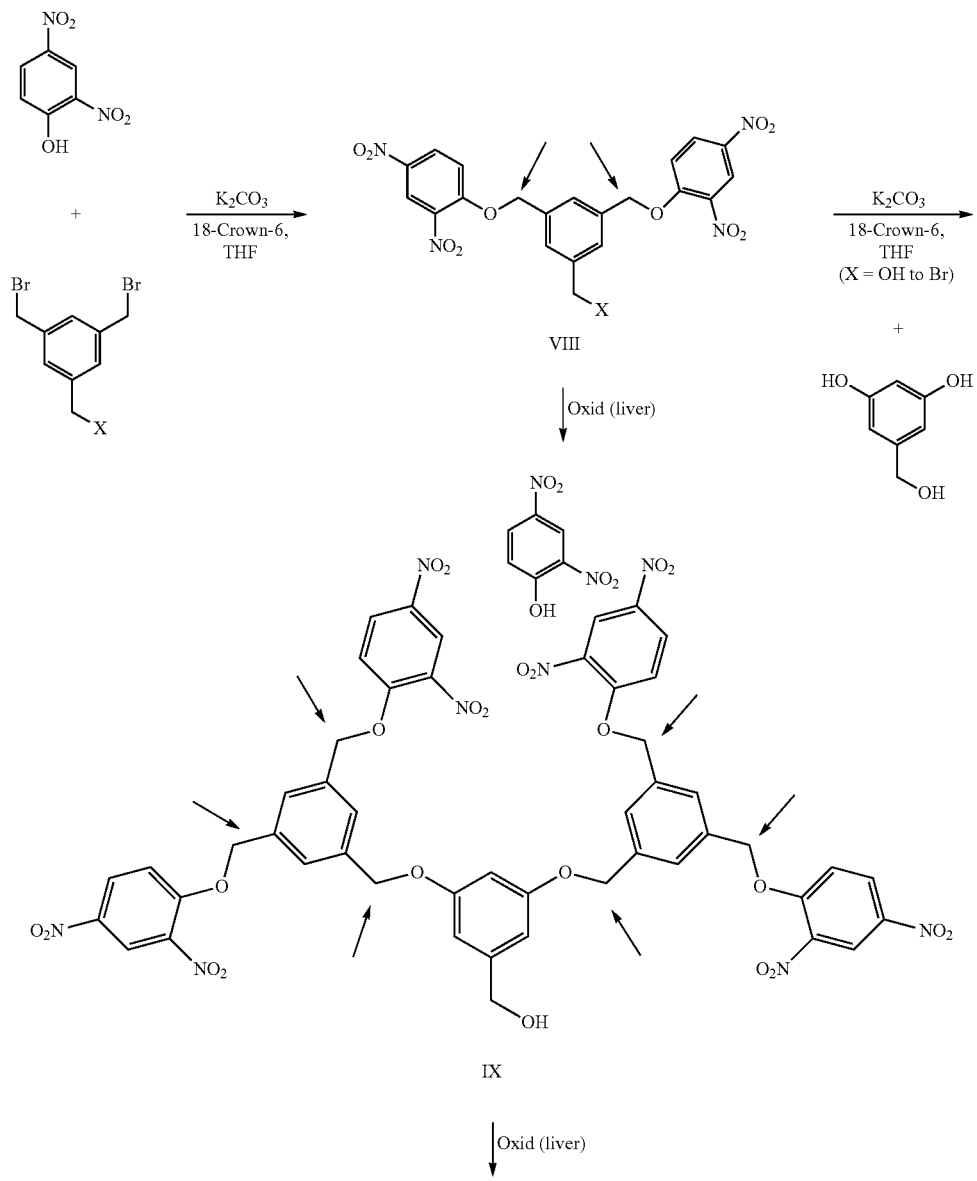

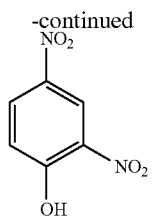

Alternative Strategies Conjugation

In some embodiments, DNP prodrugs and bioprecursors with linkers containing open functional groups are utilized, which allow conjugation of each of these entities to nanoparticles, such as dendrimers, in order to modulate the pharmacokinetics of the molecule to enable "trickle" drug delivery. Such DNP prodrugs and bioprecursors are delivered as depot nanoparticle formulations that release DNP in a slow, sustained fashion at low doses, compared to dose and release of DNP alone, to avoid possible toxicity issues.

Nanotechnology presents an opportunity to increase the bioavailability of drug particles. A decrease in particle size results in increased surface area, results in faster dissolution. In some embodiments, the decrease is by a small order of magnitude. In other embodiments, this may be enough to result in increased bioavailability. However, faster dissolution may not be sufficient to overcome exposure to acid and enzymes in the gut. Additionally, as in the case with oral insulin, this exposure may require higher dosing of the drug, resulting in unnecessary and potentially undesirable subject exposure to breakdown products as well as create significant waste.

A depot nanoparticle formulation is specially formulated to provide slow absorption of the drug from the site of administration, often keeping therapeutic levels of the drug in the patient's system for days or weeks at a time. Alternatively, a depot nanoparticle formulation may provide convenience for a patient in need of chronic medication. By delivering drug without exposure to the GI tract, the potential issue of drug degradation is avoided. Moreover, a depot nanoparticle formulation may provide better compliance due to the infrequent dosing regimen and convenience. Additional characteristics of a depot nanoparticle formulation that will enhance patient compliance are good local tolerance at the injection site and ease of administration. Good local tolerance means minimal irritation and inflammation at the site of injection; ease of administration refers to the size of needle and length of time required to administer a dose of a particular drug formulation.

In Vitro and In Vivo Evaluation of Prodrugs/Bioprecursors

The prodrugs and bioprecursors of the invention encounter a wide range of pHs and enzymes when administered orally to patients. In one embodiment, the prodrug/bioprecursor is stable in the environment of the GI tract, but releases parent drug in the plasma in a sustained manner after absorption from the GI tract. Oral dosing exposes compounds to pH 1 to 2 in the stomach, pH 4.5 at the beginning of the small intestine, pH 6.6 as an average pH for the small intestine, and pHs of 5 to 9 in the colon. Stability-indicating methods are performed in aqueous buffer solutions and simulated GI fluids to determine the resilience of the 2,3-DNP, 2,4-DNP, 2,5-DNP, 2,6-DNP, 3,4-DNP, or 3,5-DNP prodrugs/bioprecursors in the GI tract, and also their susceptibility to enzymatic conversion to the parent drug in rat plasma. These are useful methods for in vitro evaluation of the chemical stability of a prodrug candidate.

Determining pH stability in aqueous buffers (37° C., pH 1-9)
1) Determining GI stability in simulated gastric fluid (USP, 37° C.)
2) Determining GI stability in simulated intestinal fluid (USP, 37° C.)
3) Determining plasma: stability in rat plasma (37° C.)

Single compound dosing studies, are carried out on 2,3-DNP, 2,4-DNP, 2,5-DNP, 2,6-DNP, 3,4-DNP, or 3,5-DNP prodrug/bioprecursor candidates to determine their clinical potential. Most promising preclinical prodrug/bioprecursor candidates are absorbed intact from the gastrointestinal tract and are efficiently cleaved enzymatically in plasma to afford the parent drug. The presence and identification of the prodrug and the parent drug can also provide important information on the mechanism of action of 2,3-DNP, 2,4-DNP, 2,5-DNP, 2,6-DNP, 3,4-DNP, or 3,5-DNP, the identification of which is of value in the selection of new structural entities for consideration in structure-activity and structural optimization studies.

Pharmacokinetic studies are carried out on the most promising prodrug/bioprecursor candidate (i.e., the prodrug/bioprecursor that exhibits the greatest stability in the GI tract and affords sustained release of 2,3-DNP, 2,4-DNP, 2,5-DNP, 2,6-DNP, 3,4-DNP, or 3,5-DNP in vitro and in vivo in rat plasma) in the Sprague-Dawley rat. A complete PK profile is obtained for the orally administered prodrug in jugular and femoral vein catheterized rats to determine half-life ($t_{1/2}$), maximum plasma concentration ($t_{max}$), time to reach maximum plasma concentration ($t_{max}$), volume of distribution ($V_{ss}$), area under the plasma concentration versus time curve from time 0 to infinity ($AUC_{0-\infty}$), and bioavailability (F %), as well as other important PK parameters such as protein binding. LC/MS/MS is used as the analytical methodology to determine both the above pharmacokinetic parameters of the prodrug, and the plasma concentration and release kinetics of 2,3-DNP, 2,4-DNP, 2,5-DNP, 2,6-DNP, 3,4-DNP, or 3,5-DNP resulting from enzymatic conversion of the prodrug to 2,3-DNP, 2,4-DNP, 2,5-DNP, 2,6-DNP, 3,4-DNP, or 3,5-DNP in the plasma.

Although DNP is orally bioavailable, with good distribution and ~6-hour half-life in rats, the prodrug approach allows extending the plasma residence time at lower concentrations of the parent drug (DNP), by appropriate design of the prodrug release characteristics.

In an embodiment, the composition for treatment of neuromuscular, neuromuscular degenerative, neurodegenerative, autoimmune, developmental, traumatic, hearing loss related, and/or metabolic diseases is independently selected from the group consisting of 2,3-DNP, 2,4-DNP, 2,5-DNP, 2,6-DNP, 3,4-DNP, or 3,5-DNP, bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs; Gemini prodrugs, bioprecursor molecules, and combinations thereof.

In one embodiment, a dose of any of the foregoing embodiments of the compositions, of DNP, DNP prodrugs; Gemini prodrugs, bioprecursor molecules, and combinations thereof, for treatment of neuromuscular, neuromuscular degenerative, neurodegenerative, autoimmune, developmental, traumatic, hearing loss related, and/or metabolic diseases may be from about 0.01 mg/kg to about 50 mg/kg of body weight of the patient in need of treatment; from about 25 mg/kg to about 100 mg/kg of body weight of the patient in need of treatment; or from about 25 mg/kg to about 100 mg/kg of body weight of the patient in need of treatment. In one embodiment, a dose of any of the foregoing embodiments of the compositions for treatment of neuromuscular, neuromuscular degenerative, neurodegenerative, autoimmune, developmental, traumatic, hearing loss related, and/or metabolic diseases may be from 0.01 mg/kg to 50 mg/kg of body weight of the patient in need of treatment; from 25 mg/kg to 100 mg/kg of body weight of the patient in need of treatment; or from 25 mg/kg to 100 mg/kg of body weight of the patient in need of treatment. In an embodiment, the present invention relates to a pharmaceutical composition of DNP, or a pharmaceutically acceptable salt, solvate, hydrate and/or prodrug thereof as described herein, comprising a unit dose, wherein the unit dose is in the range of about 0.1 mg to about 3000 mg. In an embodiment, the present invention relates to a pharmaceutical composition of DNP, or a pharmaceutically acceptable salt, solvate, hydrate and/or prodrug thereof as described herein, comprising a unit dose, wherein the unit dose is in the range of 0.1 mg to 3000 mg.

In one embodiment, a dose of any of the foregoing embodiments of the compositions, of DNP, DNP prodrugs; Gemini prodrugs, bioprecursor molecules, and combinations thereof, for treatment of neuromuscular diseases, neuromuscular degenerative diseases, neurodegenerative diseases, autoimmune diseases, developmental diseases, traumatic diseases of CNS, hearing loss related due to aging, noise, drug induced and/or genetic hearing loss, and/or metabolic diseases, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, may be independently selected from about 0.01 mg/kg to about 50 mg/kg of body weight; about 0.01 mg/kg to about 40 mg/kg of body weight; about 0.01 mg/kg to about 30 mg/kg of body weight; about 0.01 mg/kg to about 20 mg/kg of body weight; about 0.01 mg/kg to about 10 mg/kg of body weight; about 0.01 mg/kg to about 5 mg/kg of body weight; about 0.01 mg/kg to about 1 mg/kg of body weight; about 0.05 mg/kg to about 50 mg/kg of body weight; about 0.05 mg/kg to about 40 mg/kg of body weight; about 0.05 mg/kg to about 30 mg/kg of body weight; about 0.05 mg/kg to about 20 mg/kg of body weight; about 0.05 mg/kg to about 10 mg/kg of body weight; about 0.05 mg/kg to about 1.0 mg/kg of body weight; about 0.05 mg/kg to about 0.1 mg/kg of body weight; about 0.1 mg/kg to about 40 mg/kg of body weight; about 0.1 mg/kg to about 50 mg/kg of body weight; about 0.1 mg/kg to about 30 mg/kg of body weight; about 0.1 mg/kg to about 20 mg/kg of body weight; about 0.1 mg/kg to about 15 mg/kg of body weight; about 0.1 mg/kg to about 12 mg/kg of body weight; about 0.1 mg/kg to about 10 mg/kg of body weight; about 0.1 mg/kg to about 9 mg/kg of body weight; about 0.1 mg/kg to about 8 mg/kg of body weight; about 0.1 mg/kg to about 7 mg/kg of body weight; about 0.1 mg/kg to about 6 mg/kg of body weight; about 0.1 mg/kg to about 5 mg/kg of body weight; about 0.1 mg/kg to about 4 mg/kg of body weight; about 0.1 mg/kg to about 3 mg/kg of body weight; about 0.1 mg/kg to about 2 mg/kg of body weight; 0.1 mg/kg to about 1.0 mg/kg of body weight; about 0.3 mg/kg to about 20 mg/kg of body weight; about 0.3 mg/kg to about 15 mg/kg of body weight; about 0.3 mg/kg to about 12 mg/kg of body weight; about 0.3 mg/kg to about 10 mg/kg of body weight; about 0.3 mg/kg to about 9 mg/kg of body weight; about 0.3 mg/kg to about 8 mg/kg of body weight; about 0.3 mg/kg to about 7 mg/kg of body weight; about 0.3 mg/kg to about 6 mg/kg of body weight; about 0.3 mg/kg to about 5 mg/kg of body weight; about 0.3 mg/kg to about 4 mg/kg of body weight; about 0.3 mg/kg to about 3 mg/kg of body weight; about 0.3 mg/kg to about 2 mg/kg of body weight; about 0.3 mg/kg to about 1.0 mg/kg of body weight; about 0.5 mg/kg to about 15 mg/kg of body weight; about 0.5 mg/kg to about 12 mg/kg of body weight; about 0.5 mg/kg to about 10 mg/kg of body weight; about 0.5 mg/kg to about 9 mg/kg of body weight; about 0.5 mg/kg to about 8 mg/kg of body weight; about 0.5 mg/kg to about 7 mg/kg of body weight; about 0.5 mg/kg to about 6 mg/kg of body weight; about 0.5 mg/kg to about 5 mg/kg of body weight; about 0.5 mg/kg to about 4 mg/kg of body weight; about 0.5 mg/kg to about 3 mg/kg of body weight; about 0.5 mg/kg to about 2 mg/kg of body weight; about 0.5 mg/kg to about 1.0 mg/kg of body weight; about 0.8 mg/kg to about 15 mg/kg of body weight; about 0.8 mg/kg to about 12 mg/kg of body weight; about 0.8 mg/kg to about 10 mg/kg of body weight; about 0.8 mg/kg to about 9 mg/kg of body weight; about 0.8 mg/kg to about 8 mg/kg of body weight; about 0.8 mg/kg to about 7 mg/kg of body weight; about 0.8 mg/kg to about 6 mg/kg of body weight; about 0.8 mg/kg to about 5 mg/kg of body weight; about 0.8 mg/kg to about 4 mg/kg of body weight; about 0.8 mg/kg to about 3 mg/kg of body weight; about 0.8 mg/kg to about 2 mg/kg of body weight; about 0.8 mg/kg to about 1.0 mg/kg of body weight; about 1 mg/kg to about 3.0 mg/kg of body; about 1.5 mg/kg to about 3.0 mg/kg of body; about 1.0 mg/kg to about 2.0 mg/kg of body; about 2.0 mg/kg to about 3.0 mg/kg of body; about 0.5 mg/kg to about 2.5 mg/kg of body weight; about 0.5 mg/kg to about 2.0 mg/kg of body weight.

In one embodiment, a dose of any of the foregoing embodiments of the compositions for treatment of neuromuscular diseases, neuromuscular degenerative diseases, neurodegenerative diseases, autoimmune diseases, developmental diseases, traumatic diseases of CNS, hearing loss related due to aging, noise, drug induced and/or genetic hearing loss, and/or metabolic diseases, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, may be independently selected from 0.01 mg/kg to 50 mg/kg of body weight; 0.01 mg/kg to 40 mg/kg of body weight; 0.01 mg/kg to 30 mg/kg of body weight; 0.01 mg/kg to 20 mg/kg of body weight; 0.01 mg/kg to 10 mg/kg of body weight; 0.01 mg/kg to 5 mg/kg of body weight; 0.01 mg/kg to 1 mg/kg of body weight; 0.05 mg/kg to 50 mg/kg of body weight; 0.05 mg/kg to 40 mg/kg of body weight; 0.05 mg/kg to 30 mg/kg of body weight; 0.05 mg/kg to 20 mg/kg of body weight; 0.05 mg/kg to 10 mg/kg of body weight; 0.05 mg/kg to 1.0 mg/kg of body weight; 0.05 mg/kg to 0.1 mg/kg of body weight; 0.1 mg/kg to 40 mg/kg of body weight; 0.1 mg/kg to 50 mg/kg of body weight; 0.1 mg/kg to 30 mg/kg of body weight; 0.1 mg/kg to 20 mg/kg of body weight; 0.1 mg/kg to 15 mg/kg of body weight; 0.1 mg/kg to 12 mg/kg of body weight; 0.1 mg/kg to 10 mg/kg of body weight; 0.1 mg/kg to 9 mg/kg of body weight; 0.1 mg/kg to 8 mg/kg of body weight; 0.1 mg/kg to 7 mg/kg of body weight; 0.1 mg/kg to 6 mg/kg of body weight; 0.1 mg/kg to 5 mg/kg of body weight; 0.1 mg/kg to 4 mg/kg of body weight; 0.1 mg/kg to 3 mg/kg of body weight; 0.1 mg/kg to 2 mg/kg of body weight; 0.1 mg/kg to 1.0 mg/kg of body weight; 0.3 mg/kg to 20 mg/kg of body weight; 0.3 mg/kg to 15 mg/kg of body weight; 0.3 mg/kg to 12 mg/kg of body weight; 0.3 mg/kg to 10 mg/kg of body weight; 0.3 mg/kg to 9 mg/kg of body weight; 0.3 mg/kg to 8 mg/kg of body weight; 0.3 mg/kg to 7 mg/kg of body weight; 0.3 mg/kg to 6 mg/kg of body weight; 0.3 mg/kg to 5 mg/kg of body weight; 0.3 mg/kg to 4 mg/kg of body weight; 0.3 mg/kg to 3 mg/kg of body weight; 0.3 mg/kg to 2 mg/kg of body weight; 0.3 mg/kg to 1.0 mg/kg of body weight; 0.5 mg/kg to 10 mg/kg of body weight; 0.5 mg/kg to 9 mg/kg of body weight; 0.5 mg/kg to 8 mg/kg of body weight; 0.5 mg/kg to 7 mg/kg of body weight; 0.5 mg/kg to 6 mg/kg of body weight; 0.5 mg/kg to 5 mg/kg of body weight; 0.5 mg/kg to about 4 mg/kg of body weight; 0.5 mg/kg to 3 mg/kg of body weight; 0.5 mg/kg to 2 mg/kg of body weight; 0.5 mg/kg to 1.0 mg/kg of body weight; 0.8 mg/kg to 15 mg/kg of body weight; 0.8 mg/kg to 12 mg/kg of body weight; 0.8 mg/kg to 8 10 mg/kg of body weight; 0.8 mg/kg to 9 mg/kg of body weight; 0.8 mg/kg to 8 mg/kg of body weight; 0.8 mg/kg to 7 mg/kg of body weight; 0.8 mg/kg to 6 mg/kg of body weight; 0.8 mg/kg to 5 mg/kg of body weight; 0.8 mg/kg to 4 mg/kg of body weight; 0.8 mg/kg to 3 mg/kg of body weight; 0.8 mg/kg to 2 mg/kg of body weight; 0.8 mg/kg to 1.0 mg/kg of body weight; 1 mg/kg to 3.0 mg/kg of body; 1.5 mg/kg to 3.0 mg/kg of body; 1.0 mg/kg to 2.0 mg/kg of body; 2.0 mg/kg to 3.0 mg/kg of body; 0.5 mg/kg to 2.5 mg/kg of body weight; 0.5 mg/kg to 2.0 mg/kg of body weight.

In one embodiment, a dose of any of the foregoing embodiments of the compositions for treatment of neuromuscular diseases, neuromuscular degenerative diseases, neurodegenerative diseases, autoimmune diseases, developmental diseases, traumatic diseases of CNS, hearing loss related due to aging, noise, drug induced and/or genetic hearing loss, and/or metabolic diseases, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, may be independently from about 1 mg/day/70 kg of body weight to about 300 mg/day/70 kg of body weight of the patient in need of treatment; about 1 mg/day/70 kg of body weight to about 200 mg/day/70 kg of body weight of the patient in need of treatment; about 1 mg/day/70 kg of body weight to about 100 mg/day/70 kg of body weight of the patient in need of treatment; about 1 mg/day/70 kg of body weight to about 50 mg/day/70 kg of body weight of the patient in need of treatment; about 1 mg/day/70 kg of body weight to about 30 mg/day/70 kg of body weight of the patient in need of treatment; about 1 mg/day/70 kg of body weight to about 20 mg/day/70 kg of body weight of the patient in need of treatment; about 1 mg/day/70 kg of body weight to about 10 mg/day/70 kg of body weight of the patient in need of treatment; about 1 mg/day/70 kg of body weight to about 5 mg/day/70 kg of body weight of the patient in need of treatment.

In one embodiment, a dose of any of the foregoing embodiments of the compositions for treatment of neuromuscular diseases, neuromuscular degenerative diseases, neurodegenerative diseases, autoimmune diseases, developmental diseases, traumatic diseases of CNS, hearing loss related due to aging, noise, drug induced and/or genetic hearing loss, and/or metabolic diseases, including spinal muscular atrophy (SMA) syndrome (SMA1, SMA2, SMA3, and SMA4, also called Type I, II, III and IV), traumatic brain injury (TBI), concussion, keratoconjunctivitis sicca (Dry Eye Disease), glaucoma, Sjogren's syndrome, rheumatoid arthritis, post-LASIK surgery, anti-depressants use, Wolfram Syndrome, and Wolcott-Rallison syndrome, may be independently from 1 mg/day/70 kg of body weight to 300 mg/day/70 kg of body weight of the patient in need of treatment; 1 mg/day/70 kg of body weight to 200 mg/day/70 kg of body weight of the patient in need of treatment; 1 mg/day/70 kg of body weight to 100 mg/day/70 kg of body weight of the patient in need of treatment; 1 mg/day/70 kg of body weight to 50 mg/day/70 kg of body weight of the patient in need of treatment; 1 mg/day/70 kg of body weight to 30 mg/day/70 kg of body weight of the patient in need of treatment; 1 mg/day/70 kg of body weight to 20 mg/day/70 kg of body weight of the patient in need of treatment; 1 mg/day/70 kg of body weight to 10 mg/day/70 kg of body weight of the patient in need of treatment; 1 mg/day/70 kg of body weight to 5 mg/day/70 kg of body weight of the patient in need of treatment.

In some embodiments, a pharmaceutical composition includes DNP, selected from the group consisting of DNP, 2,3-DNP, 2,4-DNP, 2,5-DNP, 2,6-DNP, 3,4-DNP, or 3,5-DNP, bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs or a pharmaceutically acceptable salt, solvate, or hydrate thereof, comprising a unit dose, independently selected from: wherein the unit dose is in the range of about 0.1 mg to about 3000 mg; wherein the unit dose is in the range of about 0.1 mg to about 1000 mg; wherein the unit dose is in the range of about 0.1 mg to about 500 mg; wherein the unit dose is in the range of about 0.1 mg to about 100 mg; wherein the unit dose is in the range of about 1 mg to about 50 mg; wherein the unit dose is about 1 mg; wherein the unit dose is about 2 mg; wherein the unit dose is about 3 mg; wherein the unit dose is about 4 mg; wherein the unit dose is about 5 mg; wherein the unit dose is the range of about 5 mg to about 10 mg; wherein the unit dose is about 6 mg; wherein the unit dose is about 7 mg; wherein the unit dose is about 8 mg; wherein the unit dose is about 9 mg; wherein the unit dose is about 10 mg; wherein the unit dose is the range of about 10 mg to about 15 mg; wherein the unit dose is about 11 mg; wherein the unit dose is about 12 mg; wherein the unit dose is about 13 mg; wherein the unit dose is about 14 mg; wherein the unit dose is about 15 mg; wherein the unit dose is the range of about 15 mg to about 20 mg; wherein the unit dose is about 16 mg; wherein the unit dose is about 17 mg; wherein the unit dose is about 18 mg; wherein the unit dose is about 19 mg; wherein the unit dose is about 20 mg; wherein the unit dose is the range of about 20 mg to about 30 mg; wherein the unit dose is about 25 mg; wherein the unit dose is about 30 mg; wherein the unit dose is the range of about 30 mg to about 40 mg; wherein the unit dose is about 35 mg; wherein the unit dose is about 40 mg; wherein the unit dose is the range of about 40 mg to about 50 mg; wherein the unit dose is about 45 mg; wherein the unit dose is about 50 mg; wherein the unit dose is the range of about 50 mg to about 100 mg;

wherein the unit dose is about 75 mg; wherein the unit dose is about 100 mg; wherein the unit dose is the range of about 100 mg to about 200 mg; wherein the unit dose is about 150 mg; wherein the unit dose is about 200 mg; wherein the unit dose is the range of about 200 mg to about 300 mg; wherein the unit dose is about 200 mg; wherein the unit dose is about 250 mg; wherein the unit dose is about 300 mg; wherein the unit dose is about 350 mg; wherein the unit dose is about 400 mg; wherein the unit dose is about 450 mg; wherein the unit dose is about 500 mg; wherein the unit dose is about 750 mg; wherein the unit dose is about 1000 mg; wherein the unit dose is about 1500 mg; wherein the unit dose is about 2000 mg; wherein the unit dose is about 2500 mg; or wherein the unit dose is about 3000 mg.

In some embodiments, a pharmaceutical composition includes DNP, selected from the group consisting of DNP, 2,3-DNP, 2,4-DNP, 2,5-DNP, 2,6-DNP, 3,4-DNP, or 3,5-DNP, bipartite 2,3-dinitrophenol, 2,4-dinitrophenol, 2,5-dinitrophenol, 2,6-dinitrophenol, 3,4-dinitrophenol, or 3,5-dinitrophenol (2,3-DNP, 2,4-DNP, 2,5-DNP, 2,6-DNP, 3,4-DNP, or 3,5-DNP) prodrugs or a pharmaceutically acceptable salt, solvate, or hydrate thereof, comprising a unit dose, independently selected from: wherein the unit dose is from the range of 0.1 mg to 3000 mg; wherein the unit dose is in the range of 0.1 mg to 1000 mg; wherein the unit dose is in the range of 0.1 mg to 500 mg; wherein the unit dose is in the range of 0.1 mg to 1000 mg; wherein the unit dose is in the range of 0.1 mg to 500 mg; wherein the unit dose is in the range of 0.1 mg to 100 mg; wherein the unit dose is in the range of 1 mg to 50 mg; wherein the unit dose is 1 mg; wherein the unit dose is 2 mg; wherein the unit dose is 3 mg; wherein the unit dose is 4 mg; wherein the unit dose is 5 mg; wherein the unit dose is the range of 5 mg to 10 mg; wherein the unit dose is 6 mg; wherein the unit dose is 7 mg; wherein the unit dose is 8 mg; wherein the unit dose is 9 mg; wherein the unit dose is 10 mg; wherein the unit dose is the range of 10 mg to 15 mg; wherein the unit dose is 11 mg; wherein the unit dose is 12 mg; wherein the unit dose is 13 mg; wherein the unit dose is 14 mg; wherein the unit dose is 15 mg; wherein the unit dose is the range of 15 mg to 20 mg; wherein the unit dose is 16 mg; wherein the unit dose is 17 mg; wherein the unit dose is 18 mg; wherein the unit dose is 19 mg; wherein the unit dose is 20 mg; wherein the unit dose is the range of 20 mg to 30 mg; wherein the unit dose is 25 mg; wherein the unit dose is 30 mg; wherein the unit dose is the range of 30 mg to 40 mg; wherein the unit dose is 35 mg; wherein the unit dose is 40 mg; wherein the unit dose is the range of 40 mg to 50 mg; wherein the unit dose is 45 mg; wherein the unit dose is 50 mg; wherein the unit dose is the range of 50 mg to 100 mg; wherein the unit dose is 75 mg; wherein the unit dose is 100 mg; wherein the unit dose is the range of 100 mg to 200 mg; wherein the unit dose is 150 mg; wherein the unit dose is 200 mg; wherein the unit dose is the range of 200 mg to 300 mg; wherein the unit dose is 200 mg; wherein the unit dose is 250 mg; wherein the unit dose is 300 mg; wherein the unit dose is 350 mg; wherein the unit dose is 400 mg; wherein the unit dose is 450 mg; wherein the unit dose is 500 mg; wherein the unit dose is 750 mg; wherein the unit dose is 1000 mg; wherein the unit dose is 1500 mg; wherein the unit dose is 2000 mg; wherein the unit dose is 2500 mg; or wherein the unit dose is 3000 mg.

In some embodiments of the foregoing embodiments of the composition for treatment of a disease, the unit dose is an immediate release formation. In some embodiments of the foregoing embodiments of the composition for treatment of a disease, the unit dose is an extended release formation. In some embodiments of the foregoing embodiments of the composition for treatment of a disease, the unit dose is a sustained release formation. In some embodiments of the foregoing embodiments of the composition for treatment of a disease, the unit dose is a controlled release formation. In some embodiments of the foregoing embodiments of the composition for treatment of a disease, the unit dose is an oral dosage form. In some embodiments, the oral dosage form is a tablet. In some embodiments of the foregoing embodiments of the composition for treatment of a disease, the oral dosage form is a capsule. In some embodiments of the foregoing embodiments of the composition for treatment of a disease, the unit dose is a capsule with no filler. In some embodiments of the foregoing embodiments of the composition for treatment of a disease, the oral dosage form is rapidly dissolving. In each of the foregoing embodiments, the disease may be independently selected from Traumatic Brain Injury (TBI), Concussion, Ischemic stroke, Huntington's disease (Adult-onset Huntington's, Juvenile Huntington's disease), Epilepsy (Cluster Seizures, Refractory Seizures, Atypical Absence Seizures, Atonic Seizures, Clonic Seizures, myoclonic seizures, tonic seizures, Tonic-Clonic Seizures, Simple Partial Seizures, Complex Partial Seizures, Secondary Generalized Seizures, Febrile Seizures, Nonepileptic Seizures, Gelastic and Dacrystic Seizures, and Absence Seizures), Multiple Sclerosis (MS) (relapse-remitting multiple sclerosis (RRMS), Secondary-progressive MS (SPMS), Primary-progressive MS (PPMS), and Progressive-relapsing MS (PRMS)), Lupus (Systemic Lupus Erythematosus (SLE), discoid (cutaneous), drug-induced lupus (dil) and neonatal lupus), Diabetes mellitus (Type-1 Diabetes, Type-2 Diabetes, Maturity Onset Diabetes of the Young (MODY: MODY1, MODY2, MODY3, MODY4, MODY5, MODY6, MODY7, MODY8, MODY9, MODY10, MODY11)), Nonalcoholic Steatohepatitis (NASH), Schizophrenia (Paranoid schizophrenia, Disorganized schizophrenia, Catatonic schizophrenia, Residual schizophrenia, Schizoaffective disorder), Myasthenia gravis (MG) (ocular myasthenia gravis, Congenital MG and generalized myasthenia gravis), rheumatoid arthritis (RA), Graves' disease, Guillain-Barré syndrome (GBS), Muscular Dystrophy (Duchenne Muscular Dystrophy (DMD), Becker, Myotonic, Congenital, Emery-Dreifuss, Facioscapulohumeral, Limb-girdle, Distal, and Oculopharyngeal), severe burns, aging, Amyotrophic Lateral Sclerosis (ALS), Ataxia (Friedreich's Ataxia, Spinocerebellar ataxias 1 (SCA1), Spinocerebellar ataxias 2 (SCA2), Spinocerebellar ataxias 3 (SCA3), Spinocerebellar ataxias 6 (SCA6), Spinocerebellar ataxias 7 (SCAT), Spinocerebellar ataxias 11 (SCA11), Dentatorubral pallidolusyian atrophy (DRPLA) and Gluten ataxia), Batten Disease or neuronal ceroid lipofuscinoses (NCL) (infantile NCL (INCL), late infantile NCL (LINCL), juvenile NCL (JNCL) or adult NCL (ANCL)), Alzheimer's Disease (Early-onset Alzheimer's, Late-onset Alzheimer's, and Familial Alzheimer's disease (FAD)), Optic neuritis (ON), Leber's hereditary optic neuropathy (LHON), Autism Spectrum Disorders (ASD) (Asperger's Syndrome, Pervasive Developmental Disorders (PDDs), Childhood Disintegrative Disorder (CDD), and Autistic disorder), Rett syndrome, Angelman's Syndrome, Leigh disease, Prader Willi Syndrome, Fragile-X Syndrome, Depression (Major Depression, Dysthymia, Postpartum Depression, Seasonal Affective Disorder, Atypical Depression, Psychotic Depression, Bipolar Disorder, Premenstrual Dysphoric Disorder, Situational Depression), Parkinson's disease (Idiopathic Parkinson's disease, Vascular parkinsonism, Dementia with Lewy bodies, Inherited Parkinson's, Drug-induced Parkinsonism, Juvenile Parkinson's and atypical parkinsonism), Wolfram syndrome (and/or any associated conditions such as diabetes issues, hearing, vision, ataxia, neurodegeneration, etc.), spinal muscular atrophy (SMA; type I, II, III and IV), hearing loss due to noise (blast and high noise), aging related hearing loss, drug induced hearing loss, and/or genetic hearing loss, concussion, keratoconjunctivitis sicca (Dry Eye Disease), glaucoma, Sjogren's syndrome, rheumatoid arthritis, post-LASIK surgery, anti-depressants use, Wolcott-Rallison syndrome, mitochondrial diseases, developmental disorders, metabolic syndrome (increased blood pressure, high blood sugar level, excess body fat around the waist and abnormal cholesterol levels) and/or autoimmune disorders by increasing energy expenditure and/or inducing BDNF mRNA expression and protein levels with DNP treatment to reverse, slow or prevent treating neurodegenerative neuromuscular, developmental, autoimmune and/or metabolic diseases and/or muscle wasting.

In one embodiment, the invention provides for a method of treatment of traumatic brain injury (TBI) using embodiments of the compositions and dosages described herein. In one embodiment, the invention relates to a method of treatment of concussion using embodiments of the compositions and dosages described herein. In one embodiment, the invention relates to a method of treatment of ischemic stroke using embodiments of the compositions and dosages described herein. In one embodiment, the invention relates to a method of treatment of severe burns using embodiments of the compositions and dosages described herein.

In one embodiment, the invention relates to a method of treatment of Huntington's disease using embodiments of the compositions and dosages described herein. In one embodiment, the invention relates to a method of treatment of adult-onset Huntington's disease using embodiments of the compositions and dosages described herein. In one embodiment, the invention relates to a method of treatment of juvenile Huntington's disease using embodiments of the compositions and dosages described herein.

In one embodiment, the invention relates to a method of treatment of epilepsy using embodiments of the compositions and dosages described herein. In one embodiment, the invention relates to a method of treatment of cluster seizures using embodiments of the compositions and dosages described herein. In one embodiment, the invention relates to a method of treatment of refractory seizures using embodiments of the compositions and dosages described herein. In one embodiment, the invention relates to a method of treatment of atypical absence seizures using embodiments of the compositions and dosages described herein. In one embodiment, the invention relates to a method of treatment of atonic seizures using embodiments of the compositions and dosages described herein. In one embodiment, the invention relates to a method of treatment of clonic seizures using embodiments of the compositions and dosages described herein. In one embodiment, the invention relates to a method of treatment of myoclonic seizures using embodiments of the compositions and dosages described herein. In one embodiment, the invention relates to a method of treatment of tonic seizures using embodiments of the compositions and dosages described herein. In one embodiment, the invention relates to a method of treatment of tonic-clonic seizures using embodiments of the compositions and dosages described herein. In one embodiment, the invention relates to a method of treatment of simple partial seizures using embodiments of the compositions and dosages described herein. In one embodiment, the invention relates to a method of treatment of complex partial seizures using embodiments of the compositions and dosages described herein. In one embodiment, the invention relates to a method of treatment of secondary generalized seizures using embodiments of the compositions and dosages described herein. In one embodiment, the invention relates to a method of treatment of febrile seizures using embodiments of the compositions and dosages described herein. In one embodiment, the invention relates to a method of treatment of nonepileptic seizures using embodiments of the compositions and dosages described herein. In one embodiment, the invention relates to a method of treatment of gelastic seizures using embodiments of the compositions and dosages described herein. In one embodiment, the invention relates to a method of treatment of dacrystic seizures using embodiments of the compositions and dosages described herein. In one embodiment, the invention relates to a method of treatment of absence seizures.

In one embodiment, the invention relates to a method of treatment of multiple sclerosis (MS) using embodiments of the compositions and dosages described herein. In one embodiment, the invention relates to a method of treatment of relapse-remitting multiple sclerosis (RRMS) using embodiments of the compositions and dosages described herein. In one embodiment, the invention relates to a method of treatment of secondary-progressive MS (SPMS) using embodiments of the compositions and dosages described herein. In one embodiment, the invention relates to a method of treatment of primary-progressive MS (PPMS) using embodiments of the compositions and dosages described herein. In one embodiment, the invention relates to a method of treatment of progressive-relapsing MS (PRMS).

In one embodiment, the invention relates to a method of treatment of diabetes mellitus using embodiments of the compositions and dosages described herein. In one embodiment, the invention relates to a method of treatment of type-1 diabetes using embodiments of the compositions and dosages described herein. In one embodiment, the invention relates to a method of treatment of type-2 diabetes using embodiments of the compositions and dosages described herein. In one embodiment, the invention relates to a method of treatment of maturity onset diabetes of the young (MODY) using embodiments of the compositions and dosages described herein. In one embodiment, the invention relates to a method of treatment of MODY1 using embodiments of the compositions and dosages described herein. In one embodiment, the invention relates to a method of treatment of MODY2 using embodiments of the compositions and dosages described herein. In one embodiment, the invention relates to a method of treatment of MODY3 using embodiments of the compositions and dosages described herein. In one embodiment, the invention relates to a method of treatment of MODY4 using embodiments of the compositions and dosages described herein. In one embodiment, the invention relates to a method of treatment of MODY5 using embodiments of the compositions and dosages described herein. In one embodiment, the invention relates to a method of treatment of MODY6 using embodiments of the compositions and dosages described herein. In one embodiment, the invention relates to a method of treatment of MODY7 using embodiments of the compositions and dosages described herein. In one embodiment, the invention relates to a method of treatment of MODY8 using embodiments of the compositions and dosages described herein. In one embodiment, the invention relates to a method of treatment of MODY9 using embodiments of the compositions and dosages described herein. In one embodiment, the invention relates to a method of treatment of MODY10 using embodiments of the compositions and dosages described herein. In one embodiment, the invention relates to a method of treatment of MODY11 using embodiments of the compositions and dosages described herein.

In one embodiment, the invention relates to a method of treatment of nonalcoholic steatohepatitis (NASH) using embodiments of the compositions and dosages described herein.

In one embodiment, the invention relates to a method of treatment of muscular dystrophy using embodiments of the compositions and dosages described herein. In one such embodiment, such dosages for an adult independently ranging from: 10 mg/day to 150 mg/day; 20 mg/day to 150 mg/day; 30 mg/day to 150 mg/day; 40 mg/day to 150 mg/day; 50 mg/day to 150 mg/day; 60 mg/day to 150 mg/day; 70 mg/day to 150 mg/day; 80 mg/day to 150 mg/day; 90 mg/day to 150 mg/day; 80 mg/day to 100 mg/day; 90 mg/day to 100 mg/day; 91 mg/day to 100 mg/day 92 mg/day to 100 mg/day; 93 mg/day to 100 mg/day; 94 mg/day to 100 mg/day; or independently dosages of 90 mg/day; 91 mg/day; 92 mg/day; 93 mg/day; 94 mg/day; 95 mg/day; 96 mg/day; 97 mg/day; 98 mg/day or 99 mg/day. In one such embodiment, such dosages for an adolescent independently ranging from: 1 mg/day to 45 mg/day; 1 mg/day to 50 mg/day; 5 mg/day to 45 mg/day; 5 mg/day to 50 mg/day; 10 mg/day to 45 mg/day; 15 mg/day to 45 mg/day; 20 mg/day to 45 mg/day; 25 mg/day to 45 mg/day; 30 mg/day to 45 mg/day; 35 mg/day to 45 mg/day; 35 mg/day to 40 mg/day or; independently dosages of 35 mg/day; 35 mg/day; 37 mg/day; 38 mg/day; 39 mg/day; 40 mg/day; 41 mg/day; 42 mg/day; 43 mg/day; 44 mg/day or 45 mg/day. In another such embodiment, such dosages for an adult independently ranging from: about 10 mg/day to about 150 mg/day; about 20 mg/day to about 150 mg/day; about 30 mg/day to about 150 mg/day; about 40 mg/day to about 150 mg/day; about 50 mg/day to about 150 mg/day; about 60 mg/day to about 150 mg/day; about 70 mg/day to about 150 mg/day; about 80 mg/day to about 150 mg/day; about 90 mg/day to about 150 mg/day; about 80 mg/day to about 100 mg/day; about 90 mg/day to about 100 mg/day; about 91 mg/day to about 100 mg/day; about 92 mg/day to about 100 mg/day; about 93 mg/day to about 100 mg/day; about 94 mg/day to about 100 mg/day; or independently dosages of about 90 mg/day; about 91 mg/day; about 92 mg/day; about 93 mg/day; about 94 mg/day; about 95 mg/day; about 96 mg/day; about 97 mg/day; about 98 mg/day or about 99 mg/day. In another such embodiment, such dosages for an adolescent independently ranging from: about 1 mg/day to about 45 mg/day; about 1 mg/day to about 50 mg/day; about 5 mg/day to about 45 mg/day; about 5 mg/day to about 50 mg/day; about 10 mg/day to about 45 mg/day; about 15 mg/day to about 45 mg/day; about 20 mg/day to about 45 mg/day; about 25 mg/day to about 45 mg/day; about 30 mg/day to about 45 mg/day; about 35 mg/day to about 45 mg/day; about 35 mg/day to about 40 mg/day or; independently dosages of about 35 mg/day; about 35 mg/day; about 37 mg/day; about 38 mg/day; about 39 mg/day; about 40 mg/day; about 41 mg/day; about 42 mg/day; about 43 mg/day; about 44 mg/day or about 45 mg/day. In one embodiment, the invention relates to a method of treatment of Duchenne muscular dystrophy (DMD) using embodiments of the compositions and dosages described herein. In one embodiment, the invention relates to a method of treatment of Becker muscular dystrophy using embodiments of the compositions and dosages described herein. In one embodiment, the invention relates to a method of treatment of myotonic muscular dystrophy using embodiments of the compositions and dosages described herein. In one embodiment, the invention relates to a method of treatment of congenital muscular dystrophy using embodiments of the compositions and dosages described herein. In one embodiment, the invention relates to a method of treatment of Emery-Dreifuss muscular dystrophy using embodiments of the compositions and dosages described herein. In one embodiment, the invention relates to a method of treatment of facioscapulohumeral muscular dystrophy using embodiments of the compositions and dosages described herein. In one embodiment, the invention relates to a method of treatment of limb-girdle muscular dystrophy using embodiments of the compositions and dosages described herein. In one embodiment, the invention relates to a method of treatment of distal muscular dystrophy using embodiments of the compositions and dosages described herein. In one embodiment, the invention relates to a method of treatment of oculopharyngeal muscular dystrophy using embodiments of the compositions and dosages described herein.

In one embodiment, the invention relates to a method of treatment of amyotrophic lateral sclerosis (ALS) using embodiments of the compositions and dosages described herein. In one embodiment, the invention relates to a method of treatment of ataxia using embodiments of the compositions and dosages described herein. In one embodiment, the invention relates to a method of treatment of Friedreich's ataxia using embodiments of the compositions and dosages described herein. In one embodiment, the invention relates to a method of treatment of spinocerebellar ataxias 1 (SCA1) using embodiments of the compositions and dosages described herein. In one embodiment, the invention relates to a method of treatment of Batten disease. In one embodiment, the invention relates to a method of treatment of neuronal ceroid lipofuscinoses (NCL) using embodiments of the compositions and dosages described herein. In one embodiment, the invention relates to a method of treatment of infantile NCL (INCL) using embodiments of the compositions and dosages described herein. In one embodiment, the invention relates to a method of treatment of late infantile NCL (LINCL) using embodiments of the compositions and dosages described herein. In one embodiment, the invention relates to a method of treatment of juvenile NCL (JNCL) using embodiments of the compositions and dosages described herein. In one embodiment, the invention relates to a method of treatment of adult NCL (ANCL) using embodiments of the compositions and dosages described herein.

In one embodiment, the invention relates to a method of treatment of Alzheimer's disease using embodiments of the compositions and dosages described herein. In one such embodiment, such dosages independently ranging from: 1 mg/day to 45 mg/day; 5 mg/day to 45 mg/day; 10 mg/day to 45 mg/day; 15 mg/day to 45 mg/day; 20 mg/day to 45 mg/day; 25 mg/day to 45 mg/day; 30 mg/day to 45 mg/day; 35 mg/day to 45 mg/day; 35 mg/day to 40 mg/day or; independently dosages of 31 mg/day; 32 mg/day; 33 mg/day; 34 mg/day; 35 mg/day; 36 mg/day; 37 mg/day; 38 mg/day; 39 mg/day or 40 mg/day. In another such embodiment, such dosages independently ranging from: about 1 mg/day to about 45 mg/day; about 5 mg/day to about 45 mg/day; about 10 mg/day to about 45 mg/day; about 15 mg/day to about 45 mg/day; about 20 mg/day to about 45 mg/day; about 25 mg/day to about 45 mg/day; about 30 mg/day to about 45 mg/day; about 35 mg/day to about 45 mg/day; about 35 mg/day to about 40 mg/day or; independently dosages of about 31 mg/day; about 32 mg/day; about 33 mg/day; about 34 mg/day; about 35 mg/day; about 36 mg/day; about 37 mg/day; about 38 mg/day; about 39 mg/day or about 40 mg/day. In one embodiment, the invention relates to a method of treatment of early-onset Alzheimer's disease using embodiments of the compositions and dosages described herein. In one embodiment, the invention relates to a method of treatment of late-onset Alzheimer's disease using embodiments of the compositions and dosages described herein. In one embodiment, the invention relates to a method of treatment of familial Alzheimer's disease (FAD) using embodiments of the compositions and dosages described herein.

In one embodiment, the invention relates to a method of treatment of optic neuritis (ON) using embodiments of the compositions and dosages described herein. In one embodiment, the invention relates to a method of treatment of an autism spectrum disorder (ASD) using embodiments of the compositions and dosages described herein. In one embodiment, the invention relates to a method of treatment of Rett syndrome using embodiments of the compositions and dosages described herein. In one embodiment, the invention relates to a method of treatment of Angelman's syndrome using embodiments of the compositions and dosages described herein.

In one embodiment, the invention relates to a method of treatment of Parkinson's disease using embodiments of the compositions and dosages described herein. In one embodiment, the invention relates to a method of treatment of idiopathic Parkinson's disease using embodiments of the compositions and dosages described herein. In one embodiment, the invention relates to a method of treatment of vascular parkinsonism using embodiments of the compositions and dosages described herein. In one embodiment, the invention relates to a method of treatment of dementia with Lewy bodies using embodiments of the compositions and dosages described herein. In one embodiment, the invention relates to a method of treatment of inherited Parkinson's diseases using embodiments of the compositions and dosages described herein. In one embodiment, the invention relates to a method of treatment of drug-induced Parkinsonism using embodiments of the compositions and dosages described herein. In one embodiment, the invention relates to a method of treatment of juvenile Parkinson's disease using embodiments of the compositions and dosages described herein. In one embodiment, the invention relates to a method of treatment of atypical parkinsonism using embodiments of the compositions and dosages described herein.

In one embodiment, the invention relates to a method of treatment of Wolfram syndrome using embodiments of the compositions and dosages described herein. In one embodiment, the invention relates to a method of treatment of diabetes issues associated with Wolfram syndrome using embodiments of the compositions and dosages described herein. In one embodiment, the invention relates to a method of treatment of hearing issues associated with Wolfram syndrome using embodiments of the compositions and dosages described herein. In one embodiment, the invention relates to a method of treatment of vision issues associated with Wolfram syndrome using embodiments of the compositions and dosages described herein. In one embodiment, the invention relates to a method of treatment of ataxia associated with Wolfram syndrome using embodiments of the compositions and dosages described herein. In one embodiment, the invention relates to a method of treatment of neurodegeneration associated with Wolfram syndrome using embodiments of the compositions and dosages described herein.

In one embodiment, the invention relates to a method of treatment of spinal muscular atrophy (SMA) type III using embodiments of the compositions and dosages described herein. In one embodiment, the invention relates to a method of treatment of SMA type IV using embodiments of the compositions and dosages described herein.

In one embodiment, the invention relates to a method of treatment of hearing loss using embodiments of the compositions and dosages described herein. In one embodiment, the invention relates to a method of treatment of hearing loss due to noise using embodiments of the compositions and dosages described herein. In one embodiment, the invention relates to a method of treatment of hearing loss due to blast noise using embodiments of the compositions and dosages described herein. In one embodiment, the invention relates to a method of treatment of hearing loss due to high noise using embodiments of the compositions and dosages described herein. In one embodiment, the invention relates to a method of treatment of aging related hearing loss using embodiments of the compositions and dosages described herein. In one embodiment, the invention relates to a method of treatment of drug induced hearing loss using embodiments of the compositions and dosages described herein. In one embodiment, the invention relates to a method of treatment of genetic hearing loss using embodiments of the compositions and dosages described herein. In one embodiment, the invention relates to a method of treatment of hearing loss due to concussion using embodiments of the compositions and dosages described herein. In one embodiment, the invention relates to a method of treatment of hearing loss due to traumatic brain injury (TBI) using embodiments of the compositions and dosages described herein.

In some embodiments, the unit dose is delivered intravenously. In some embodiments, the unit dose is delivered by means of an intravenous drip along with saline. In some embodiments, the unit dose is delivered by means of an intravenous drip along with saline, other medications, vitamins and/or nourishment. In some embodiments, the unit dose is delivered subcutaneously. In some embodiments, the unit dose is delivered topically. In some embodiments, the unit dose is delivered transdermally. In some embodiments, the unit dose is in the form of a patch.

The dose may be administered as a single daily dose, a twice-daily dose, three times daily, or more frequently. The dose may be administered three times weekly, twice weekly, once weekly, or less frequently. In an embodiment, administration frequency may be between 1 and 5 times a day. In another embodiment, administration frequency may be between 2 and 4 times a day. In another embodiment, administration frequency may be at least 3 times a day. In another embodiment, administration frequency may be twice a day. In another embodiment, administration frequency may be once a day. In another embodiment, administration frequency may be less frequent than once a day. In other embodiments, administration frequency may be once every 2 days or once every 3 days or once every 4 days or once every 5 days or once every 6 days. In another embodiment, administration frequency may be once a week. In another embodiment, administration frequency may change with time, starting at a certain rate, such as once or twice a day, and then decreasing to less frequently, such as once every 2 days or once every 3 days, or once a week, after the first day of treatment. In another embodiment, administration frequency may change with time, starting at a certain rate, such as once or twice a day, and then decreasing to less frequently, such as once every 2 days or once every 3 days, or once a week, after the first two or three days of treatment. In another embodiment, administration frequency may change with time, starting at a certain rate, such as once or twice a day, and then decreasing to less frequently, such as once every 2 days or once every 3 days, or once a week, after the first week of treatment. In another embodiment, administration frequency may be on demand, as therapeutic treatment is required or desired.

It will be understood, based on the disclosure encompassed herein, how to determine whether a subject needs an additional and/or continued dose. It will also be understood that the selected dosing frequency may require an adjustment of the dosage of active ingredient. It will also be understood, based on the disclosure encompassed herein, that the selected dosage of active ingredient may require an adjustment of the dosing frequency. The disclosure encompassed herein, in combination with the skill in the art, will enable the skilled artisan to optimize both the dosage of the active ingredient and the frequency of administration of the active ingredient to treat a subject in need thereof.

The unit dose may also be adjusted based upon the size of the patient. In one embodiment, the numbers provided herein are based upon a 60 kg patient. The same therapy could be provided for a smaller or larger sized patient, by respectively reducing or increasing the dose size. By way of example only, a 20 kg child patient would need a much smaller dose than a 60 kg adult patient.

Formulation approaches are employed such as controlled release technologies (polymers, liposomes, etc.) to achieve once a day PK profile for DNP. In some embodiments, DNP prodrugs and bioprecursors with linkers containing open functional groups are synthesized, which allows conjugation of each of these entities to nanoparticles, such as dendrimers, in order to modulate the pharmacokinetics of the molecule to enable "trickle" drug delivery. Such DNP prodrugs and bioprecursors are delivered as depot nanoparticle formulation that release DNP in a slow, sustained fashion at low doses, compared to dose and release of DNP alone, to avoid possible toxicity issues. The in vitro stability, in vivo plasma release kinetics and PK profiles are evaluated. In vivo studies are carried out in Sprague-Dawley rats. LC/MS/MS is used to analyze plasma DNP released from the various prodrug-nanoparticle formulations to determine the PK profile of DNP release in the rat model.

The following examples describe the invention in further detail. These examples are provided for illustrative purposes only, and should in no way be considered as limiting the invention.

EXAMPLES

Synthesis of 2,4-Dinitrophenyl morpholine-4-carboxylate 2,4-DNP (1 mmol) reacted with triphosgene (0.5 mmol), in the presence of $K_2CO_3$ (1 mmol) in dichloromethane to get 2,4-dinitrophenyl carbonochloridate, which on further reaction with morpholine (1.1 mmol), at 0-5° C. yields the DNP-morpholine prodrug.

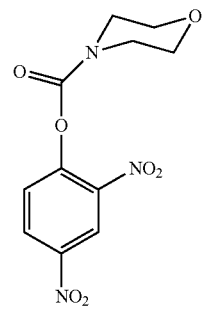 [SMILES: O=C(Oc1ccc([N+](=O)[O-])cc1[N+](=O)[O-])N1CCOCC1]

2,4-Dinitrophenyl morpholine-4-carboxylate analytical data

GC MS: M+, 297.1, HRMS: 298.0683 (M+H)+; $^1$H NMR (400 MHz, CDCl$_3$): δ 3.57-3.59 (m, 2H, CH$_2$), 3.72-3.73 (m, 2H, CH$_2$), 3.73-3.80 (m, 4H, 2×OCH$_2$), 7.53 (dd, 1H, Ar—H), 8.48-8.51 (dd, 1H, Ar—H), 8.94 (d, 1H, Ar—H) ppm. $^{13}$C NMR (75 MHz, CDCl$_3$): δ 44.99, 45.69, 66.62, 66.78, 121.94, 126.84, 129.18, 141.90, 144.85, 149.64, 151.10 ppm.

Synthesis of 2,4-dinitrophenyl piperidine-1-carboxylate 2,4-DNP (1 mmol) reacted with triphosgene (0.5 mmol), in the presence of $K_2CO_3$ (1 mmol) in dichloromethane to get 2,4-dinitrophenyl carbonochloridate, which on further reaction with piperidine (1.1 mmol), at 0-5° C. yields the DNP-morpholine prodrug.

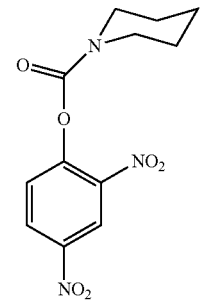 [SMILES: O=C(Oc1ccc([N+](=O)[O-])cc1[N+](=O)[O-])N1CCCCC1]

2,4-Dinitrophenyl piperidine-1-carboxylate analytical data

GC MS: M+, 295.1, $^1$H NMR (400 MHz, CDCl$_3$): δ 1.68 (m, 6H, 3×CH$_2$), 3.49-3.51 (m, 2H, CH$_2$), 3.64 (m, 2H, CH$_2$), 7.52 (d, 1H, Ar—H), 8.45 (dd, 1H, Ar—H), 8.89 (d, 1H, Ar—H) ppm. $^{13}$C NMR (75 MHz, CDCl$_3$): δ 24.05, 25.44, 25.67, 45.77, 46.67, 121.48, 126.52, 128.66, 141.73, 144.22, 149.74, 150.66 ppm.

Synthesis of 2,4-dinitrophenyl 4-methylpiperazine-1-carboxylate 2,4-DNP (1 mmol) reacted with triphosgene (0.5 mmol), in the presence of $K_2CO_3$ (1 mmol) in dichloromethane to get 2,4-dinitrophenyl carbonochloridate, which on further reaction with N-methyl piperazine (1.1 mmol), at 0-5° C. yields the DNP-N-methyl piperazine prodrug. GCMS complies: 310.26.

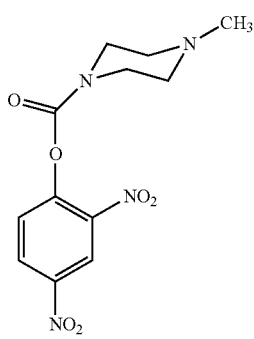 [SMILES: CN1CCN(C(=O)Oc2ccc([N+](=O)[O-])cc2[N+](=O)[O-])CC1]

Synthesis of 2,4-dinitrophenyl 4-(2-(piperidin-1-yl)ethoxy)benzoate 4-(2-(piperidin-1-yl)ethoxy)benzoic acid (1 mmol) on reflux with thionyl chloride (1.25 mmol) in dichloromethane gives its acid chloride, 4-(2-(piperidin-1-yl)ethoxy)benzoyl chloride, which on further reaction with phenol (1 mmol), in presence of triethyl amine (2.0 mmol) affords the final product of 2,4-dinitrophenyl 4-(2-(piperidin-1-yl)ethoxy) benzoate.

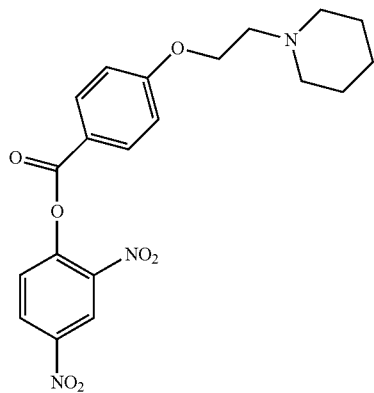 [SMILES: O=C(Oc1ccc([N+](=O)[O-])cc1[N+](=O)[O-])c1ccc(OCCN2CCCCC2)cc1]

2,4-dinitrophenyl 4-(2-(piperidin-1-yl)ethoxy)benzoate analytical data $^1$H NMR (400 MHz, CDCl$_3$); δ 1.60 (s, 2H), 1.96 (s, 4H), 3.08 (bs, 1H, 4H), 3.32 (s, 2H, N—CH$_2$), 4.56 (s, 2H, O—CH$_2$), 7.04 (d, J=8.8 Hz, 2H), 7.65 (d, J=8.8 Hz, 1H), 8.14 (d, J=8.8 Hz, 2H), 8.56-8.58 (q, J=2.4 Hz, 8.8 Hz, 1H), 8.99 (d, J=2.8 Hz, 1H) ppm. $^1$H NMR (75 MHz, CDCl$_3$); δ 22.42, 23.59, 54.48, 56.51, 64.04, 114.95, 120.59, 121.78, 126.95, 129.11, 133.23, 141.96, 145.01, 149.10, 162.91, 163.00 ppm.

Introduction: Pharmacokinetic Analysis and Bioavailability Studies of 2,4-DNP and its Prodrug II-38 in Male Sprague-Dawley Male Rats 2,4-DNP is an uncoupler organic compound biochemically active, inhibiting energy (ATP) production in cells with mitochondria. It has been used for treatment of obesity, but its abuse as a dieting agent has led to fatal severe side-effects. The factor that limits the use of increasing doses of DNP is an excessive rise in body temperature due to the heat produced during uncoupling. Accordingly, DNP overdose will cause fatal hyperthermia, with body temperature rising to a fatally high temperature leading to death. It for the later severe adverse effect, that clinical doses were slowly titrated according to patient's tolerance. Therefore, a prodrug design of 2,4-DNP with a better PK will help to deliver 2,4-DNP in lower doses into the body and prevents over dosage. The II-38 prodrug was synthesized as a drug delivery system in which the end goal was to achieve release of its parent drug (2,4-DNP) in the live plasma. This study investigates the in vitro chemical and enzymatic stability of II-38 and pharmacokinetic (PK) profile of II-38 and its parent compound (i.e., 2,4-DNP-released from II-38).

Example 1: In Vitro Chemical and Enzymatic Stability Study of II-38

To determine the stability of II-38 prodrug over the time course of 24 h in chemical buffers adjusted to pH 1.2 and 7.4 and simulated gastric fluid and simulated intestinal fluid as well as in rat and human plasma. Prodrugs encounter a wide range of pHs when administered orally to patients. Oral dosing exposes compounds to pH 1 to 2 in the stomach, pH 4.5 at the beginning of the small intestine, pH 6.6 as an average pH for the small intestine, and pH 5 to 9 in the colon. These are useful pHs for in vitro evaluation of the chemical stability of a prodrug candidate as II-38. The following experiments were performed in aqueous solutions to determine stability of the II-38 prodrug in the GI tract and susceptibility to enzymatic hydrolysis to the parent drug (2,4-DNP) in plasma:

pH: Stability in aqueous buffers (37° C., pHs 1.2 and 7.4)

GI: Stability in simulated gastric fluid (USP, 37° C.)

GI: Stability in simulated intestinal fluid (USP, 37° C.)

Plasma: Stability in rat and human plasma (37° C.)

HPLC Chromatography Conditions

HPLC analysis was carried out on an Agilent 1200 Infinity Series Quatpump, equipped with a photodiode array detector and a computer integrating apparatus. An Inertsil ODS-3 column, C18, 5 µm, 4.6×50 mm (GL Science Inc. Japan) protected with a guard column: Alltima C18, 5 µm, 4.6×7.5 mm (Grace Discovery Sciences, IL, USA) was used as the stationary phase. An isocratic method with a mobile phase consisting of water/acetonitrile (70:30) containing 0.05% formic acid in each was used. A flow rate of 0.9 mL/min was used and detection was carried out at a UV wavelength of 250 nm.

Stability of II-38 in Hydrochloric (HCl) Acid Buffer, pH 1.2

Hydrochloric acid, pH 1.2 buffer was prepared. II-38 (2.5 mg) was dissolved in 0.125 mL of DMSO (5%). Reactions were initiated by adding II-38 dissolved in DMSO slowly and gradually to a total volume of 2.375 mL of HCl buffer, pH 1.2 (Table 1) in a Franz cell diffusion chamber preheated to 37° C. The solution was mixed for 30 sec every half an hour using magnetic stirrer. Samples of 20 µL (20 µg/mL of II-38) were collected at 0, 1, 2, 4, 6 and 8 h. Each sample was mixed with acetonitrile QS to 1 mL, vortex-mixed for 30 sec and centrifuged at 10,000 rpm at room temp. A volume of 10 µL of the supernatant was injected into the HPLC spectrometer for detection of 2,4-DNP and II-38 in HCl buffer, pH 1.2.

TABLE 1

Formulation of II-38 in HCl buffer, pH 1.2.

| Weight of II-38 buffer (mL) | Total Volume PBS + DMSO (mL) | DMSO (5%) (mL) | HCl |
|---|---|---|---|
| 2.5 mg | 2.5 | 0.125 | 2.375 |

Figure 5:
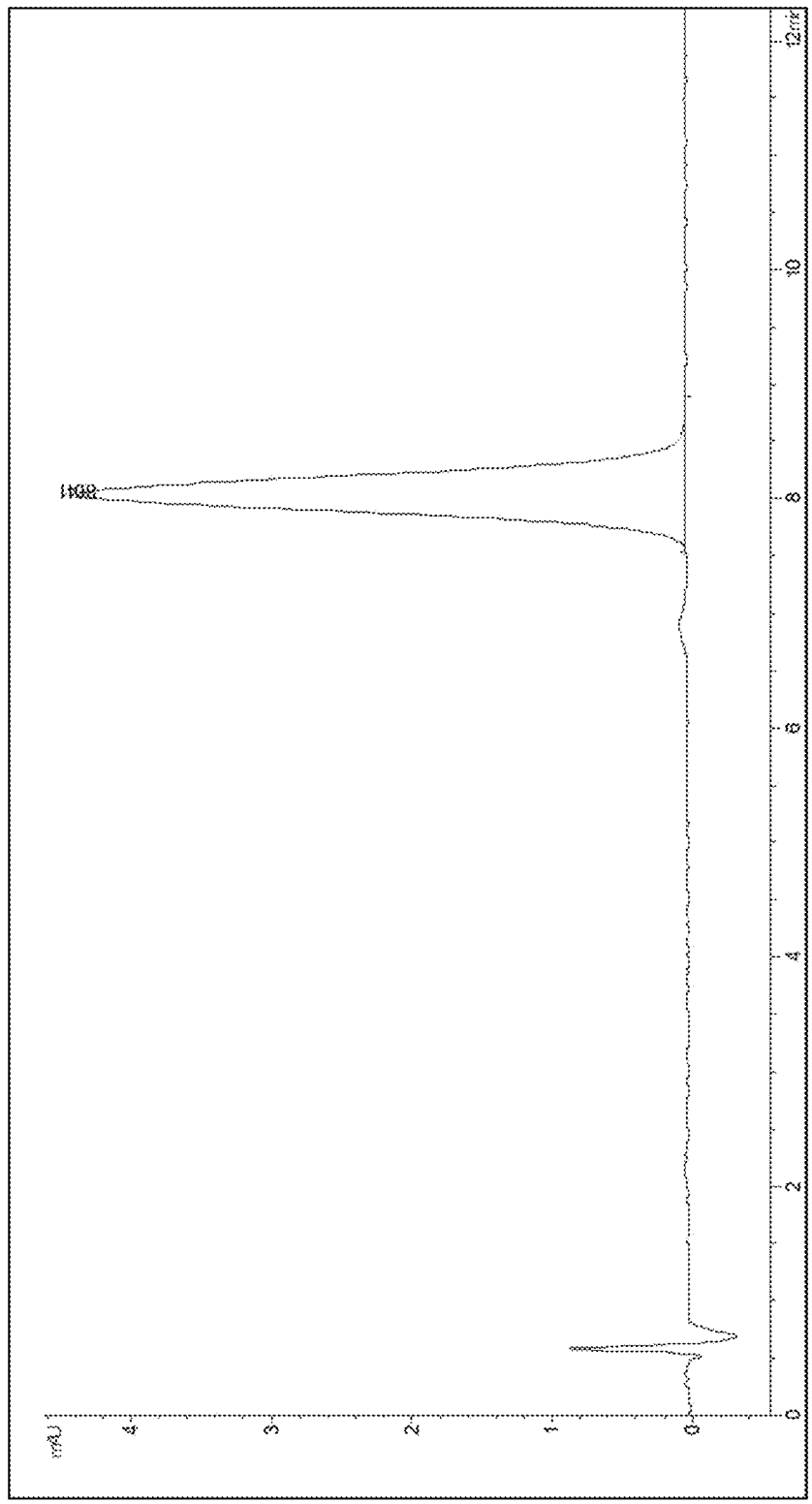
FIG. 5 illustrates a chromatogram of II-38 eluted at 8.04 min.
Figure 6:
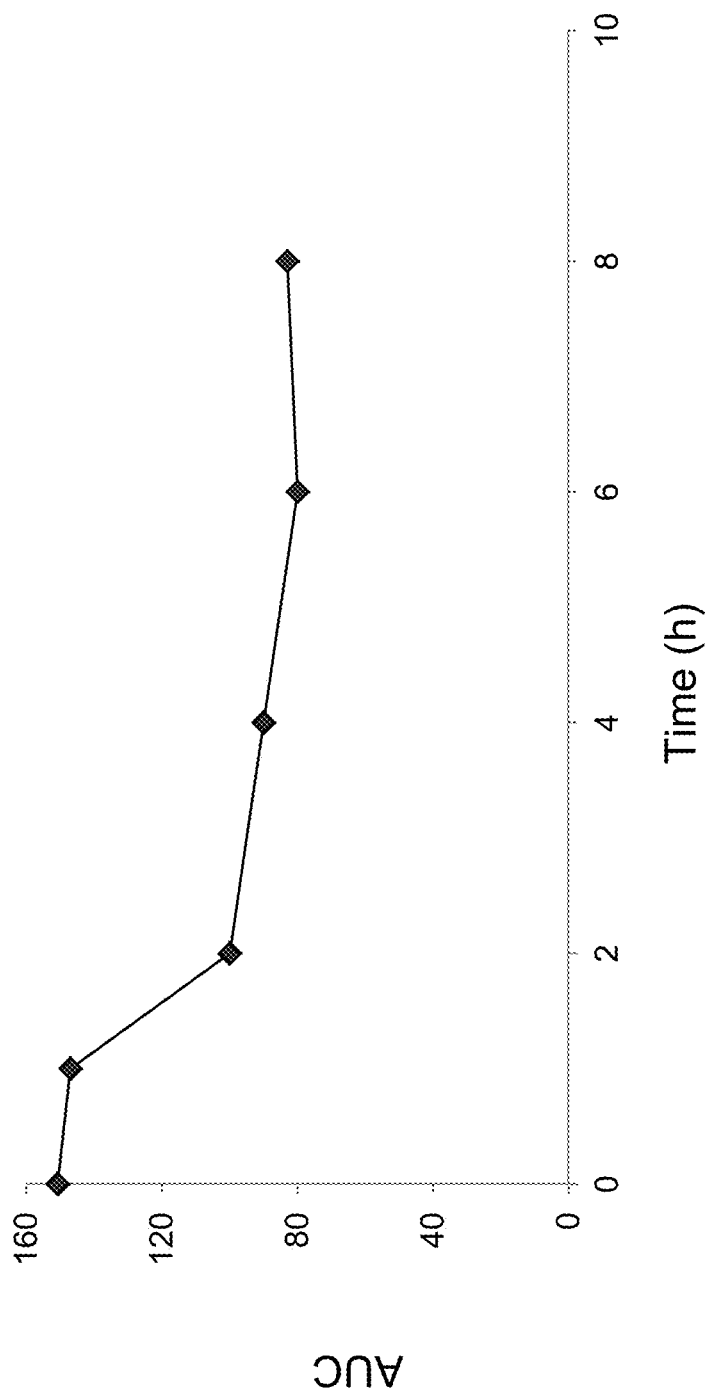
FIG. 6 illustrates the equilibrium (solubility) phase of II-38 in HCl buffer, pH 1.2.

As presented in FIG. 5, no significant hydrolysis of II-38 occurred within 8 h as indicated by a single chromatogram eluted at 8.04 min. The slope seen between 0 and 2 h represents an equilibrium (solubility) phase of II-38 in HCl buffer (FIG. 6).

Stability of II-38 in Phosphate Buffer, pH 7.4

Formulation of II-38 in phosphate buffer (PB): to formulate 1 mg/mL of II-38 in PB, 2.6 mg of II-38 was formulated in 0.13 mL of DMSO (i.e. 5%) and added slowly and gradually to a total volume of 2.47 mL of preheated PB (Table 2) in a Franz cell diffusion chamber preheated to 37° C. The solution was mixed for 30 sec every half an hour using magnetic stirrer. Samples of 20 μL (20 ug/mL of II-38) were collected at 0, 0.5, 1, 2, 4, 6 and 8 h. Each sample was mixed with acetonitrile QS to 1 mL, vortex-mixed for 30 sec and centrifuged at 10,000 rpm at room temp. A volume of 10 μL of the supernatant was injected into the HPLC spectrometer.

TABLE 2

Formulation of II-38 in PB.

| Weight of II-38 | Total Volume PBS + DMSO (mL) | DMSO (5%) (mL) | PB (mL) |
|---|---|---|---|
| 2.6 mg | 2.6 | 0.130 | 2.47 |

Figure 7:
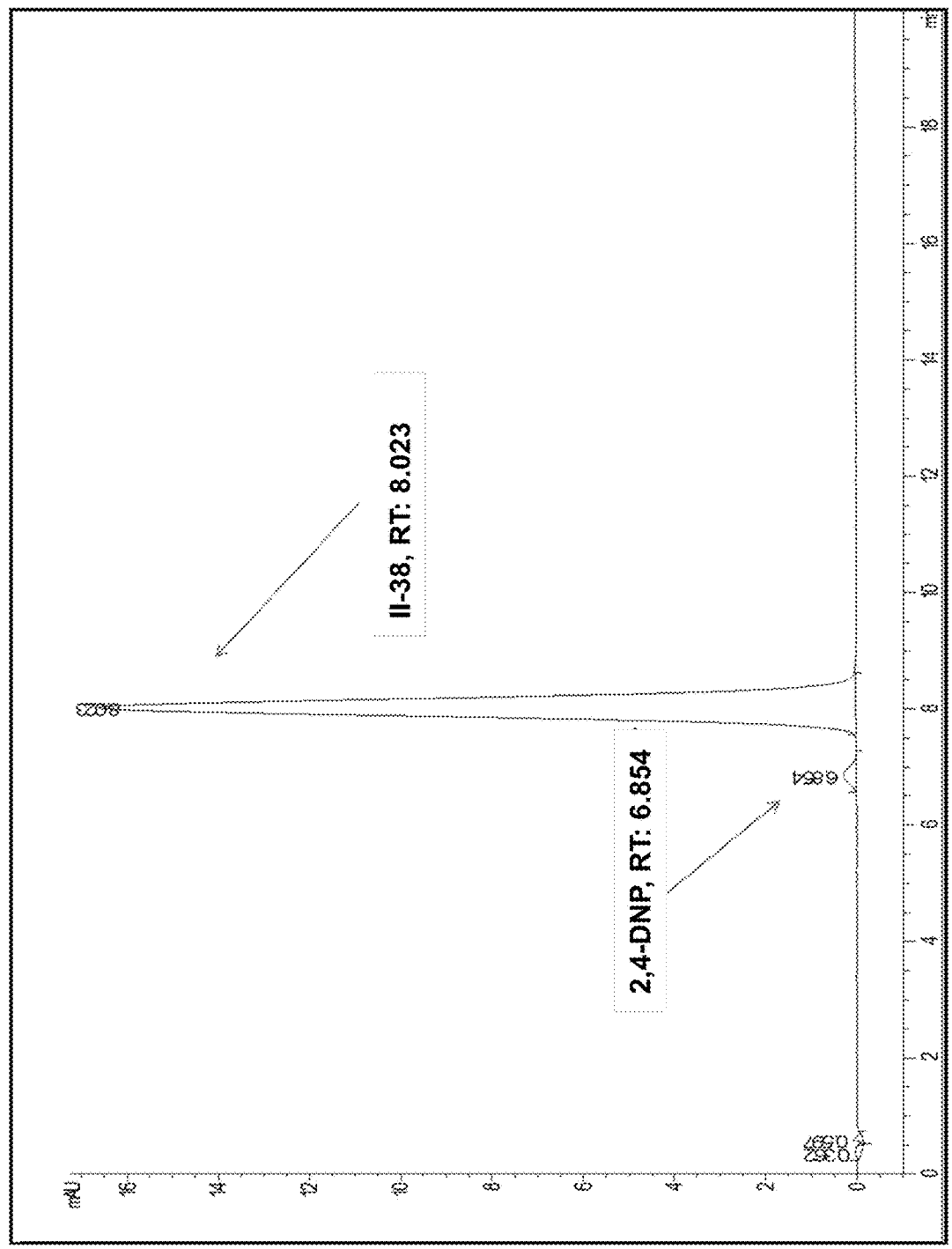
FIG. 7 illustrates chromatograms of 2,4-DNP and II-38 prodrug in phosphate buffer, pH 7.4, eluted at 6.854 and 8.023 min, respectively.
Figure 8:
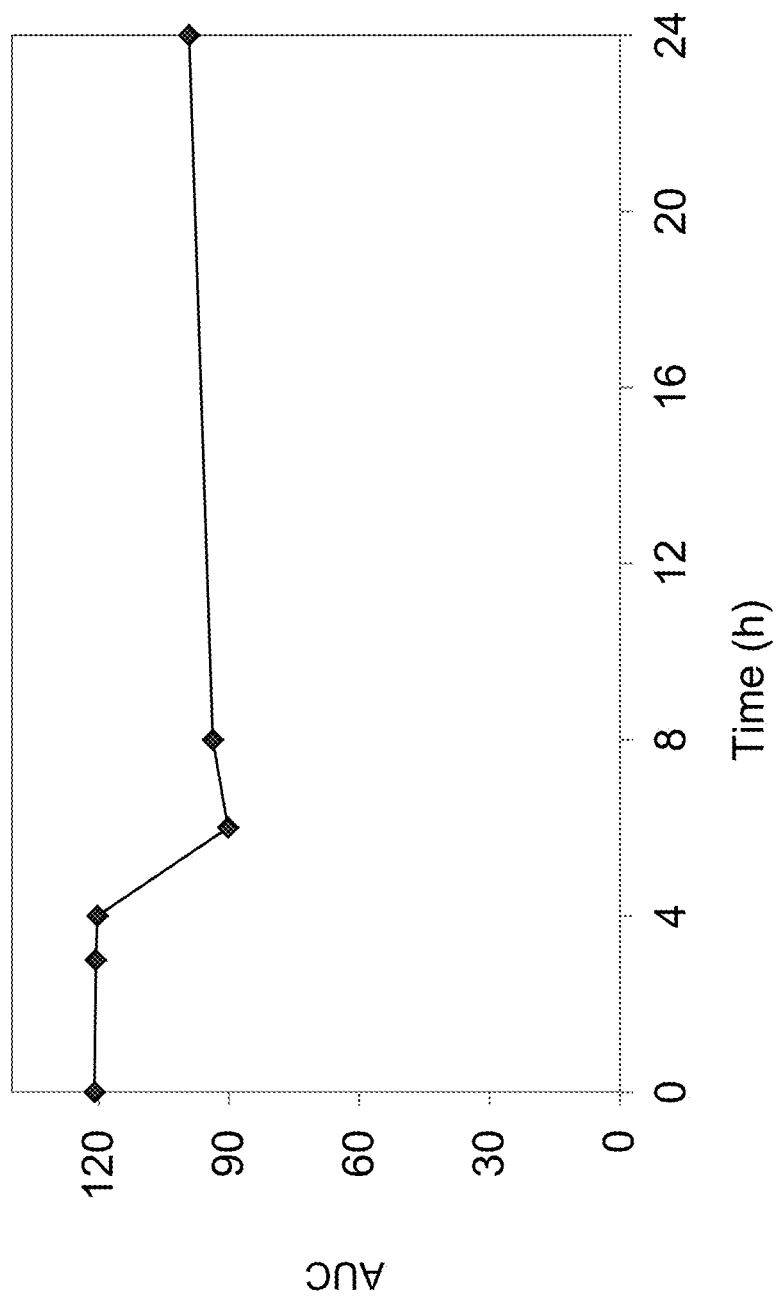
FIG. 8 illustrates the stability of II-38 in PB buffer at pH=7.4.

As presented in FIGS. 7 and 8, no significant hydrolysis of II-38 occurred within 8 h in PB as indicated by a single chromatogram eluted at 8.023 min.

Stability of II-38 in Simulated Gastric Fluid (SGF), pH 1.2

To formulate 1 mg/mL of II-38 in SGF, 3.1 mg of II-38 was dissolved in 0.155 mL of DMSO (i.e. 5%) and added slowly and gradually to a total volume of 2.945 mL of preheated SGF (Table 3) in a cell diffusion chamber preheated to 37° C. The solution was mixed for 30 sec. every half an hour using magnetic stirrer. Samples of 20 μL (20 μg/mL of II-38) were collected at 0, 1, 2, 4, 6 and 8 h. Each sample was mixed with acetonitrile QS to 1 mL, vortex-mixed for 30 sec and centrifuged at 10,000 rpm at room temp. A volume of 10 μL of the supernatant was injected into the HPLC spectrometer.

TABLE 3

Formulation of II-38 in SGF, pH 1.2.

| Weight of II-38 | Total Volume SGF + DMSO (mL) | DMSO (5%) (mL) | SGF (mL) |
|---|---|---|---|
| 3.1 mg | 3.1 | 0.155 | 2.945 |

Figure 9:
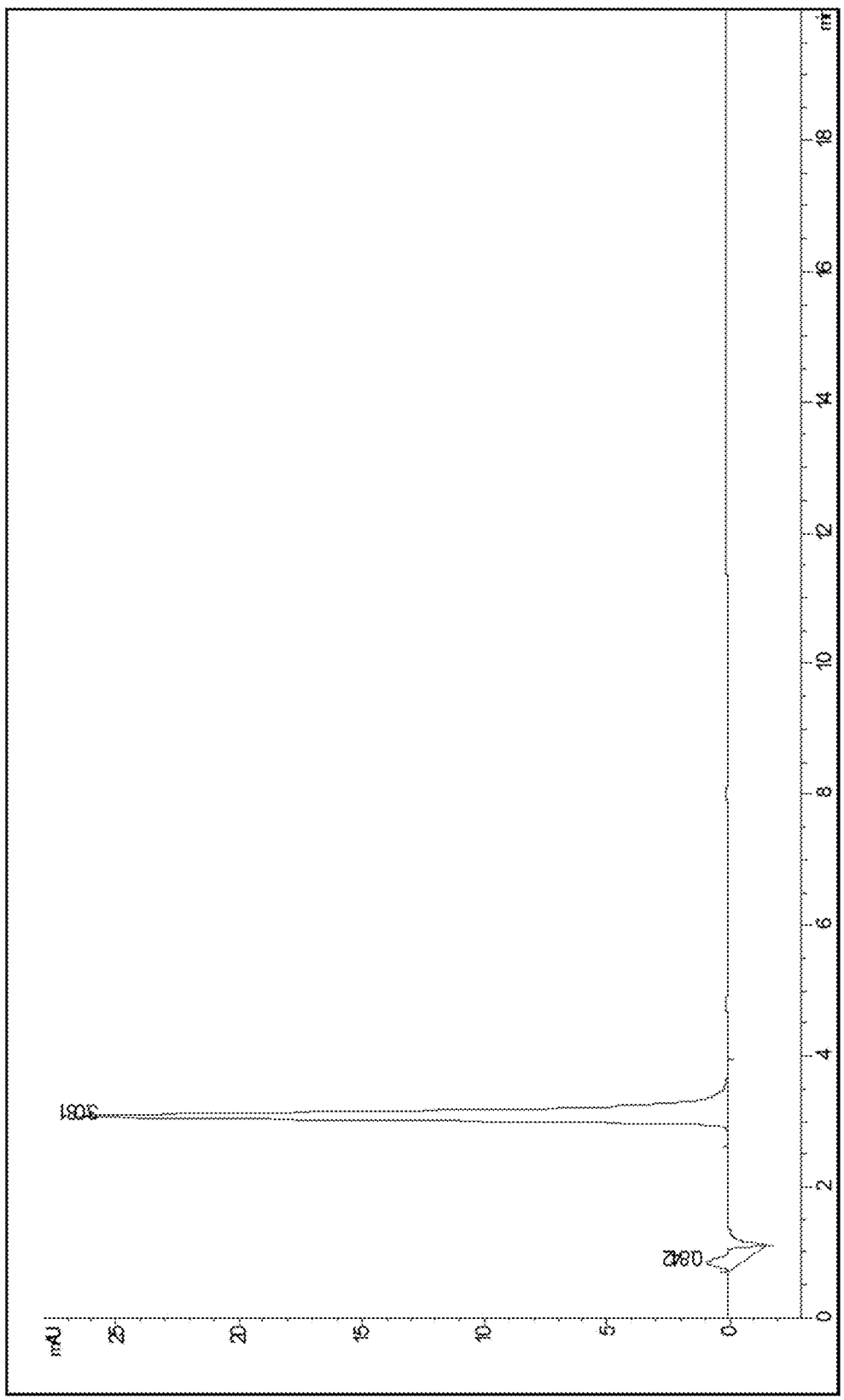
FIG. 9 illustrates a chromatogram of II-38 eluted at 3.08 min in SGF.

As presented in FIGS. 9, 10A, and 10B, II-38 is stable in the SGF, predicting stability of II-38 in vivo in the gastric fluid under acidic conditions for increasing systemic bioavailability.

Stability of II-38 in Simulated Intestinal Fluid (SIF), pH 6.8

Figure 11:
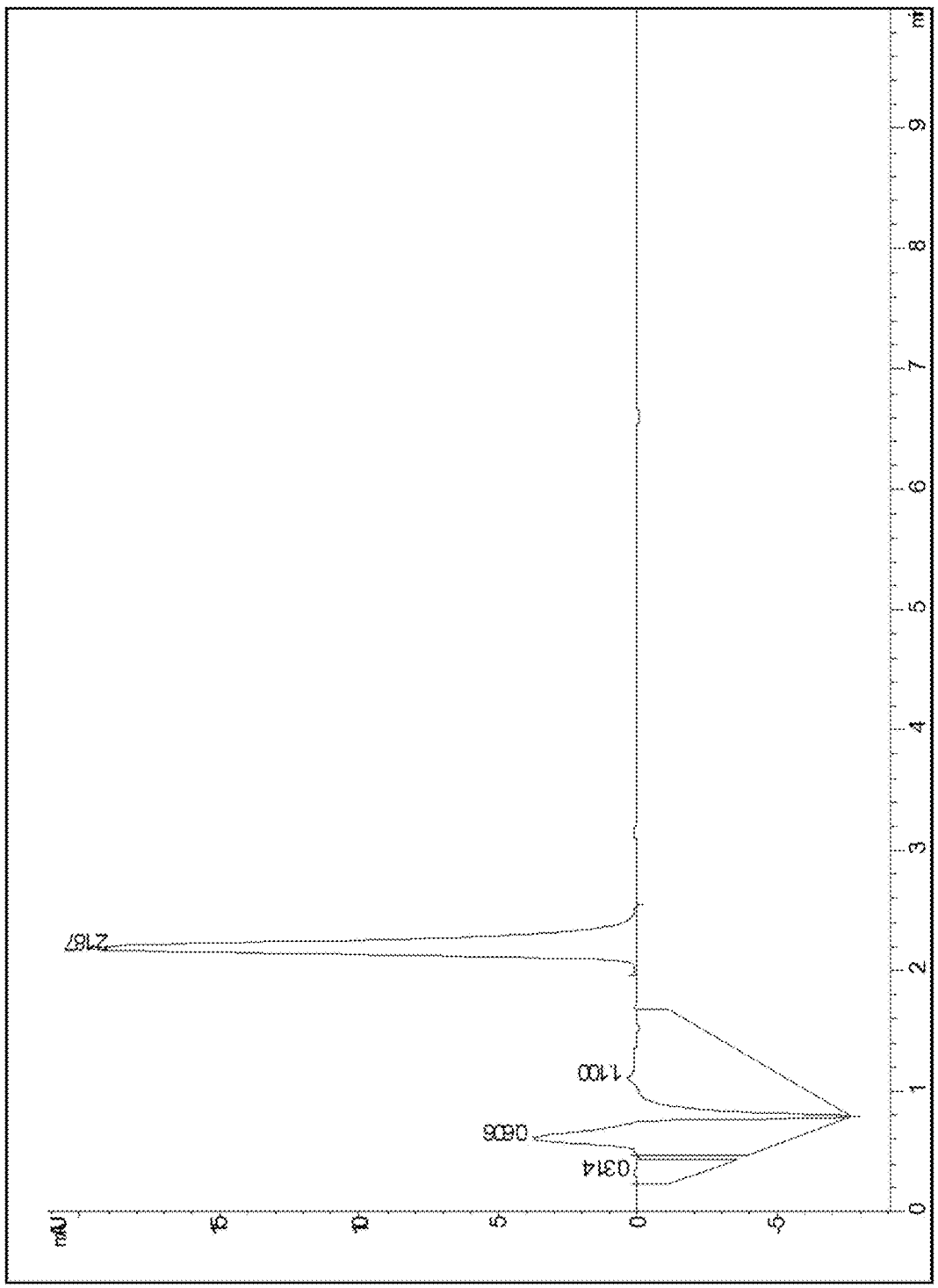
FIG. 11 illustrates a chromatogram of II-38 eluted at 2.187 min in SIF.

Formulation of II-38 in SIF buffer, pH 6.8: to formulate 1 mg/mL of II-38 in SIF, 2.6 mg of II-38 was dissolved in 0.13 mL of DMSO (i.e. 5%) and titrated slowly and gradually to a total volume of 2.47 mL of preheated SIF (Table 4) in a cell diffusion chamber preheated to 37° C. The solution was mixed for 30 sec every half an hour using magnetic stirrer. Samples of 20 (20 μg/mL of II-38) were collected at 0, 0.5, 1, 2, 4, 6 and 8 h (FIGS. 12A and 12B). Each sample was mixed with acetonitrile QS to 1 mL, vortex-mixed for 30 sec and centrifuged at 10,000 rpm at room temp. A volume of 10 μL of the supernatant was injected into the HPLC spectrometer (FIG. 11).

TABLE 4

Formulation of II-38 in SIF

| Weight of II-38 | Total Volume PBS + DMSO (mL) | DMSO (5%) (mL) | SIF (mL) |
|---|---|---|---|
| 2.6 mg | 2.6 | 0.13 | 2.47 |

Stability of II-38 in Rat and Human Plasma

Figure 13:
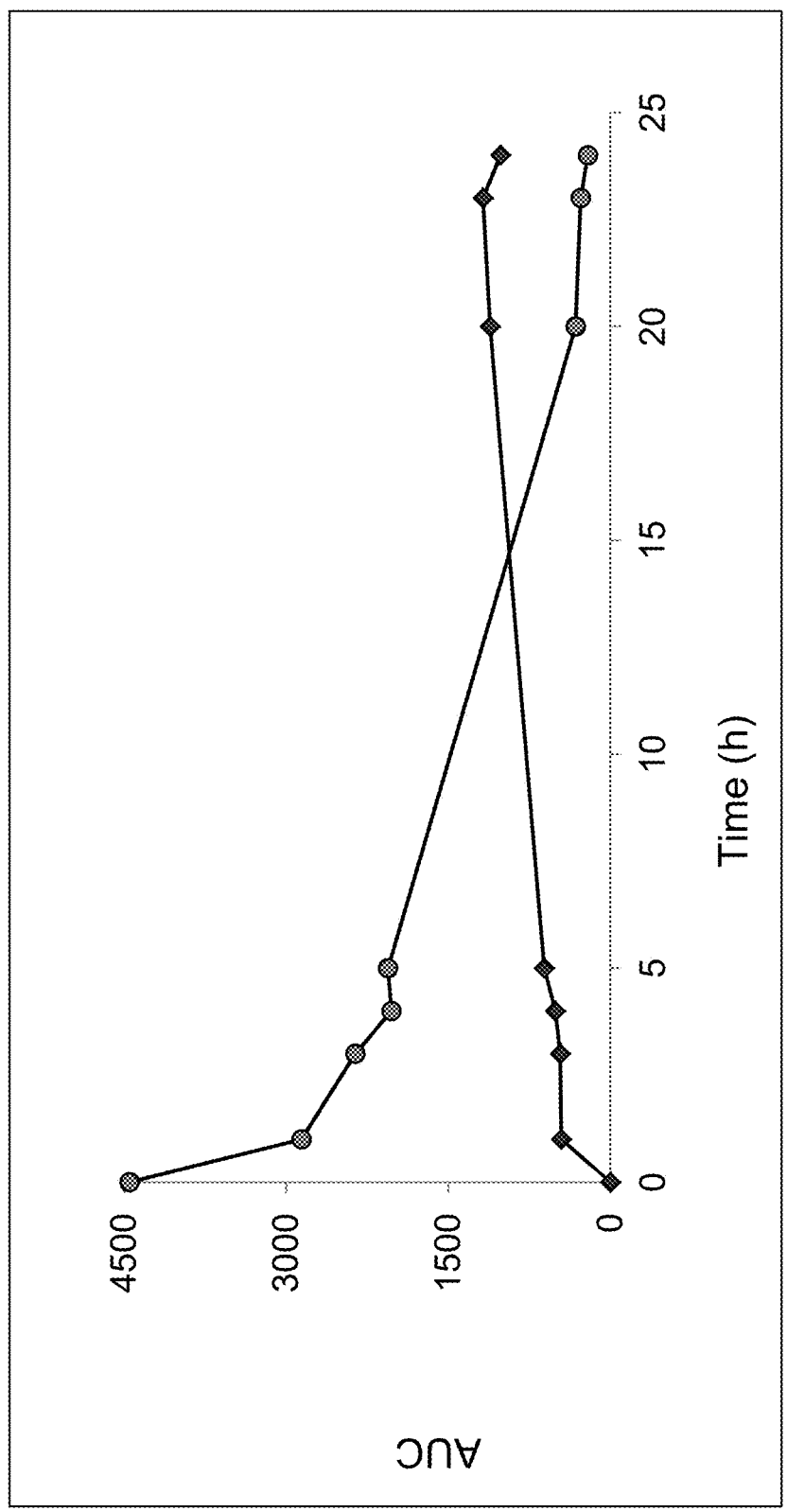
FIG. 13 illustrates II-38 and 2,4-DNP released from II-38 in rat plasma. Legend: diamond—2,4-DNP; circle—II-38.
Figure 14:
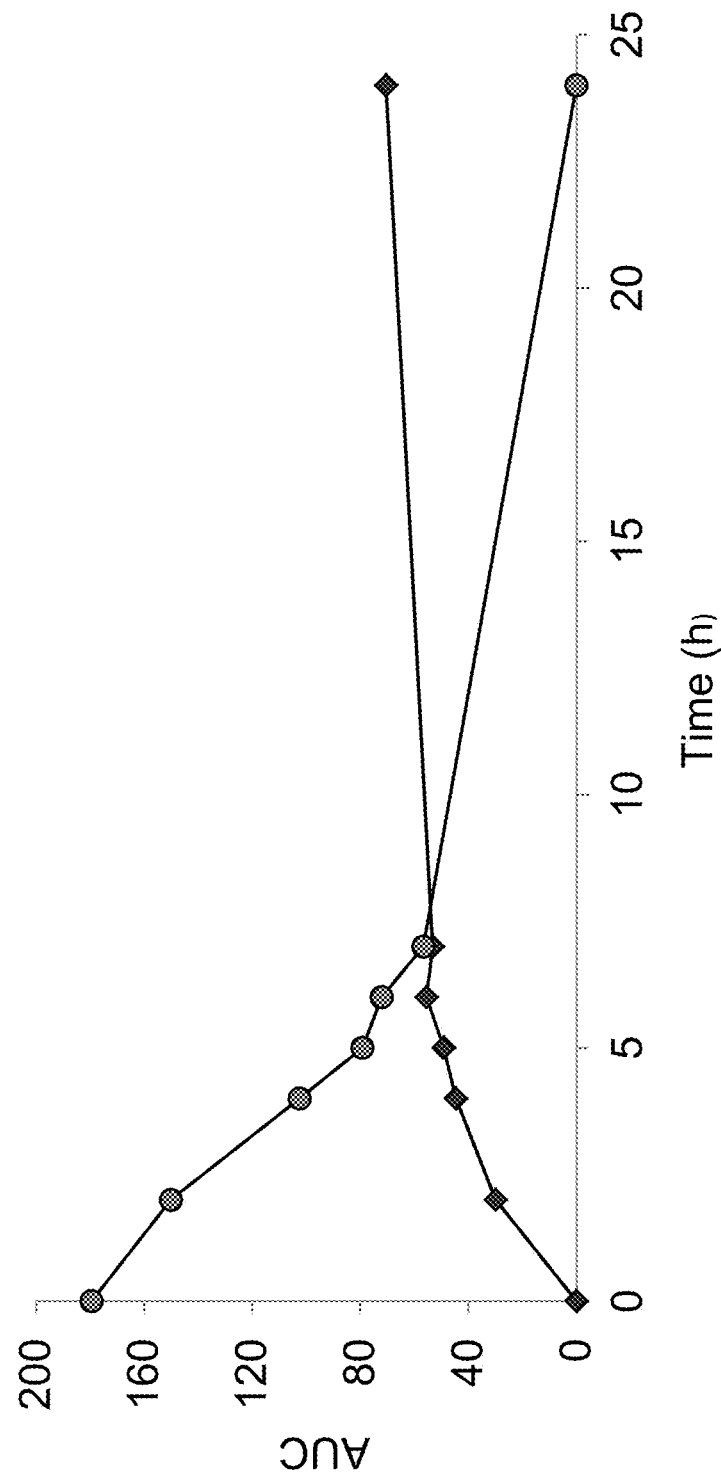
FIG. 14 illustrates II-38 and 2,4-DNP released from II-38 in human plasma. Legend: diamond—2,4-DNP; circle—II-38.

Formulation of II-38 in rat plasma: to prepare 1 mg/mL of II-38 in rat plasma, 2.4 mg of II-38 was formulated in DMSO (5%) and added slowly and gradually to a total volume of 2.28 mL of premixed rat plasma (80%+PBS 15%, Table 5) in a Franz cell diffusion chamber preheated to 37° C. The solution was mixed for 30 sec every half an hour using magnetic stirrer. Samples of 20 μL (20 μg/mL of II-38) were collected at 0, 1, 3, 4, 5, 20, 23, and 24 h (FIGS. 13 and 14). Each sample was mixed with acetonitrile QS to 1 mL, vortex-mixed for 30 sec and centrifuged at 10,000 rpm at room temp. A volume of 10 μL of the supernatant was injected into the HPLC spectrometer.

TABLE 5

Formulation of II-38 in rat plasma.

| Wt. of II-38 (Mg) | Total volume of rat plasma (80%) + PBS 15% + DMSO 5%, mL | rat plasma (80%), mL | PBS (15%), mL | DMSO 5%, mL |
|---|---|---|---|---|
| 2.40 | 2.40 | 1.92 | 0.36 | 0.12 |

Detection of 2,4-DNP and II-38 in Human Plasma Using HPLC

Formulation of II-38 in human plasma: to prepare 1 mg/mL of II-38, 2.3 mg of II-38 was formulated in DMSO (5%) and added slowly and gradually to a total volume of 2.185 mL of premixed human plasma (80%+PBS 15%, see Table 6) in a Franz cell diffusion chamber preheated to 37° C. The solution was mixed for a min every half an hour using magnetic stirrer. Samples of 20 μL (20 μg/mL of II-38) were collected at 0, 0.5, 1, 2, 4, 6 and 8 h. Each sample was mixed with acetonitrile QS to 1 mL, vortex-mixed for 30 sec and centrifuged at 10,000 rpm at room temp. A volume of 10 μL of the supernatant was injected into the HPLC spectrometer.

TABLE 6

Formulation of II-38 in human plasma.

| Wt. of II-38 (Mg) | Total volume of human plasma (80%) + PBS 15% + DMSO (mL) | human plasma (80%) mL | PBS (15%) mL | DMSO 5% (mL) |
|---|---|---|---|---|
| 2.3 | 2.3 | 1.84 | 0.345 | 0.115 |

Summary

Data from stability study of II-38 in different nonenzymatic aqueous buffers clearly indicate that II-38 did not show significant hydrolysis in acidic and basic buffers media. It can be concluded that II-38 will be stable enough in the GI tract when administered orally to be absorbed as a single chemical entity. However, hydrolysis of II-38 in 80% rat and human plasma predicted that II-38 would hydrolyze in systemic circulation to produce its parent drug, 2,4-DNP. The carbamate linkage in II-38 was cleaved in the plasma to produce 2,4-DNP at a slow rate, which allows II-38 to act as a chemical reservoir of 2,4-DNP for a prolonged period of time.

Example 2: Pharmacokinetic Analysis of 2,4-DNP and II-38

The oral bioavailability and plasma pharmacokinetic (PK) properties of II-38 prodrug and 2,4-DNP-released from II-38 prodrug was investigated in Sprague-Dawley (S-D) male rats after a single i.v. injection of II-38 at 1.6 mg/kg (eq. to 1 mg/kg 2,4-DNP) and an oral dose eq. to 5, 25 and 50 mg/kg of 2,4-DNP. Blood samples were taken up to 24 hour.

Animals

All procedures that involved the use of rats were conducted in accordance with the guidelines set forth by the University of Arkansas for Medical Sciences (UAMS) Institutional Animal Care and Use Committee established by the National Institutes of Health's *Guide for the Care and Use of Laboratory Animals* (1996). Male Sprague-Dawley rats weighing 250-300 grams were housed three per cage with ad libitum access to food and water in the Division of Laboratory Animal Resources, UAMS. Rats were anesthetized with isofluorane (2-5%)/oxygen (1.5-2.0 L/min) and surgically implanted with cannulae in the jugular (i.v. dosing) and femoral (blood sampling) veins. After 3-4 days post-surgery, rats were observed for signs of local infection at surgical sites, for hair yellowing, for presence of blood around the nose or eyes, for indications of lessened appetite, and for signs of lessened or absent fecal activity. Following appropriate evidence of successful recovery from surgery, IV or oral dosing was performed and blood samples (0.15 mL) were collected at 0, 5, 15, 30, 45, 60, 120, 240 and 480 min. Plasma samples were prepared and analysis was run using a LC/MS/MS spectrometry.

2, 4-DNP Dose Preparation 2,4-DNP was dissolved in a phosphate-saline buffer solution, pH 7.4 containing 5% DMSO and 20% PEG-400 and filtered through a 0.2-μm filter. For the oral route, rats were gavaged with 5 mg/kg in a total volume of 8 mL/kg from a stock solution containing 0.625/mL of 2,4-DNP. For the i.v. injection, a total volume of 0.8 mL/kg was used at a dose of 1 mg/kg from a stock solution containing 1.25 mg/mL.

II-38 Dose Preparation

For the i.v. injection, a total volume of 0.8 mL/kg was used at a dose of 1.6 mg/kg (eq. to 1 mg/kg of 2,4-DNP). For the oral route, stock solutions of II-38 containing eq. to 1, 5 and 25 mg/mL of 2,4-DNP were prepared and administered to rats at final doses eq. to 1, 5 and 25 mg/kg of 2,4-DNP, respectively. An oral dose of 8 mg/kg of II-38 (eq. to 5 mg/kg) was dissolved in a phosphate-saline buffer solution, pH 7.4 containing 5% DMSO and 20% PEG-400, while a dose of 40 mg/kg (eq. to 25 mg/kg) was formulated with 0.5% methyl cellulose (methocel) containing 1% DMSO. A high dose of II-38 (eq. 50 mg/kg) was formulated with water containing 1% DMSO and 40% PEG-400. Because of the different vehicles used in formulations of II-38, a dose eq. to 25 mg/kg of 2,4-DNP was repeated using a vehicle consisting of DMSO, PEG-400, and water (1%: 40%: 59%). The later dose was utilized for comparison of PK data of 2,4-DNP-released from II-38 for differences in formulations.

Oral and i.v. Animal Experiments of 2, 4-DNP

Jugular and femoral vein-catheterized Sprague-Dawley male rats (weights 250-300 g) were treated with 2,4-DNP at a single oral dose of 5 mg/kg (n=4) or a single i.v. dose of 1 mg/kg (n=3). For each i.v. and oral experiment, blood samples (0.15 mL) were collected at 0, 5, 15, 30, 45, 60, 120, 240 and 480 min. The withdrawn blood was replaced with heparinized saline (0.15 mL). Blood samples were centrifuged at 10,000 rpm for 10 min at room temperature, and plasma samples were prepared and analysis was run using a sensitive LC/MS/MS spectrometry method (see below).

Oral and i.v. Animal Experiments of II-38

Jugular and femoral vein-catheterized Sprague-Dawley male rats (weights 250-300 g, n=4) were treated with II-38 at a single oral dose of 8, 40 and 80 mg/kg (eq. to 5, 25 and 50 mg/kg of 2,4-DNP, respectively) or injected a single i.v. dose of 1.6 mg/kg of II-38 (eq. to 1 mg/kg 2,4-DNP, n=2). Blood samples (0.15 mL) were collected at 0, 5, 15, 30, 45, 60, 120, 240 and 480 min. Plasma samples were prepared and 2,4-DNP, II-38 and 2,4-DNP-released from II-38 concentrations were quantitated using the LC/MS/MS spectrometry assay method described below.

Preparation of Plasma Samples and Extraction Procedure

To isolate the analytes from rat plasma, 50 μL of control or treated plasma fortified with 10 of 2,4-DNP-d3 (10 μg/mL) as an internal standard to which 0.3 mL of methanol followed by 0.3 mL of acetonitrile was added. The mixture was vortex-mixed for 30 s and centrifuged for 10 min at 10,000 rpm at room temperature. The supernatant was transferred into 5 mL glass tubes and evaporated to dryness at 37° C. under nitrogen gas. The pellet was reconstituted with 50 of acetonitrile, vortex-mixed for 30 sec, followed by sonication for 1 min. Following centrifugation at 1000 rpm for 10 min at room temperature, 5 μL of the supernatant was then injected onto the column, and analytes were quantified by a LC/MS/MS spectrometry.

LC/MS/MS Analysis

A sensitive liquid chromatography/tandem mass spectrometry (LC/MS/MS) assay has been applied to quantify 2,4-DNP and II-38 in rat plasma as follows:

1—Plasma concentrations of 2,4-DNP after a single i.v. injection of 2,4-DNP of 1 mg/kg or 5 mg/kg oral administration; 2—Plasma concentrations of II-38 and 2,4-DNP-released from II-38 after an i.v. injection 1.6 mg/kg of II-38 eq. to 1 mg/kg of 2,4-DNP or an oral dose of 8, 40 and 80 mg/kg of II-38 eq. to 5, 25 and 50 mg/kg of 2,4-DNP, respectively. The mass spectrometer was an Agilent quadrupole mass spectrometer operated in the multiple reaction monitoring (MRM) mode. 2,4-DNP-d3 was used as an internal standard. 2,4-DNP, II-38 and 2,4-DNP-d3 were separated using an Alltima C18 column, 5 μm, 3.2×150 mm (Grace Discovery Sciences, IL, USA) equipped with a guard column: Alltima C18, 5 μm, 4.6×7.5 mm (Grace Discovery Sciences, IL, USA). The mobile phase consists of water with 0.005% formic acid as solvent A and acetonitrile with 0.005% formic acid as solvent B. For analysis of 2,4-DNP, II-38 and 2,4-DNP-d3 compounds, the separation was achieved using a gradient of 10 to 90% solvent B in 3.5 min, which was maintained at 90% B for the next 3.30 min and then equilibrated back to the initial conditions over 3.20 min. The flow rate was 0.8 mL/min with a column temperature of 30° C. The sample injection volume was 5 µL. The mass spectrometer was operated in the negative electrospray ionization mode with optimal ion source settings determined using standards of 2,4-DNP, II-38 and 2,4-DNP-d3 with a collision energy of 15 V, and a fragmentor of 75 V. MRM transitions monitored were as follows: 2,4-DNP—m/z 183.0/123.0, m/z 183.0/153.0, for 2,4-DNP-d3—m/z 186.0/126.0, m/z 186.0/156.0 and for II-38—m/z 297.2/183.2. Two separate standard curves of 2,4-DNP and II-38 in rat plasma were generated and used to quantify 2,4-DNP and II-38, respectively.

Standard Curve of 2,4-DNP in Acetonitrile (ACN)

Figure 15:
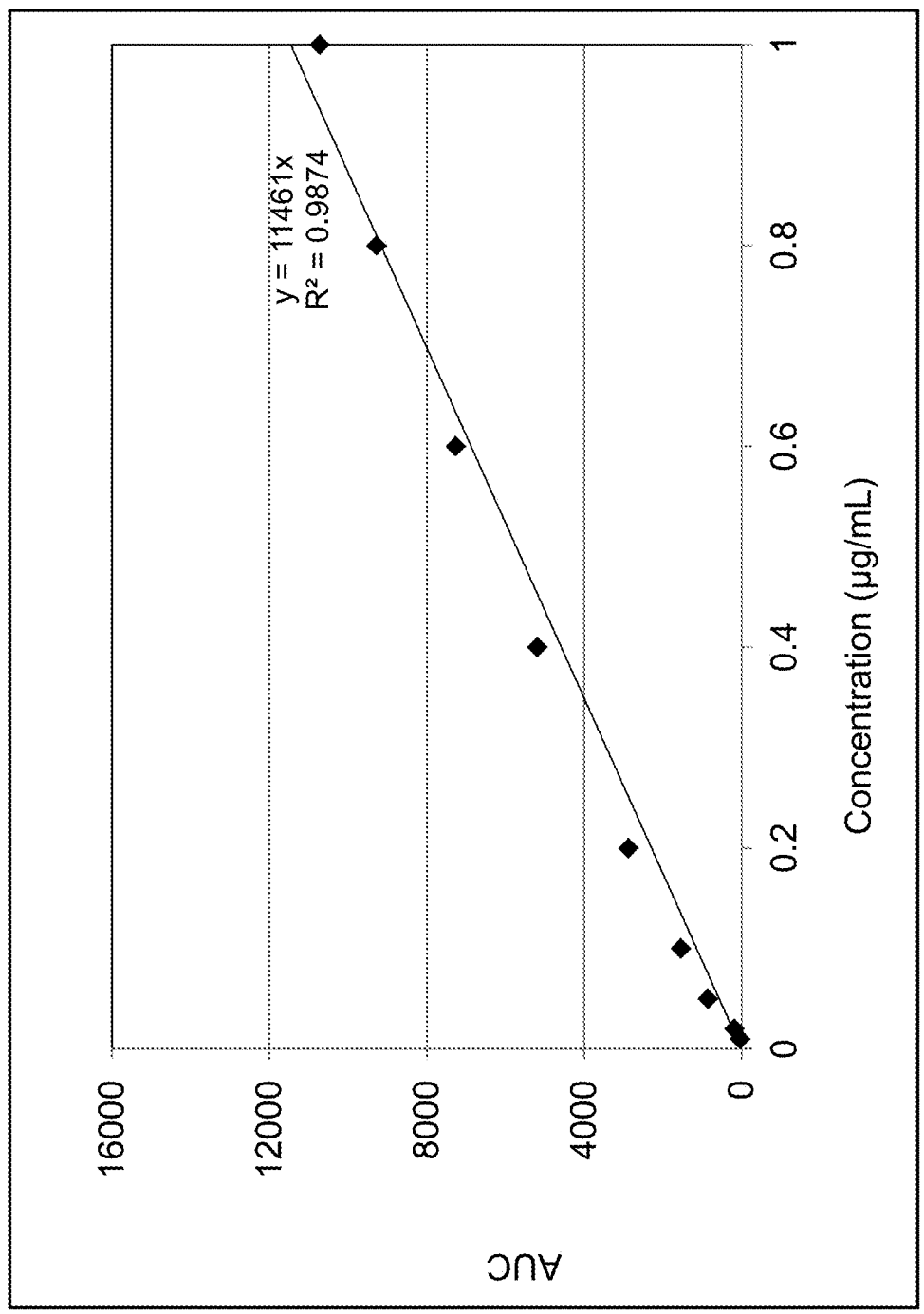
FIG. 15 illustrates the calibration standard of 2,4-DNP in acetonitrile.

Stock solution of 2,4-DNP was prepared in acetonitrile. Standard curve with 8 different concentrations was prepared. Calibration curve was obtained using quadratic least-squares regression of area-under-the-curve (AUC) vs. 2,4-DNP concentration. The curve was linear between 0.01-1 µg/ml with a correlation coefficient of $R^2=0.9874$ (FIG. 15).

Standard Curves of 2, 4-DNP and II-38 in Plasma

Figure 16:
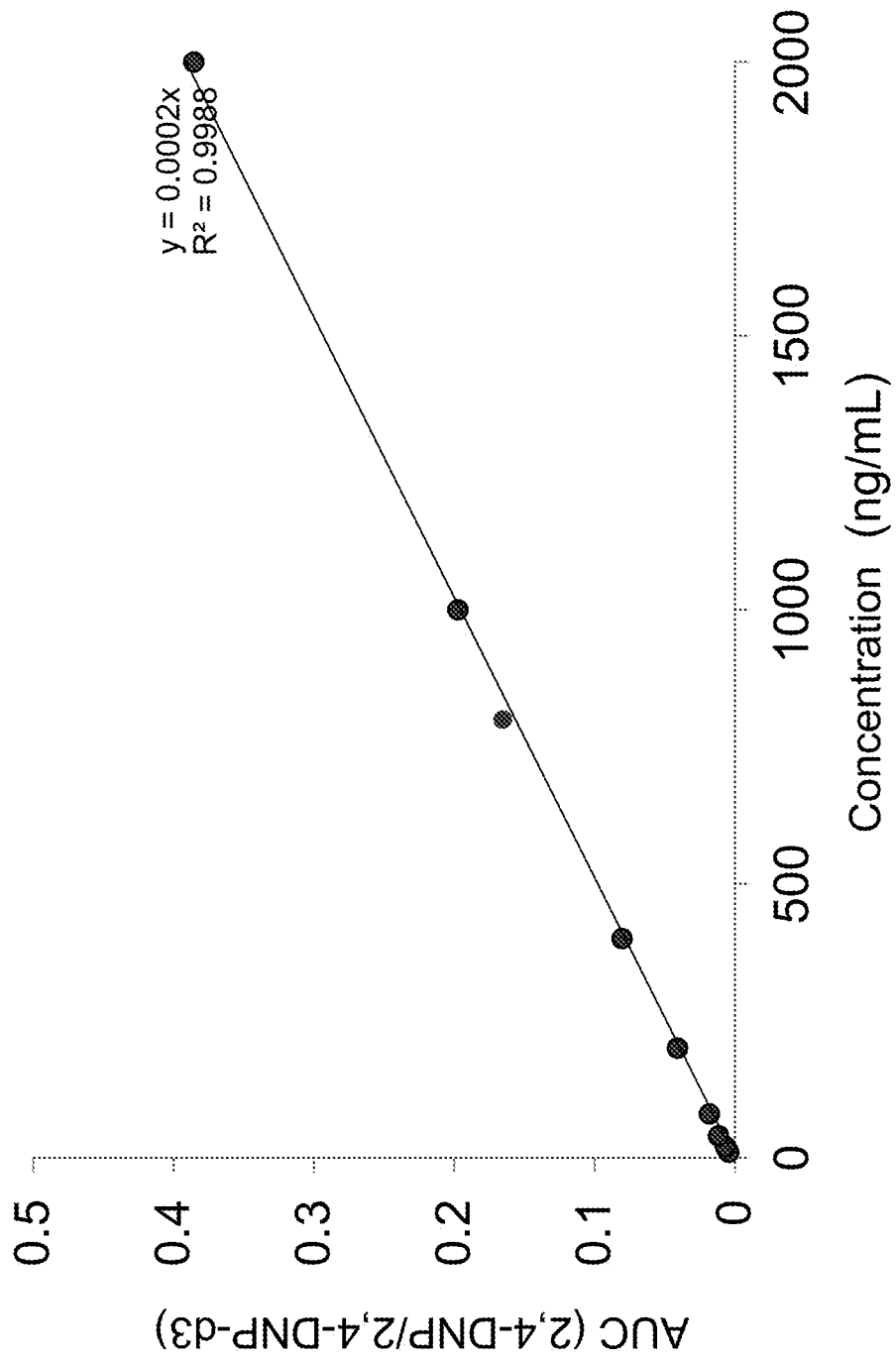
FIG. 16 illustrates the calibration standard of 2,4-DNP in rat plasma, n=5.
Figure 17:
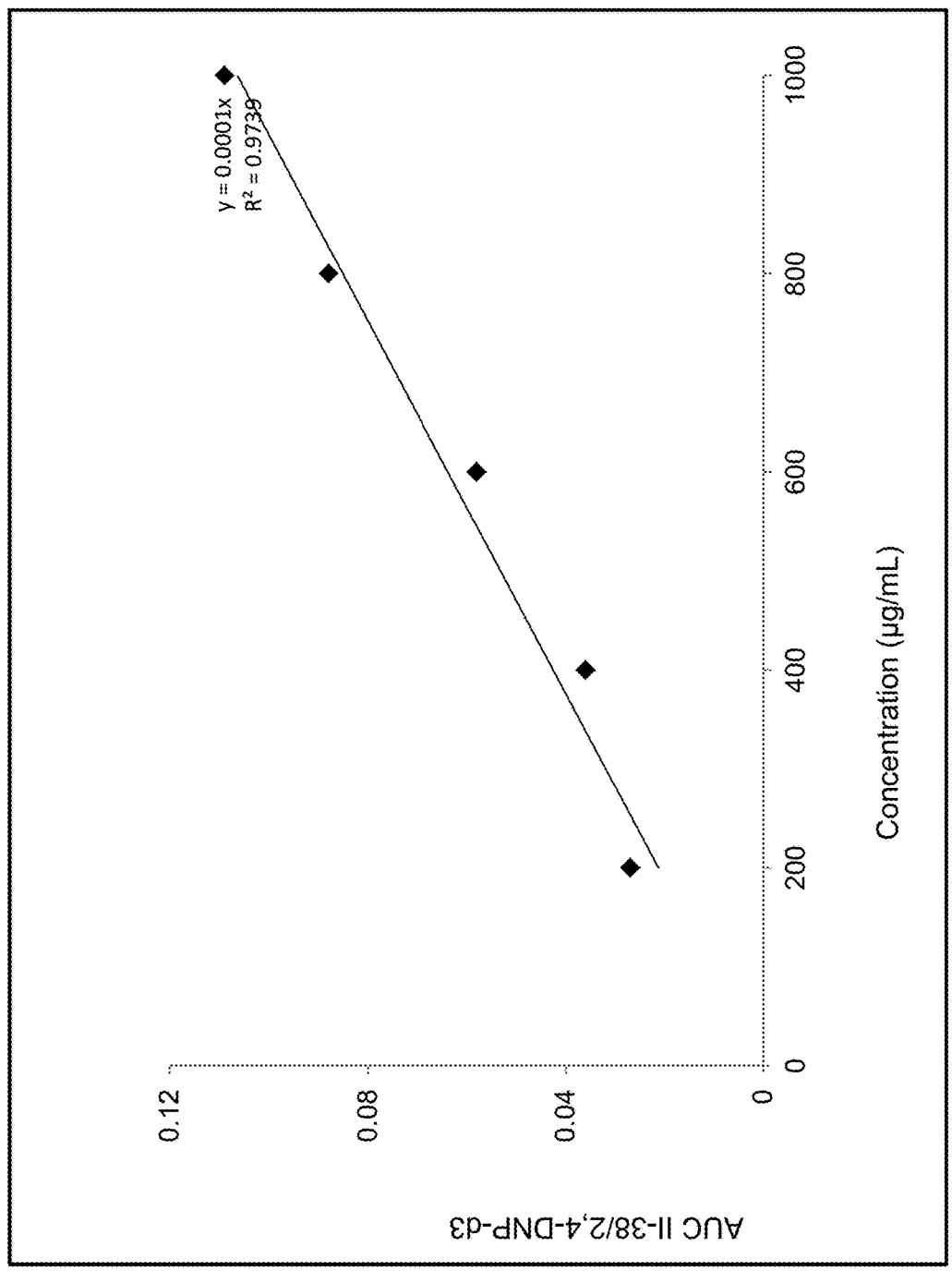
FIG. 17 illustrates the standard curve of II-38 in rat plasma, n=3.

Stock solutions of each of 2,4-DNP and II-38 and internal standard (2,4-DNP-d3) were prepared in acetonitrile. Serial dilutions of the 2,4-DNP and II-38 solutions were prepared and LC/MS/MS chromatograms of 2,4-DNP and II-38 calibration standards generated for each analyte over the concentration range 1-2000 ng/mL in plasma (n=5). The calibration curves and chromatograms showed excellent linearity between 20-2000 ng/mL and 200-1000 ng/mL for 2,4-DNP and II-38, respectively, with a correlation coefficient of $R^2=0.9988$ and 0.9739 for 2,4-DNP and II-38, respectively (FIGS. 16 and 17).

Plasma Pharmacokinetics

Individual 2,4-DNP and II-38 prodrug plasma concentration-time profiles after i.v. bolus administration were calculated using a one-compartment open model and first order elimination (Phoenix WinNonlin, Professional, version 6.2, Pharsight, Mountain View, Calif.).

Following oral administration, data were analyzed by a non-compartment open model and first order absorption to determine peak concentration ($C_{max}$), $T_{max}$, and area under the curve from 0 to infinity ($AUC_{0\text{-}inf}$). Actual apparent bioavailability of 2,4-DNP, II-38 prodrug and 2,4-DNP-released from II-38 was determined using Equation 1:

$$F\% = \frac{(AUC_{oral})(\text{Dose}_{i.v.})}{(AUC_{i.v.})(\text{Dose}_{oral})} \times 100 \quad \text{(Equation 1)}$$

where $AUC_{oral}$ $AUC_{i.v.}$, $\text{Dose}_{oral}$, and $\text{Dose}_{i.v.}$ represent the $AUC_{0\text{-}inf}$ and corresponding dose for the oral and i.v. injections of 2,4-DNP or II-38 prodrug, respectively. The bioavailability of 2,4-DNP released from II-38 was obtained from the AUC of 2,4-DNP released from oral and i.v. administration of II-38 using Equation 1.

Total apparent bioavailability of II-38 prodrug was estimated in the same manner using AUC data for both II-38 prodrug and 2,4-DNP. Equation 2 is the modified form of the bioavailability expression which takes into account the time-dependent hydrolysis of II-38 prodrug after administration to rat. The best estimate for the total bioavailability includes the AUC data for released 2,4-DNP in the plasma as well.

The release of 2,4-DNP from II-38 prodrug occurs in an equimolar ratio. Since the prodrug is being hydrolyzed to release 2,4-DNP in a 1:1 ratio, it follows that an equal amount of II-38 has hydrolyzed to form 2,4-DNP. The calculation of oral bioavailability of the prodrug involves two different metrics. Actual apparent bioavailability takes into account the time-dependent hydrolysis of II-38 prodrug. To estimate total apparent bioavailability of the II-38, systemic exposure to both II-38 prodrug and its released 2,4-DNP must be considered. It can be calculated using Equation 2:

$$F\% = \frac{(AUC_{II-38,oral} + AUC_{2,4-DNP,oral})(\text{Dose}_{II-38,i.v.})}{(AUC_{II-38,i.v.} + AUC_{2,4-DNP,i.v.})(\text{Dose}_{II-38,oral})} \times 100 \quad \text{(Equation 2)}$$

Figure 18:
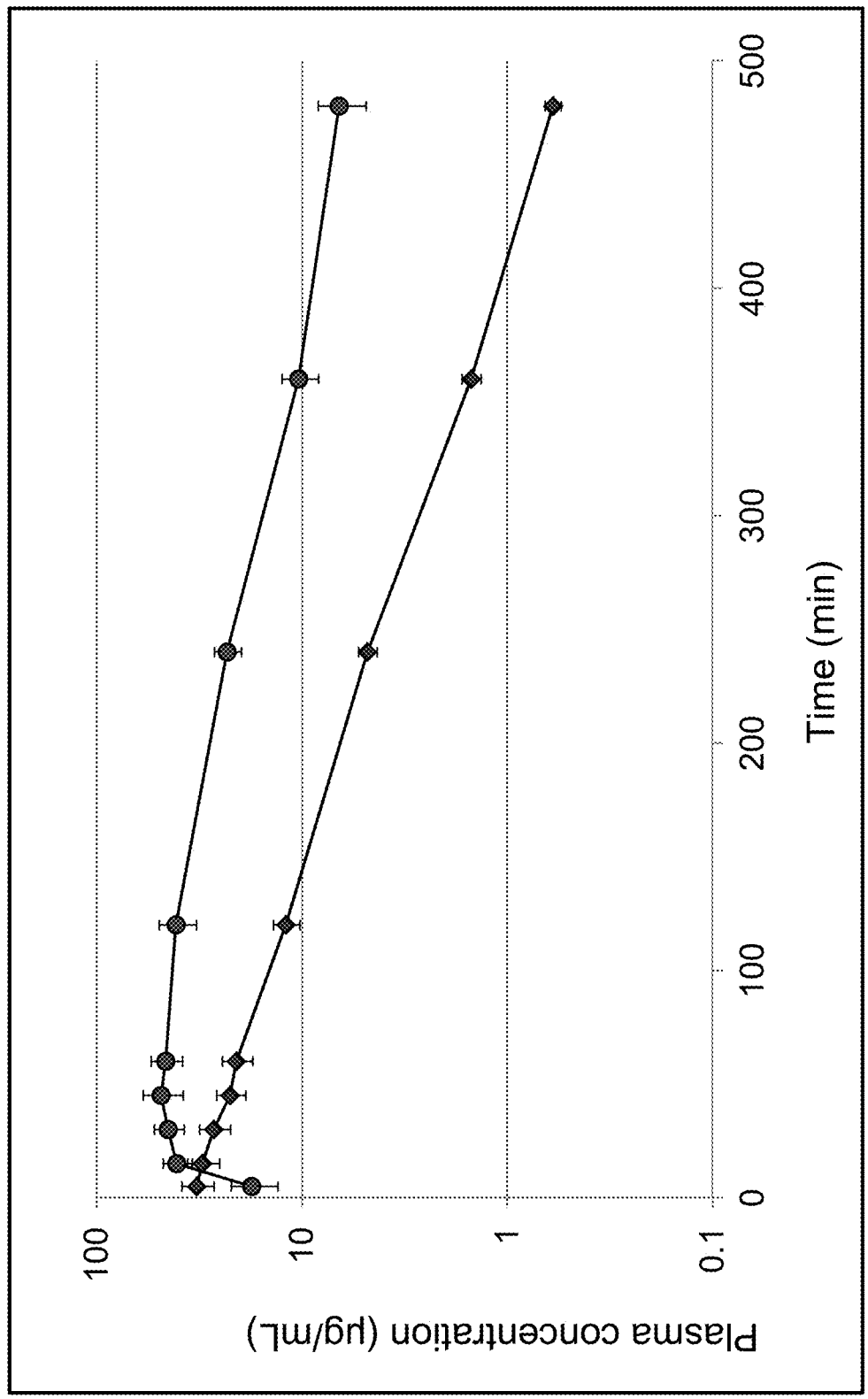
FIG. 18 illustrates the plasma concentration of 2,4-DNP vs. time after a single iv injection of 1 mg/kg (n=3) or an oral dose of 5 mg/kg (n=4) of 2,4-DNP in rats. Legend: diamond—2,4-DNP, iv, 1 mg/Kg; circle—2,4-DNP, oral, 5 mg/Kg.
Figure 19:
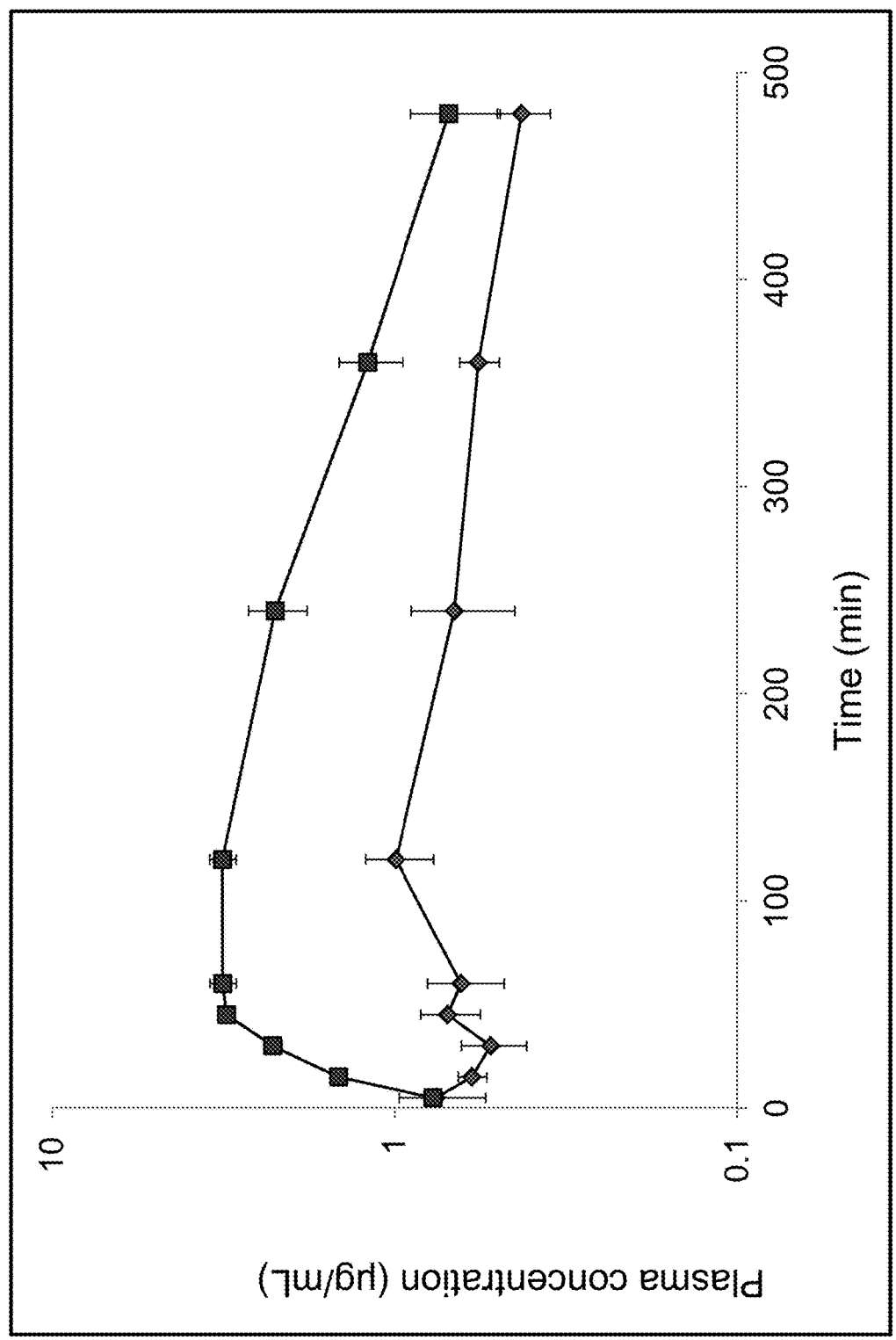
FIG. 19 illustrates the mean plasma concentrations vs. time of II-38 and 2,4-DNP released from II-38 prodrug after administration of an oral dose of 8 mg/kg of II-38 (eq. to 5 mg/kg of II-38). Legend: diamond—II-38, oral: eq. 5 mg/Kg; square—2,4-DNP, released from II-38, oral.
Figure 20:
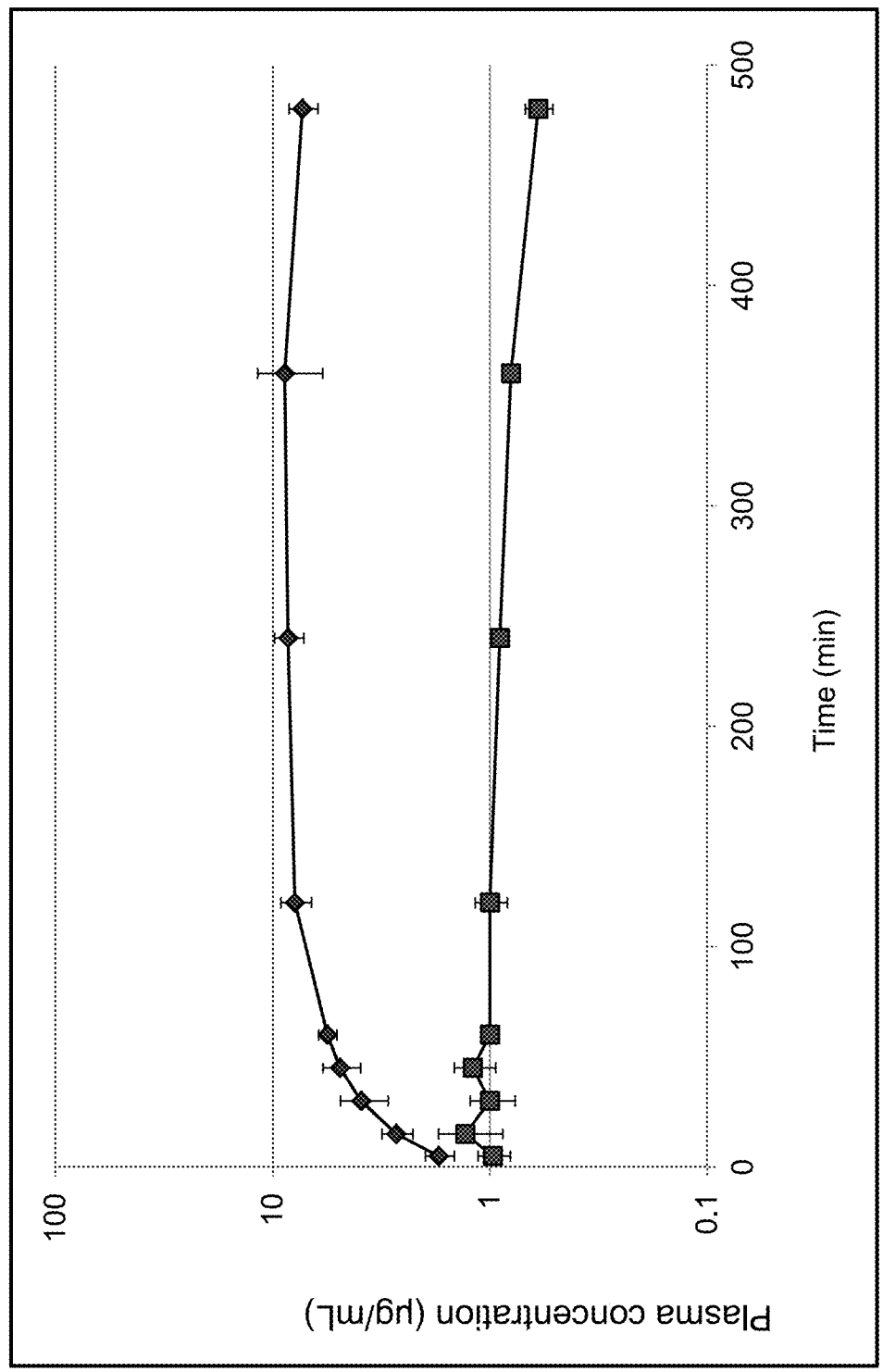
FIG. 20 illustrates the mean plasma concentrations vs. time of II-38 and 2,4-DNP released from II-38 prodrug after administration of an oral dose of 40 mg/kg of II-38 (eq. to 25 mg/kg of II-38 formulated in methocel). Legend: diamond—2,4-DNP, released from II-38, oral; square—II-38, oral: eq. 25 mg/Kg (methocel).
Figure 21:
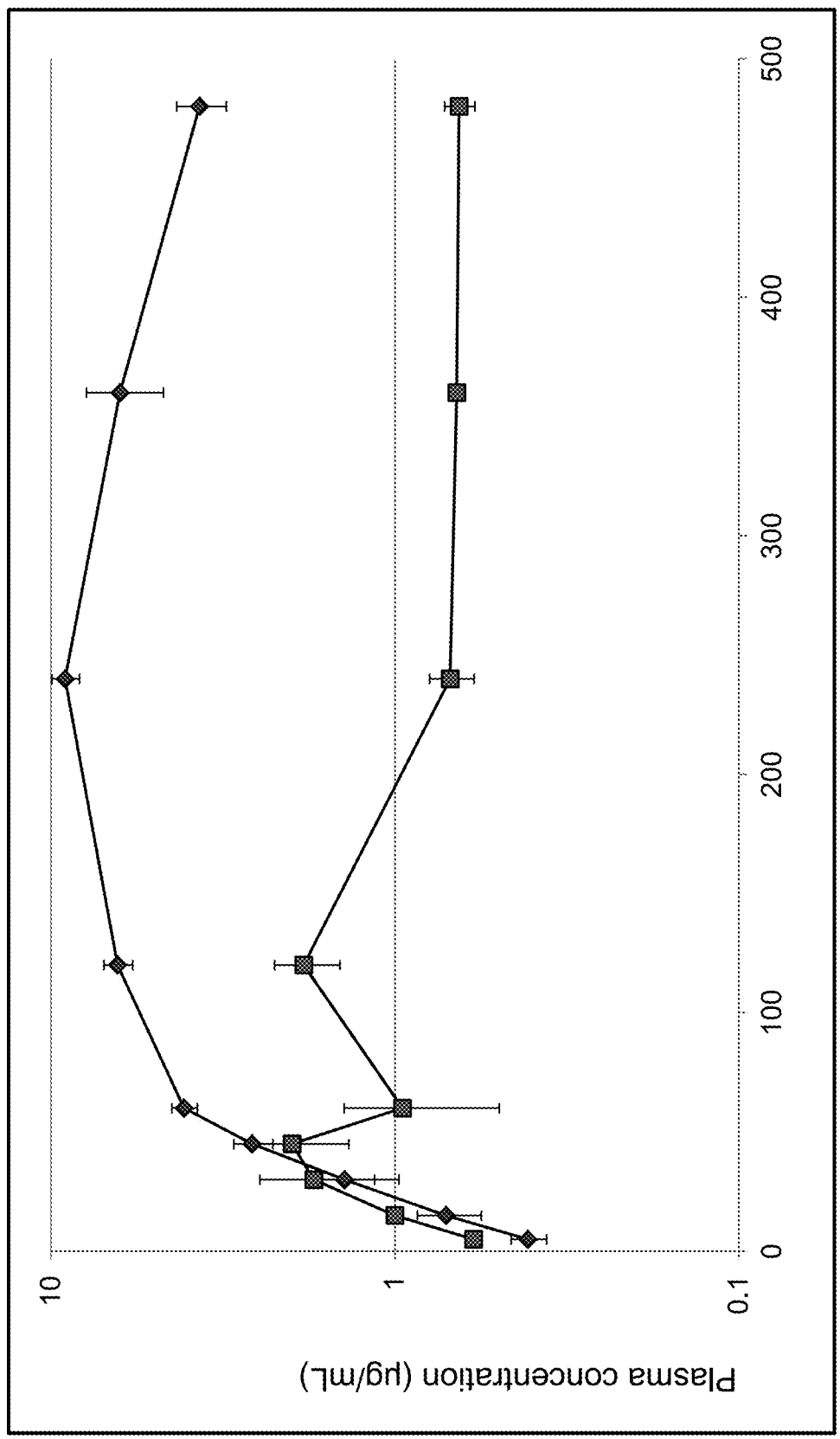
FIG. 21 illustrates the mean plasma concentrations vs. time of II-38 and 2,4-DNP released from II-38 prodrug after administration of an oral dose of 40 mg/kg of II-38 (eq. to 25 mg/kg of II-38 formulated in PEG-400). Legend: diamond—2,4-DNP, released from II-38, oral; square—II-38, oral: eq. 25 mg/Kg (PEG-400).
Figure 22:
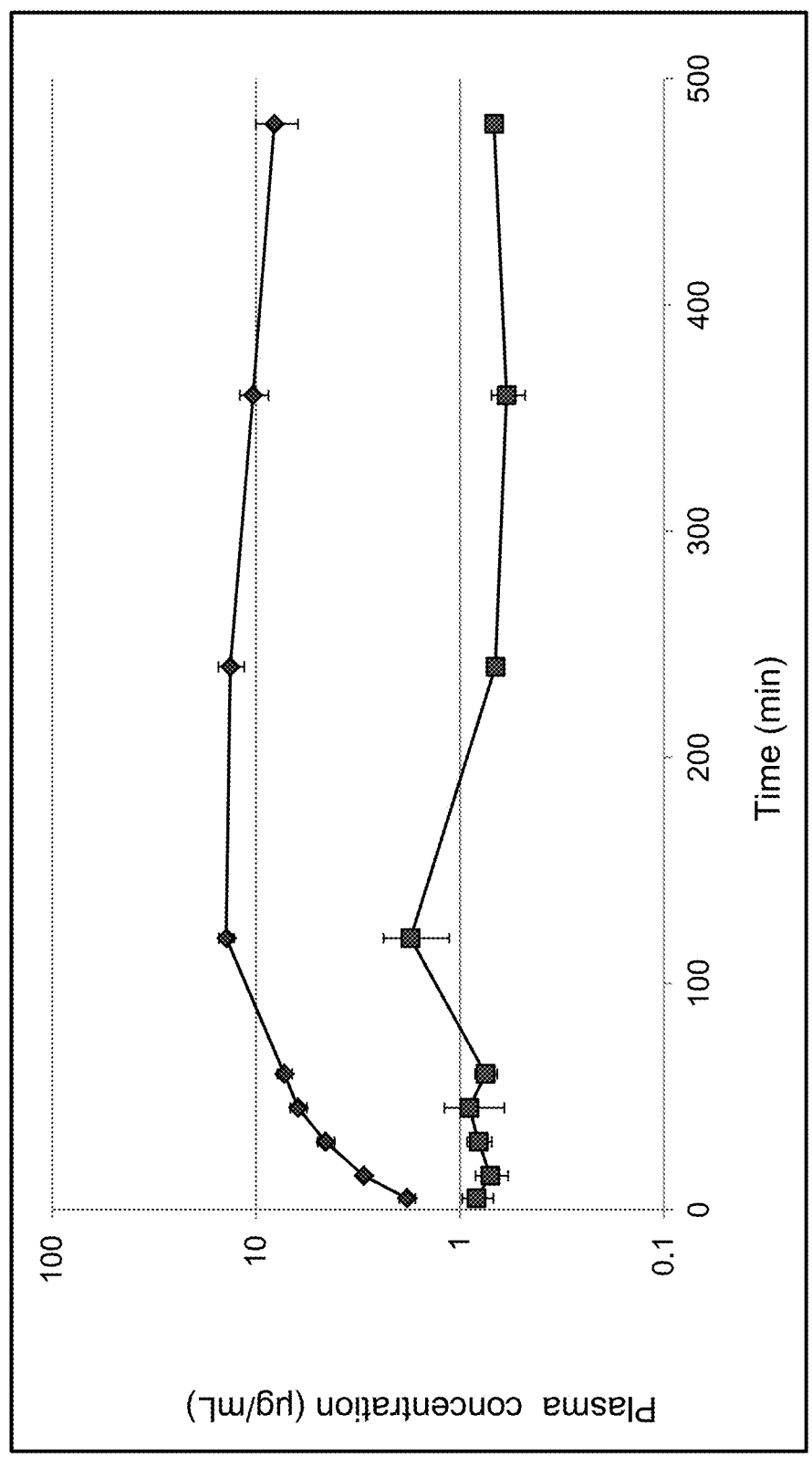
FIG. 22 illustrates the mean plasma concentrations vs. time of II-38 and 2,4-DNP released from II-38 prodrug after administration of an oral dose of 80 mg/kg of II-38 (eq. to 50 mg/kg of II-38). Legend: diamond—2,4-DNP, released from II-38, oral; square—II-38, oral: eq. 50 mg/Kg.

Plasma concentration of 2,4-DNP vs. time after oral dosing and i.v. injection is presented in FIG. 18. Following oral dosing, 2,4-DNP absorption was fast as indicated by the plasma concentration at 5 min. The half-life for 2,4-DNP was 90±9.9 min and 136.2±10.9 min for the i.v. and oral routes, respectively Table 7.

Oral administration of II-38 prodrug in S-D rats at doses eq. to 5, 25 (methocel), 25 (PEG-400) and 50 mg/kg of 2,4-DNP resulted in delivery of 2,4-DNP with peak plasma concentrations of 3.2±0.2, 9.4±0.6, 9.1±0.84 and 15.2±2.7 µg/mL being reached within 120±16.9, 161.3±39.4, 240 and 180±34.6 min respectively (Table 8). It is noteworthy that the PK profile for II-38 formulated in DMSO:PEG-400:water (1:40:59) vehicle compares well with the methocel formulation.

TABLE 7

PK profile of 2,4-DNP after treatment with a single i.v. dose of 1 mg/kg (n = 3) or a single oral dose of 5 mg/kg of 2,4-DNP (n = 4 rats)

| PARAMETER (UNITS) | Route | |
|---|---|---|
| | 2,4-DNP, i.v. Mean ± SEM | 2,4-DNP, Oral Mean ± SEM |
| AUC (min * µg/mL) | 1345.9 ± 591.2 | 13288 ± 1634.1 |
| $t_{1/2}$ (min) | 90 ± 9.9 | 136.2 ± 10.9 |
| $C_{max}$ (µg/mL) | 11.5 ± 6.2 | 50.1 ± 7.4 |
| $t_{max}$ (min) | | 37.5 ± 3.8 |
| Cl (mL/min/kg) | 1.2 ± 0.6 | |
| Vss (mL/kg) | 160.8 ± 135.1 | |

Figure 23:
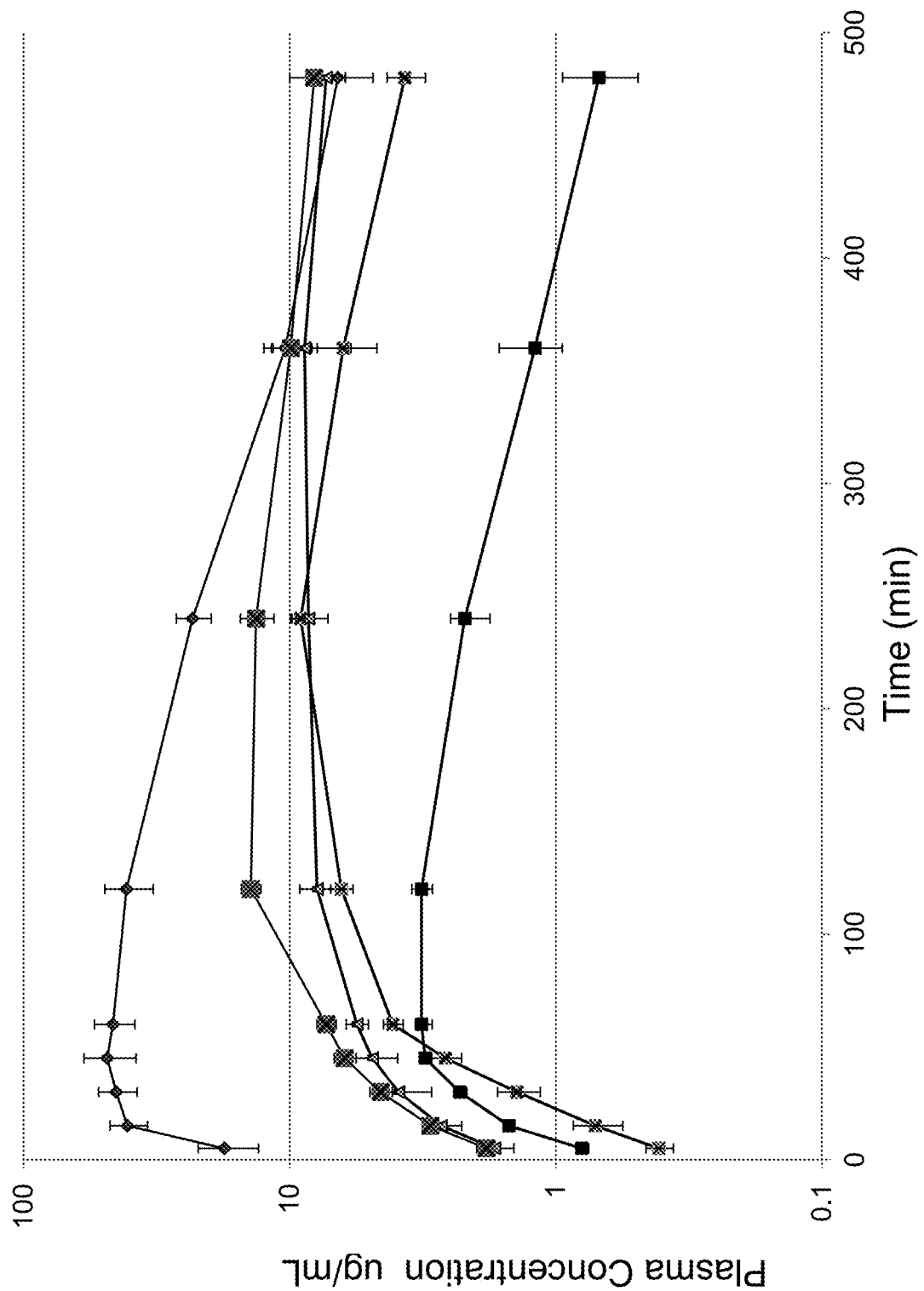
FIG. 23 illustrates the mean plasma concentration of 2,4-DNP and 2,4-DNP released from II-38 after administration of 2,4-DNP at a dose of 5 mg/kg and II-38 at doses of 8, 40 (methocel), 40 (PEG-400) and 80 mg/kg (eq. to 5, 25 (methocel), 25 (PEG-400)] and 50 mg/kg of DNP), respectively. n=4. Legend: diamond—2,4-DNP, oral, 5 mg/Kg; square (red)—2,4-DNP, released from II-38 eq. 5 mg; triangle—2,4-DNP, released from II-38 eq. 25 mg/Kg (methocel); square (purple)—2,4-DNP, released from II-38 eq. 50 mg/Kg; square (blue)—2,4-DNP, released from II-38 eq. to 25 mg/Kg (PEG-400).

FIG. 18 shows the plasma concentration of 2,4-DNP vs. time after a single IV injection, or an oral dose. FIGS. 19, 20, 21, and 22 show mean plasma concentrations vs. time profiles of II-38, and 2,4-DNP released from its II-38 prodrug after oral administration of eq. doses of 5, 25 (methocel), 25 (PEG-400) and 50 mg/kg of 2,4-DNP, respectively. FIG. 23 compares mean plasma concentrations vs. time of 2,4-DNP oral dose of 5 mg/k to 2,4-DNP released from II-38 after oral administration of II-38 at doses of 8, 40 (methocel), 40 (PEG-400) and 80 mg/kg [eq. to 5, 25 (methocel), 25 (PEG-400)] and 50 mg/kg of 2,4-DNP], respectively, n=4. The carbamate linkage of II-38 prodrug apparently cleaved in vivo to produce 2,4-DNP as a hydrolysis product of the II-38 prodrug. Bioavailabilities of 2,4-DNP released from II-38 and II-38 are presented in Tables 8, 9, and 10, respectively.

TABLE 8

PK profile of 2,4-DNP at an oral dose of 5 mg/kg and 2,4-DNP- released from II-38 after treatment with a single oral dose of II-38 eq. to 5, 25 (methocel), 25 (PEG = 500) and 50 mg/kg of 2,4-DNP, respectively, n = 4 rats

| PARAMETER (UNITS) | Mean ± SEM | Mean ± SEM | Mean ± SEM Route | Mean ± SEM | Mean ± SEM |
|---|---|---|---|---|---|
| | 5 mg/kg, Oral 2,4-DNP | 5 mg/kg, Oral 2,4-DNP-released from II-38 | 25 mg/kg, Oral, methocel 2,4-DNP-released from II-38 | 25 mg/kg, PEG-400 2,4-DNP-released from II-38 | 50 mg/kg, Oral 2,4-DNP-released from II-38 |
| AUC (min * ug/mL) | 13288.0 ± 1634.1 | 1105.5 ± 102.3 | 5968.4 ± 471.8 | 3904.7 ± 595.4 | 9515.4 ± 2186.0 |
| $t_{1/2}$ (min) | 136.3 ± 10.9 | 141.7 ± 11.3 | 248.2 ± 45.3 | 185.9 ± 18.1 | 334.1 ± 63.0 |
| $C_{max}$ (ug/mL) | 50.1 ± 7.4 | 3.2 ± 0.2 | 9.4 ± 0.6 | 9.1 ± 0.84 | 15.2 ± 2.7 |
| $t_{max}$ (min) | 37.5 ± 3.8 | 120 ± 16.9 | 161.3 ± 39.4 | 240 | 180 ± 34.6 |
| % F | 65.8 ± 11.4 | 58.5 ± 8.1 | 62.8 ± 5.8 | 41 ± 5.1 | 50.1 ± 11.5 |

PK profile of M101 administered orally and M101 released from M201 (M101-morpholino) after treatment with a single oral dose of M201 (equivalent to 5, 25 and 50 mg/kg of M101, respectively)

| PARAMETER (UNITS) | 5 mg/kg DNP Mean ± SEM | 5 mg/kg Mean ± SEM | 25 mg/kg Mean ± SEM | 50 mg/kg* Mean ± SEM |
|---|---|---|---|---|
| AUC (min * ug/mL) | 13288 | 1105.5 ± 102.3 | 5968.4 ± 471.8 | 9168.5 ± 1283.6 |
| $t_{1/2}$ (min) | 136 | 141.7 ± 11.3 | 248.2 ± 45.3 | 157.7 ± 13.5 |
| $C_{max}$ (ug/mL) | 50 | 3.2 ± 0.2 | 9.4 ± 0.6 | 15.2 ± 0.97 |
| $t_{max}$ (min) | 38 | 120 ± 16.9 | 161.3 ± 39.4 | 180 ± 30 |

*Last time point was 30 h

TABLE 9

PK profile of II-38 after treatment with a single oral dose of II-38 eq. to 5, 25 (methocel), 25 (PEG = 500) and 50 mg/kg of 2,4-DNP, respectively, n = 4 rats

| PARAMETER (UNITS) | Mean ± SEM | Mean ± SEM | Mean ± SEM Route | Mean ± SEM |
|---|---|---|---|---|
| | 5 mg/kg, Oral II-38-Oral | 25 mg/kg, Oral, methocel II-38 | 25 mg/kg, PEG-400 II-38 | eq. 50 mg/kg, Oral II-38 |
| AUC (min * ug/mL) | 902 ± 234.3 | 1103.9 ± 302.2 | 877.1 ± 191.4 | 1456.7 ± 494.4 |
| $t_{1/2}$ (min) | 913.4 ± 419.7 | 662.4 ± 251.9 | 444.6 ± 183.8 | 1060.8 ± 417.4 |
| $C_{max}$ (ug/mL) | 1.1 ± 0.2 | 1.8 ± 0.3 | 2.41 ± 0.3 | 1.9 ± 0.6 |
| $t_{max}$ (min) | 131.3 ± 40.3 | 27.5 ± 10.3 | 90 ± 30.0 | 101.3 ± 18.8 |
| % F | 44.8 ± 4.4 | 31.6 ± 1.2 | 21.3 ± 0.9 | 24.5 ± 1.1 |

TABLE 10

PK profile of II-38 and 2,4-DNP released from II-38 after a single i.v. injection of II-38 at 1.6 mg/kg (eq. to 1 mg/kg 2,4-DNP), n = 2 rats

| PARAMETER (UNITS) | Route | |
|---|---|---|
| | II-38, i.v. Mean ± SEM | 2,4-DNP-R-II-38, i.v. Mean ± SEM |
| AUC (min * µg/mL) | 516 ± 53 | 380.2 ± 26.2 |
| $t_{1/2}$ (min) | 413.3 ± 65.3 | 130 ± 14.1 |
| $C_{max}$ (µg/mL) | 0.9 ± 0.05 | 2.2 ± 0.1 |
| Cl (mL/min/kg) | 3.1 ± 0.3 | |
| Vss (mL/kg) | 1861.3 ± 100.9 | |

Discussion

II-38 prodrug was synthesized as a drug delivery system in which the end goal was to achieve release of the parent drug (2,4-DNP) in the rat plasma. In vitro stability studies of II-38 (chapter 1) have indicated no evidence of 2,4-DNP formation from II-38 over the time course of 24 h in chemical buffers adjusted to pH 1.2 and 7.4. Likewise, II-38 prodrug was stable over a 24 h (both of II-38 and 2,4-DNP are not presented in the graph after 24 h) time course in simulated gastric fluid and simulated intestinal fluid that had been prepared by the methods of the USP. Thus, it can be predicted that II-38 delivered orally, will be absorbed via the GI tract into the systemic circulation as a stable entity and would be hydrolyzed under enzymatic conditions in the systemic circulation to release 2,4-DNP in plasma.

II-38 was evaluated in vivo to investigate the PK profile and relative bioavailability of 2,4-DNP-released from II-38 and to determine the time course of plasma levels of 2,4-DNP released from II-38 after a single oral dose of II-38 at 8, 40 and 80 mg/kg (eq. to 5, 25 and 50 mg/kg 2,4-DNP, respectively) or an i.v. bolus dose of 1.6 mg/kg (eq. to 1 mg/kg of 2,4-DNP) and compare the data to 2,4-DNP dosed orally at a single dose of 5 mg/kg or injected i.v. at 1 mg/kg in rats.

Following oral dosing, it can be noticed from the mean concentrations vs. time profile of II-38 prodrug and 2,4-DNP released from II-38 (FIGS. 19, 20, 21, and 22) that the carbamate linker in the codrug underwent hydrolysis to produce 2,4-DNP. II-38 prodrug showed slow dissolution to its parent drug, 2,4-DNP in the plasma, providing sustained release of the 2,4-DNP. It is worth noting that the hydrolysis of II-38 is not complete, as II-38 prodrug can be seen along with 2,4-DNP at all time points after oral and i.v. administration (FIGS. 19, 20, 21, and 22).

Since II-38 contains equimolar amounts of 2,4-DNP, it follows that an equal amount of II-38 must have hydrolyzed in plasma unless the carbamate linkage underwent cleavage to release 2,4-DNP in the intestine and/or liver. Alternatively, 2,4-DNP may have underwent metabolism in plasma after formation from II-38. Nonetheless, the predictions regarding in vivo stability of the II-38 prodrug were correct, because significant levels of 2,4-DNP were observed in all of the rats after oral and i.v. administration as indicated by the bioavailabilities of 58.5±8.1, 62.8±5.8, 41±5.1 and 50.1±11.5 for 2,4-DNP released from oral administration of II-38 at doses eq. to 5, 25 (methocel), 25, (PEG-400) and 50 mg/kg, respectively (Table 8). A one-compartment model describes i.v. dosing of 2,4-DNP and II-38. Peak plasma level of released 2,4-DNP ($C_{max}$: 2.2±1.1 µg/mL) was detected within 5 min indicating rapid cleavage of II-38. A non-compartment model adequately describes the PK of oral II-38 prodrug and its released 2,4-DNP. It can be shown that at any time point, the II-38 prodrug is present at a lower concentration than 2,4-DNP, FIGS. 19, 20, 21, and 22, and Tables 8 and 9. Thus, absorption of II-38 prodrug appears to be very rapid followed by fast cleavage and sustained release of 2,4-DNP as the later was detected in plasma within 5 min after oral dosing reaching a $C_{max}$ of 3.2-15.2 µg/mL within a $t_{max}$ of 120-180 min. The half-lives of elimination ($t_{1/2}$) being 136.3±10.9 and 90.0±9.9 min, for oral and i.v. dosing of 2,4-DNP, respectively. These results compare less with a prolonged average terminal half-life of 248.2±45.3, 185.9±18.1 and 334.1±63.0 for 2,4-DNP-released from II-38 at eq. doses of 25 (methocel), 25 (PEG-400) and 50 mg/kg (table 2.2), suggesting that oral administration of II-38 resulted in a significant improvement in the delivery of 2,4-DNP compared to administration of 2,4-DNP alone.

It was calculated that an approximately 12.0-, 2.2-, 3.4- and 1.4-fold increased level of 2,4-DNP was observed following oral dosing of 2,4-DNP parent drug compared to 2,4-DNP released from its II-38 prodrug after oral dosing of II-38 at eq. to 5, 25 (methocel), 25 (PEG-400) and 50 mg/kg, respectively (FIG. 23 and Table 8). The data from i.v. injection and oral dosing of II-38 does suggest that 2,4-DNP released from the II-38 prodrug may be subjected to other enzymatic activities taking place in different tissue compartments other than plasma, including the liver. In the rat plasma, the II-38 prodrug and its released 2,4-DNP are free to partition into other sites of metabolism, whereas in vitro plasma studies relied solely on plasma enzymes. However, release of 2,4-DNP from its prodrug over prolonged half-lives of 141.7-334.1 min and delayed $t_{max}$ of 120-240 min due to its slow release means prolonged exposure and less unexpected high peaks from released 2,4-DNP. In other word, the released 2,4-DNP following oral II-38 is suitable in suppressing acute adverse effects of 2,4-DNP due to rapid absorption and high plasma $C_{max}$.

Conclusion

In this study, oral administration of II-38 prodrug resulted in 2,4-DNP being significantly released and available from II-38 over time leading to prolonged exposure (AUC) and significant bioavailability of 2,4-DNP. Apparently, the II-38 prodrug is stable for formulation purposes and rapidly hydrolyzed in rat plasma.

Example 3: PK Profile of 2,4-DNP-Released from DNP-Piperidino

TABLE 11

PK profile of 2,4-DNP-released from DNP-piperidino after treatment with a single oral dose of DNP-piperidino equivalent to 5 mg/kg of 2,4-DNP formulated in DMSO:PEG-400:PBS (5:20:75)

| PARAMETER (UNITS) | Oral-1 | Oral-2 |
|---|---|---|
| AUC (min * ug/mL) | 22364.5 | 16184 |
| $t_{1/2}$ (min) | 656.1 | 773.4 |
| $C_{max}$ (ug/mL) | 19.2 | 12.4 |
| $t_{max}$ (min) | 240 | 240 |

Example 4: Hearing Loss Treatment

In Vivo Noise Exposure Pilot DNP (2,4-DNP) & Prodrug of DNP (II-38):

Rats, N=6/group: control, noise alone, noise+2,4-DNP (5 mpk), noise+II-38 (80 mpk). Noise exposure: 8 h, 105 dB, noise band 8-16 kHz. Treatment duration 5 days oral gavage q.d. starting day of noise. Endpoint: Compound Action Potential (CAP) recorded from the round window membrane 1-week post exposure. Threshold: intensity in dB SPL needed to produce 4 µV CAP amplitude.

Figure 3:
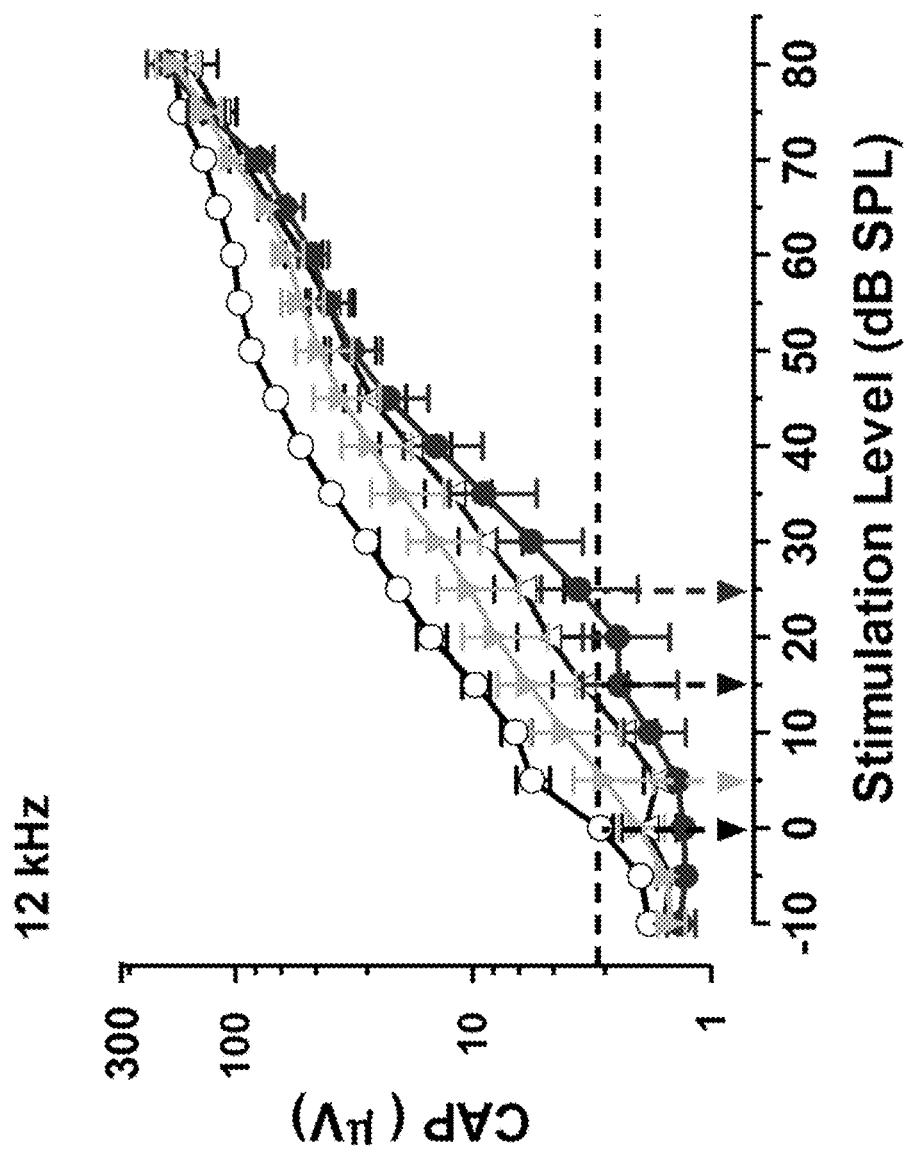
FIG. 3 is a chart illustrating the comparative results of an in vivo noise exposure experiment, including DNP (2,4-DNP) and a prodrug of DNP (II-38); II-38+Noise thresholds were 5 dB, approximately 20 dB lower (better) than the Noise alone group; DNP (2,4-DNP)+Noise thresholds were 15 dB, about 10 dB lower than Noise alone suggesting that DNP (2,4-DNP) can protect against noise induced hearing loss. Legend: circle—control (0 dB); triangle (pointing down)—II-38 (5 dB); triangle (pointing up)—2,4-DNP (15 dB); circle (solid)—noise (25 dB).
Figure 4:
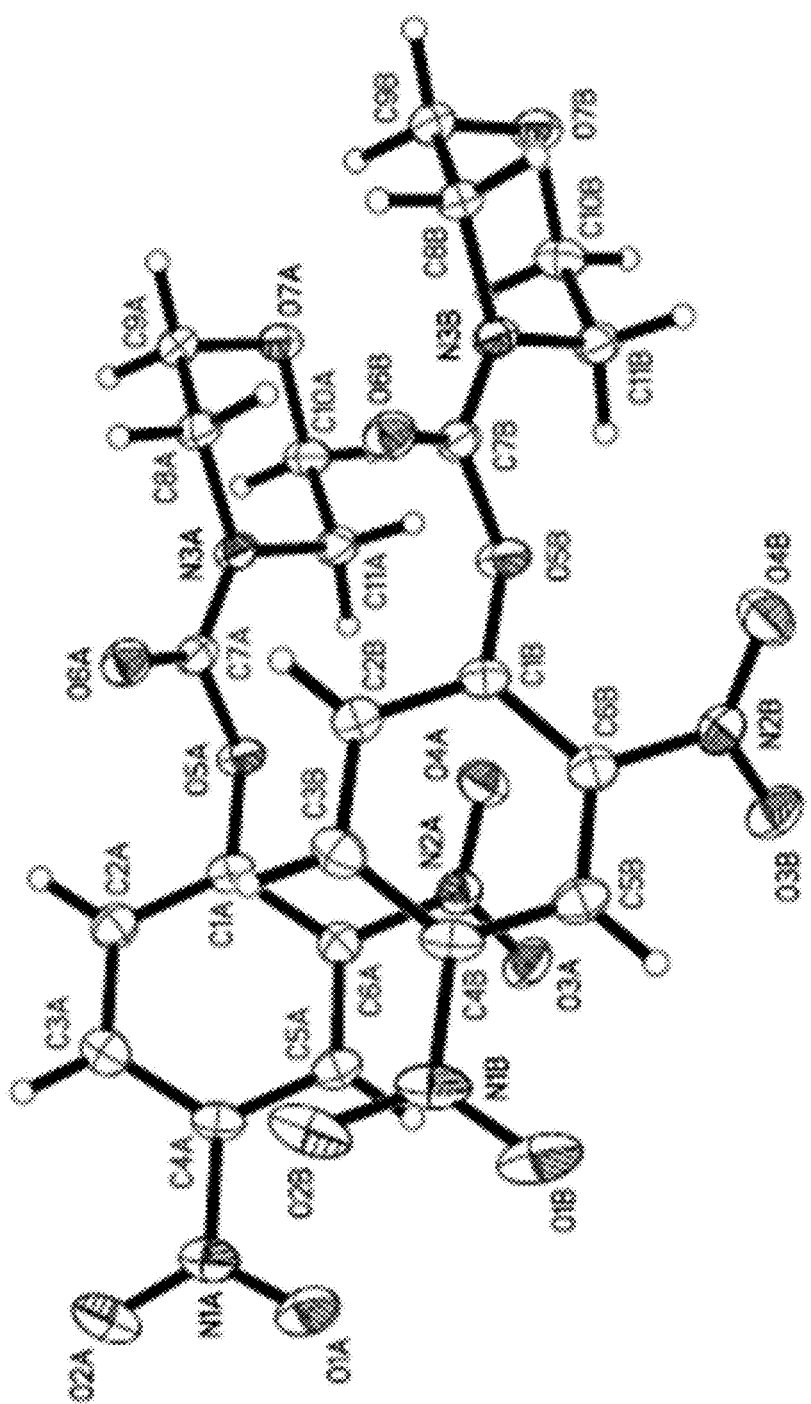
FIG. 4 illustrates the results of single crystal X-ray diffraction of 2,4-dinitrophenyl morpholine-4-carboxylate.

Results:

As shown in FIG. 3, II-38+Noise thresholds were 5 dB, approximately 20 dB lower (better) than the Noise alone group. These results suggest that DNP Prodrug (II-38 (can protect against noise induced hearing loss. Also as shown in FIG. 3, DNP (2,4-DNP)+Noise thresholds were 15 dB about 10 dB lower than Noise alone suggesting that DNP (2,4-DNP) can protect against noise induced hearing loss.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

We claim:

1. A composition comprising a dinitrophenol prodrug having a formula selected from:

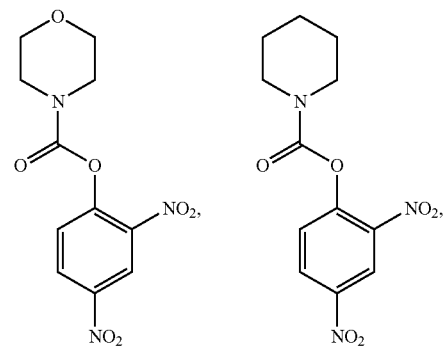

-continued

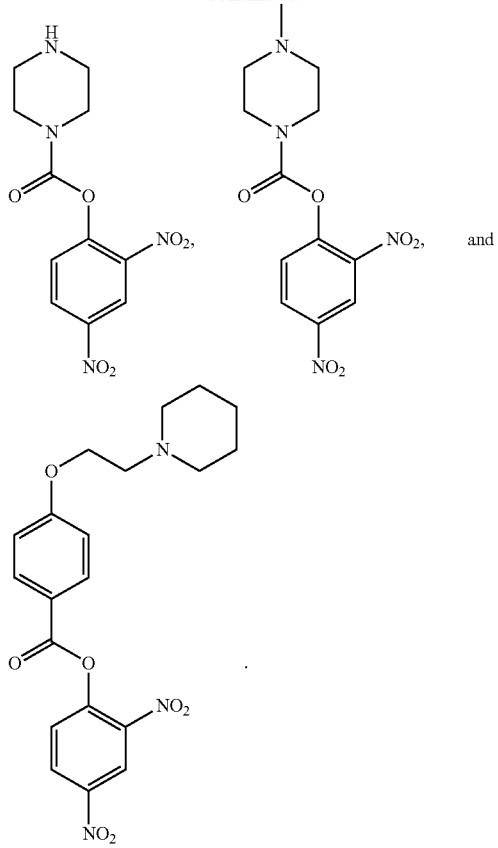

2. The composition of claim 1, wherein the prodrug is stable at a pH of 1-2.

3. The composition of claim 1, wherein the prodrug is stable at a pH of 4.5.

4. The composition of claim 1, wherein the prodrug is stable at a pH of 5-9.

5. A composition comprising a 2,3-DNP, 2,4-DNP, 2,5-DNP, 2,6-DNP, 3,4-DNP, or 3,5-DNP "Gemini" prodrug represented by Formula VII:

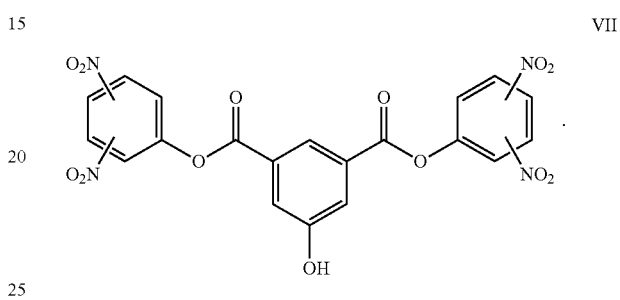

6. The composition of claim 5, wherein the prodrug is stable at a pH of 1-2.

7. The composition of claim 5, wherein the prodrug is stable at a pH of 4.5.

8. The composition of claim 5, wherein the prodrug is stable at a pH of 5-9.

9. A composition comprising a 2,4-DNP bioprecursor represented by Formula VIII or Formula IX:

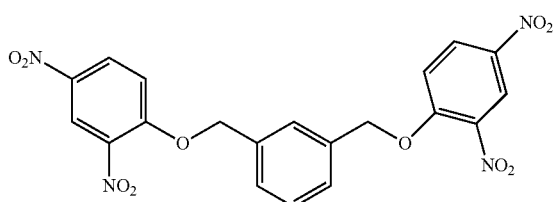

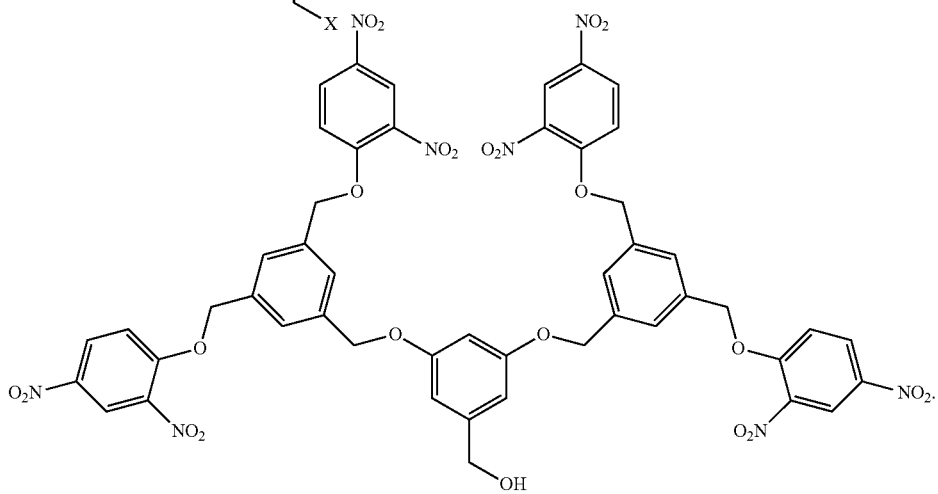

10. The composition of claim 9, wherein the bioprecursor is stable at a pH of 1-2.

11. The composition of claim 9, wherein the bioprecursor is stable at a pH of 4.5.

12. The composition of claim 9, wherein the bioprecursor is stable at a pH of 5-9.

13. The composition of claim 1, wherein the dinitrophenol prodrug has the formula:

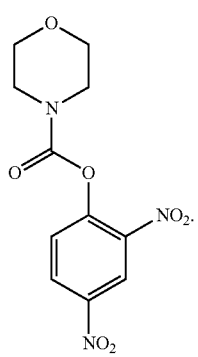 [SMILES: O=C(Oc1ccc([N+](=O)[O-])cc1[N+](=O)[O-])N1CCOCC1]

14. The composition of claim 1, wherein the dinitrophenol prodrug has the formula:

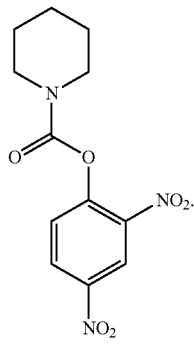 [SMILES: O=C(Oc1ccc([N+](=O)[O-])cc1[N+](=O)[O-])N1CCCCC1]

15. The composition of claim 1, wherein the dinitrophenol prodrug has the formula:

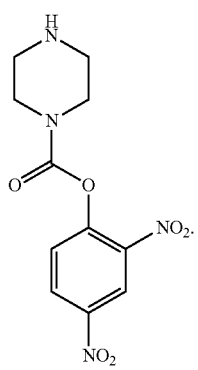 [SMILES: O=C(Oc1ccc([N+](=O)[O-])cc1[N+](=O)[O-])N1CCNCC1]

16. The composition of claim 1, wherein the dinitrophenol prodrug has the formula:

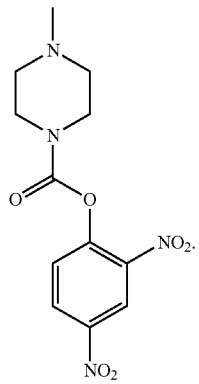 [SMILES: CN1CCN(C(=O)Oc2ccc([N+](=O)[O-])cc2[N+](=O)[O-])CC1]

17. The composition of claim 1, wherein the dinitrophenol prodrug has the formula:

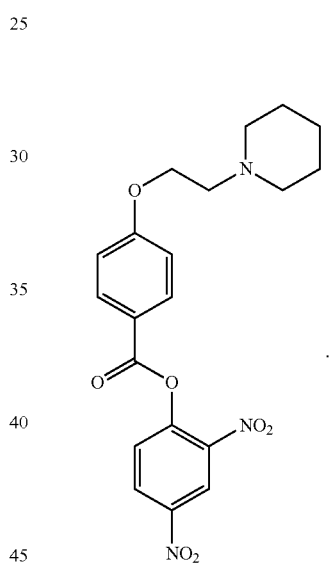

18. A depot nanoparticle formulation comprising a dinitrophenol prodrug having a formula selected from:

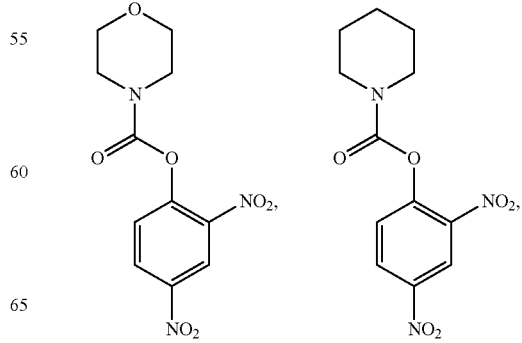

-continued
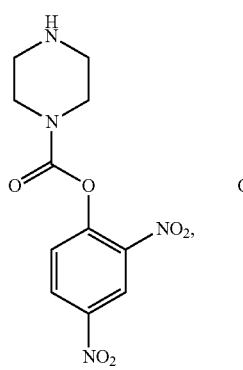 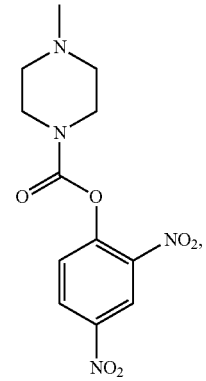
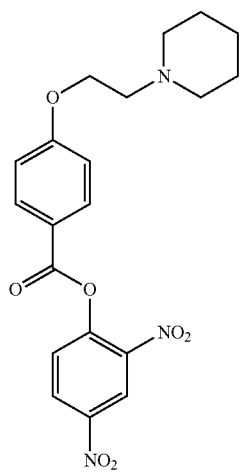
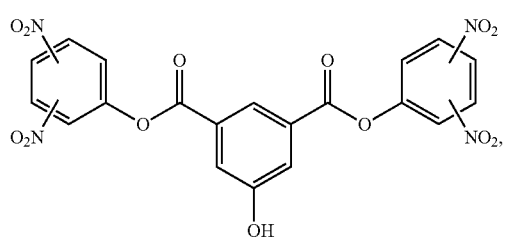
VII
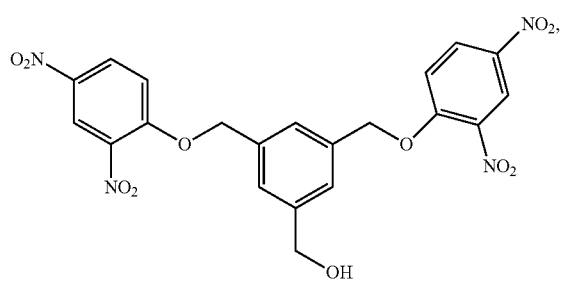
VIII
and
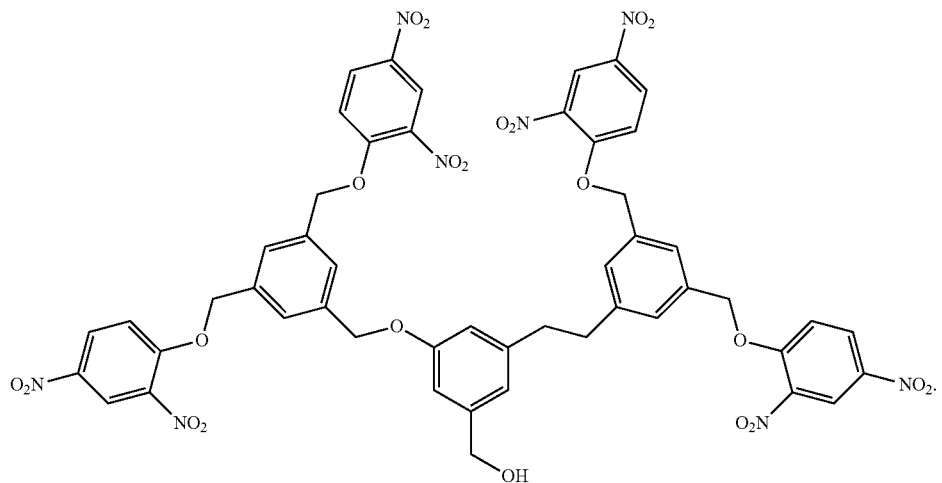
IX 19. The depot nanoparticle formulation of claim 18, wherein the prodrug is stable at a pH of 1-2.

20. The depot nanoparticle formulation of claim 18, wherein the prodrug is stable at a pH of 4.5.

21. The depot nanoparticle formulation of claim 18, wherein the prodrug is stable at a pH of 5-9.

* * * * *